(12) United States Patent
Sabbadini et al.

(10) Patent No.: US 7,794,713 B2
(45) Date of Patent: Sep. 14, 2010

(54) COMPOSITIONS AND METHODS FOR THE TREATMENT AND PREVENTION OF HYPERPROLIFERATIVE DISEASES

(75) Inventors: Roger A. Sabbadini, Lakeside, CA (US); Amy L. Cavalli, San Diego, CA (US); William A. Garland, San Clemente, CA (US)

(73) Assignee: Lpath, Inc., San Diego, CA (US)

( * ) Notice: Subject to any disclaimer, the term of this patent is extended or adjusted under 35 U.S.C. 154(b) by 525 days.

(21) Appl. No.: 11/261,935

(22) Filed: Oct. 28, 2005

(65) Prior Publication Data

US 2006/0171946 A1 Aug. 3, 2006

Related U.S. Application Data

(60) Provisional application No. 60/623,197, filed on Oct. 28, 2004.

(51) Int. Cl.
*A61K 39/395* (2006.01)
(52) U.S. Cl. .................. 424/130.1; 530/387.1
(58) Field of Classification Search .......... None
See application file for complete search history.

(56) References Cited

U.S. PATENT DOCUMENTS

| | | | |
|---|---|---|---|
| 3,773,919 A | 11/1973 | Boswell et al. |
| 3,940,382 A | 2/1976 | Umezawa et al. |
| 3,953,293 A | 4/1976 | Horii et al. |
| 3,953,422 A | 4/1976 | Pfeiffer |
| 3,959,255 A | 5/1976 | Chazan et al. |
| 3,962,429 A | 6/1976 | Furuno et al. |
| 3,974,137 A | 8/1976 | Schreiber et al. |
| 3,978,214 A | 8/1976 | Mallams et al. |
| 3,981,861 A | 9/1976 | Chazan et al. |
| 3,984,393 A | 10/1976 | Magerlein |
| 3,984,395 A | 10/1976 | Daniels et al. |
| 3,988,316 A | 10/1976 | Weinstein et al. |
| 3,996,205 A | 12/1976 | Magerlein |
| 3,997,524 A | 12/1976 | Nagabhushan |
| 4,002,608 A | 1/1977 | Wright et al. |
| 4,003,922 A | 1/1977 | Kavadias et al. |
| 4,009,328 A | 2/1977 | Mallams et al. |
| 4,011,390 A | 3/1977 | Weinstein et al. |
| 4,012,576 A | 3/1977 | Kawaguchi et al. |
| 4,020,269 A | 4/1977 | Hiraga et al. |
| 4,024,332 A | 5/1977 | Fenner et al. |
| 4,031,210 A | 6/1977 | Chazan et al. |
| 4,032,404 A | 6/1977 | Tomita et al. |
| 4,038,478 A | 7/1977 | Magerlein |
| 4,044,123 A | 8/1977 | Daniels et al. |
| 4,049,498 A | 9/1977 | Weinstein et al. |
| 4,051,315 A | 9/1977 | Godfrey et al. |
| 4,064,339 A | 12/1977 | Coussediere et al. |
| 4,065,615 A | 12/1977 | Horii et al. |
| 4,066,752 A | 1/1978 | Mallams et al. |
| 4,085,208 A | 4/1978 | Mallams et al. |
| 4,101,556 A | 7/1978 | Kavadias et al. |
| 4,107,435 A | 8/1978 | Ross |
| 4,117,221 A | 9/1978 | Daniels |
| 4,120,955 A | 10/1978 | Umezawa et al. |
| 4,125,707 A | 11/1978 | Arcamone et al. |
| 4,136,254 A | 1/1979 | Nagabhushan et al. |
| 4,140,849 A | 2/1979 | Umezawa et al. |
| 4,146,617 A | 3/1979 | Chazan et al. |
| 4,166,114 A | 8/1979 | Igarashi |
| 4,169,198 A | 9/1979 | Martin et al. |
| 4,170,642 A | 10/1979 | Umezawa et al. |
| 4,170,643 A | 10/1979 | Gero et al. |
| 4,176,178 A | 11/1979 | Martin et al. |
| 4,178,437 A | 12/1979 | Thomas |
| 4,179,337 A | 12/1979 | Davis et al. |
| 4,181,797 A | 1/1980 | Naito et al. |
| 4,183,920 A | 1/1980 | Kurath et al. |
| 4,187,296 A | 2/1980 | Tadanier et al. |
| 4,187,297 A | 2/1980 | Martin et al. |
| 4,187,298 A | 2/1980 | Martin et al. |
| 4,187,299 A | 2/1980 | Post |
| 4,187,372 A | 2/1980 | Carney et al. |
| 4,189,569 A | 2/1980 | Carney et al. |
| 4,192,867 A | 3/1980 | Martin et al. |
| 4,195,170 A | 3/1980 | Umezawa et al. |
| 4,196,197 A | 4/1980 | Tadanier et al. |

(Continued)

FOREIGN PATENT DOCUMENTS

CA 2019559 C 12/1990

(Continued)

OTHER PUBLICATIONS

Sawada et al. Ordering of ceramide formation, caspase activation, and Bax/Bcl-2 expression during etoposide-induced apoptosis in C6 glioma cells. Cell Death and Differentiation, 7:761-772, 2000.*

(Continued)

*Primary Examiner*—Larry R. Helms
*Assistant Examiner*—Meera Natarajan
(74) *Attorney, Agent, or Firm*—BioTechnology Law Group; Daniel M. Chambers

(57) ABSTRACT

Monotherapies and combination therapies for treating hyperproliferative disorders are described, as are compositions for performing such methods.

9 Claims, 11 Drawing Sheets

U.S. PATENT DOCUMENTS

| | | |
|---|---|---|
| 4,199,570 A | 4/1980 | Igarashi et al. |
| 4,200,628 A | 4/1980 | Igarashi et al. |
| 4,201,774 A | 5/1980 | Igarashi et al. |
| 4,205,070 A | 5/1980 | Tadanier et al. |
| 4,207,314 A | 6/1980 | Collum |
| 4,207,415 A | 6/1980 | Carney et al. |
| 4,208,407 A | 6/1980 | Carney et al. |
| 4,208,531 A | 6/1980 | Canas-Rodriquez |
| 4,209,511 A | 6/1980 | Oka et al. |
| 4,212,859 A | 7/1980 | Daniels et al. |
| 4,213,971 A | 7/1980 | McAlpine |
| 4,213,972 A | 7/1980 | Martin |
| 4,213,974 A | 7/1980 | Martin |
| 4,214,074 A | 7/1980 | Richardson et al. |
| 4,214,075 A | 7/1980 | Tadanier et al. |
| 4,214,076 A | 7/1980 | McAlpine |
| 4,214,078 A | 7/1980 | Goldstein et al. |
| 4,214,079 A | 7/1980 | Martin |
| 4,214,080 A | 7/1980 | Carney |
| 4,216,210 A | 8/1980 | Carney et al. |
| 4,217,446 A | 8/1980 | Moore |
| 4,219,642 A | 8/1980 | Collum et al. |
| 4,219,643 A | 8/1980 | Seely |
| 4,219,644 A | 8/1980 | Goldstein et al. |
| 4,220,756 A | 9/1980 | Kloss et al. |
| 4,223,022 A | 9/1980 | Rosenkrantz et al. |
| 4,223,024 A | 9/1980 | McAlpine et al. |
| 4,226,978 A | 10/1980 | Boguslaski et al. |
| 4,230,847 A | 10/1980 | Nagabhushan et al. |
| 4,242,331 A | 12/1980 | Gasc et al. |
| 4,248,865 A | 2/1981 | Igarashi et al. |
| 4,250,170 A | 2/1981 | Kawaguchi et al. |
| 4,250,304 A | 2/1981 | Martin et al. |
| 4,251,511 A | 2/1981 | Whaley et al. |
| 4,251,516 A | 2/1981 | Martin et al. |
| 4,252,972 A | 2/1981 | Tadanier et al. |
| 4,255,421 A | 3/1981 | Watanabe et al. |
| 4,273,923 A | 6/1981 | Igarashi et al. |
| 4,275,149 A | 6/1981 | Litman et al. |
| 4,279,997 A | 7/1981 | Oka et al. |
| 4,283,528 A | 8/1981 | Daniels et al. |
| RE30,750 E | 9/1981 | Diack et al. |
| 4,288,547 A | 9/1981 | Yamamoto |
| 4,297,485 A | 10/1981 | Umezawa et al. |
| 4,297,486 A | 10/1981 | Fujii et al. |
| 4,301,144 A | 11/1981 | Iwashita et al. |
| 4,312,859 A | 1/1982 | Petersen et al. |
| 4,317,904 A | 3/1982 | Martin et al. |
| 4,318,980 A | 3/1982 | Boguslaski et al. |
| 4,319,022 A | 3/1982 | Martin et al. |
| 4,330,673 A | 5/1982 | Rosenbrook, Jr. |
| RE30,985 E | 6/1982 | Cartaya |
| 4,336,369 A | 6/1982 | Petersen et al. |
| 4,337,336 A | 6/1982 | Umezawa et al. |
| 4,347,354 A | 8/1982 | Cron et al. |
| 4,349,667 A | 9/1982 | Fujii et al. |
| 4,365,020 A | 12/1982 | Gado et al. |
| 4,369,251 A | 1/1983 | Jarai et al. |
| 4,376,110 A | 3/1983 | David et al. |
| 4,380,625 A | 4/1983 | Stadler et al. |
| 4,387,219 A | 6/1983 | Yamamoto et al. |
| 4,418,193 A | 11/1983 | McAlpine et al. |
| 4,424,343 A | 1/1984 | Cron et al. |
| 4,424,344 A | 1/1984 | Kirst et al. |
| 4,424,345 A | 1/1984 | Kirst et al. |
| 4,438,107 A | 3/1984 | Watanabe et al. |
| 4,438,260 A | 3/1984 | Petersen et al. |
| 4,455,419 A | 6/1984 | Umezawa et al. |
| 4,468,512 A | 8/1984 | Kirst et al. |
| 4,468,513 A | 8/1984 | Kirst et al. |
| 4,485,045 A | 11/1984 | Regen |
| 4,486,418 A | 12/1984 | Watanabe et al. |
| 4,493,831 A | 1/1985 | Takaya et al. |
| 4,496,689 A | 1/1985 | Mitra |
| 4,503,046 A | 3/1985 | Loibner et al. |
| 4,544,545 A | 10/1985 | Ryan et al. |
| 4,554,269 A | 11/1985 | Takaya et al. |
| 4,560,655 A | 12/1985 | Baker |
| 4,568,649 A | 2/1986 | Bertoglio-Matte |
| 4,617,293 A | 10/1986 | Wahlig et al. |
| 4,626,513 A | 12/1986 | Burton et al. |
| 4,640,835 A | 2/1987 | Shimizu et al. |
| 4,645,760 A | 2/1987 | Pierson |
| 4,647,656 A | 3/1987 | Watanabe et al. |
| 4,656,160 A | 4/1987 | Takaya et al. |
| 4,657,866 A | 4/1987 | Kumar |
| 4,658,830 A | 4/1987 | Sarnoff |
| 4,670,417 A | 6/1987 | Iwasaki et al. |
| 4,676,980 A | 6/1987 | Segal et al. |
| 4,737,456 A | 4/1988 | Weng et al. |
| 4,767,704 A | 8/1988 | Cleveland et al. |
| 4,791,192 A | 12/1988 | Nakagawa et al. |
| 4,816,397 A | 3/1989 | Boss et al. |
| 4,816,567 A | 3/1989 | Cabilly et al. |
| 4,855,287 A | 8/1989 | Watanabe et al. |
| 4,873,225 A | 10/1989 | Umezawa et al. |
| 4,895,724 A | 1/1990 | Cardinal et al. |
| 4,902,790 A | 2/1990 | Mangia et al. |
| 4,927,762 A | 5/1990 | Darfler |
| 4,946,778 A | 8/1990 | Ladner et al. |
| 4,985,549 A | 1/1991 | Giobbio et al. |
| 5,010,175 A | 4/1991 | Rutter et al. |
| 5,013,556 A | 5/1991 | Woodle et al. |
| 5,122,469 A | 6/1992 | Mather et al. |
| 5,204,244 A | 4/1993 | Fell et al. |
| 5,225,539 A | 7/1993 | Winter et al. |
| 5,229,275 A | 7/1993 | Goroff |
| 5,260,203 A | 11/1993 | Ladner et al. |
| 5,270,163 A | 12/1993 | Gold et al. |
| 5,288,514 A | 2/1994 | Ellman |
| 5,314,695 A | 5/1994 | Brown |
| 5,430,160 A | 7/1995 | Holton |
| 5,442,047 A | 8/1995 | Tann et al. |
| 5,455,030 A | 10/1995 | Ladner et al. |
| 5,488,038 A | 1/1996 | Kondo et al. |
| 5,506,337 A | 4/1996 | Summerton et al. |
| 5,518,889 A | 5/1996 | Ladner et al. |
| 5,519,134 A | 5/1996 | Acevedo et al. |
| 5,525,735 A | 6/1996 | Gallop et al. |
| 5,530,101 A | 6/1996 | Queen et al. |
| 5,534,615 A | 7/1996 | Baker et al. |
| 5,534,621 A | 7/1996 | Ladner et al. |
| 5,539,083 A | 7/1996 | Cook et al. |
| 5,545,807 A | 8/1996 | Surani et al. |
| 5,549,974 A | 8/1996 | Holmes |
| 5,565,332 A | 10/1996 | Hoogenboom et al. |
| 5,567,610 A | 10/1996 | Borrebaeck et al. |
| 5,569,588 A | 10/1996 | Ashby et al. |
| 5,573,905 A | 11/1996 | Lerner et al. |
| 5,585,089 A | 12/1996 | Queen et al. |
| 5,589,369 A | 12/1996 | Seidman et al. |
| 5,591,669 A | 1/1997 | Krimpenfort et al. |
| 5,593,853 A | 1/1997 | Chen et al. |
| 5,618,795 A | 4/1997 | Kondo et al. |
| 5,621,085 A | 4/1997 | Dall'Asta et al. |
| 5,624,821 A | 4/1997 | Winter et al. |
| 5,631,394 A | 5/1997 | Wei et al. |
| 5,656,735 A | 8/1997 | Dall'Asta et al. |
| 5,677,189 A | 10/1997 | Igarashi et al. |
| 5,677,337 A | 10/1997 | Wei et al. |
| 5,693,761 A | 12/1997 | Queen et al. |
| 5,693,762 A | 12/1997 | Queen et al. |
| 5,702,892 A | 12/1997 | Mulligan-Kehoe |
| 5,714,350 A | 2/1998 | Co et al. |

| | | |
|---|---|---|
| 5,763,587 A | 6/1998 | Mangia |
| 5,770,429 A | 6/1998 | Lonberg et al. |
| 5,777,085 A | 7/1998 | Co et al. |
| 5,814,488 A | 9/1998 | Zhao et al. |
| 5,821,047 A | 10/1998 | Garrard et al. |
| 5,834,597 A | 11/1998 | Tso et al. |
| 5,840,867 A | 11/1998 | Toole et al. |
| 5,861,155 A | 1/1999 | Lin |
| 5,869,620 A | 2/1999 | Whitlow et al. |
| 5,876,747 A | 3/1999 | Stracher et al. |
| 5,882,644 A | 3/1999 | Chang et al. |
| 5,912,144 A | 6/1999 | Au-Young et al. |
| 5,932,448 A | 8/1999 | Tso et al. |
| 6,013,256 A | 1/2000 | Light et al. |
| 6,025,165 A | 2/2000 | Whitlow et al. |
| 6,027,725 A | 2/2000 | Whitlow et al. |
| 6,031,071 A | 2/2000 | Mandeville et al. |
| 6,046,037 A | 4/2000 | Hiatt et al. |
| 6,075,181 A | 6/2000 | Kucherlapati et al. |
| 6,080,321 A | 6/2000 | Spickermann |
| 6,098,631 A | 8/2000 | Holoshitz et al. |
| 6,114,598 A | 9/2000 | Kucherlapati et al. |
| 6,121,246 A | 9/2000 | Isner |
| 6,129,914 A | 10/2000 | Weiner et al. |
| 6,130,235 A | 10/2000 | Mavunkel et al. |
| 6,150,584 A | 11/2000 | Kucherlapati et al. |
| 6,162,963 A | 12/2000 | Kucherlapati et al. |
| 6,180,370 B1 | 1/2001 | Queen et al. |
| 6,210,671 B1 | 4/2001 | Co |
| 6,310,191 B1 | 10/2001 | Collins et al. |
| 6,329,511 B1 | 12/2001 | Vasquez et al. |
| 6,350,861 B1 | 2/2002 | Co et al. |
| 6,407,213 B1 | 6/2002 | Carter et al. |
| 6,479,284 B1 | 11/2002 | Marasco et al. |
| 6,500,931 B1 | 12/2002 | Tempest et al. |
| 6,548,640 B1 | 4/2003 | Winter |
| 6,571,638 B2 | 6/2003 | Hines et al. |
| 6,610,835 B1 | 8/2003 | Liotta et al. |
| 6,613,322 B2 | 9/2003 | Tabas et al. |
| 6,639,055 B1 | 10/2003 | Carter et al. |
| 6,649,362 B2 | 11/2003 | Gamble et al. |
| 6,858,383 B2 | 2/2005 | Sabbadini |
| 6,881,546 B2 | 4/2005 | Sabbadini |
| 7,060,808 B1 | 6/2006 | Goldstein et al. |
| 7,087,409 B2 | 8/2006 | Barbas, III et al. |
| 7,169,390 B2 * | 1/2007 | Sabbadini ............... 424/155.1 |
| 2003/0027304 A1 * | 2/2003 | Sabbadini ............... 435/184 |
| 2003/0096022 A1 | 5/2003 | Sabbadini |
| 2003/0229208 A1 | 12/2003 | Queen et al. |
| 2005/0226862 A1 | 10/2005 | Sabbadini |

FOREIGN PATENT DOCUMENTS

| | | |
|---|---|---|
| EP | 0154734 A1 | 9/1985 |
| EP | 0183070 A2 | 6/1986 |
| EP | 0244234 A2 | 11/1987 |
| EP | 0344955 A2 | 12/1989 |
| EP | 0125023 B1 | 6/1991 |
| EP | 0519596 A1 | 5/1992 |
| EP | 0120694 B1 | 7/1993 |
| EP | 0194276 B1 | 8/1993 |
| EP | 0239400 B1 | 8/1994 |
| WO | WO 86/01533 A1 | 3/1986 |
| WO | WO 87/00195 A1 | 1/1987 |
| WO | WO 90/03430 A1 | 4/1990 |
| WO | WO 91/19735 A1 | 12/1991 |
| WO | WO 91/19813 A1 | 12/1991 |
| WO | WO 92/00091 A1 | 1/1992 |
| WO | WO 93/11161 A1 | 6/1993 |
| WO | WO 93/20242 A1 | 10/1993 |
| WO | WO 94/16731 A1 | 8/1994 |
| WO | WO 96/27011 A1 | 9/1996 |
| WO | WO 96/32478 A1 | 10/1996 |
| WO | WO 97/00271 A1 | 1/1997 |
| WO | WO 98/52547 A1 | 11/1998 |
| WO | WO 01/37836 A1 | 5/2001 |
| WO | WO 02/17899 A2 | 3/2002 |
| WO | WO 02/051439 A2 | 7/2002 |
| WO | WO 03/097028 A1 | 11/2003 |
| WO | WO 2006/105062 A2 | 10/2006 |

OTHER PUBLICATIONS

Chemotheapry Drugs—Etoposide (http://www.chemocare.com/BIO/etoposide.asp).*
Kolesnick, Richard. The therapeutic potential of modulating the ceramide/sphingomyelin pathway. The J. of Clinical Investigation, vol. 110, No. 1, p. 3-8, Jul. 2002.*
Presta et al. Cancer Research 57, p. 4593-4599, Oct. 15, 1997.*
Lee et al. (BBRC, vol. 264, pp. 743-750, 1999) (copyright protected article).*
Siess et al., "Lysophosphatidic acid and sphingosine 1-phosphate: two lipid villains provoking cardiovascular diseases?," IUBMB Life 49:167-171 (2000).
Yu et al., "Pivotal role for acidic sphingomyelinase in cerebral ischemia-induced ceramide and cytokine production, and neuronal apoptosis," J of Molecular Neuroscience 15(2):85-97 (2000).
Abe et al., "Novel Antitumor Antibiotics, Saptomycins D and E," J. Antibiot. (Tokyo) 44(8):908-911 (1991).
Abe et al., "Novel Antitumor Antibiotics, Saptomycins. I. Taxonomy of the Producing Organism, Fermentation, HPLC Analysis and Biological Activities" J. Antibiot. (Tokyo) 46(10):1530-1535 (1993).
Abe et al., "Novel Antitumor Antibiotics Saptomycins. II. Isolation, Physico-chemical Properties and Structure Elucidation" J. Antibiot. (Tokyo) 46(10):1536-1549 (1993).
Adam et al., "A Novel Cytoplasmic Domain of the p55 Tumor Necrosis Factor Receptor Initiates the Neutral Sphingomyelinase Pathway," J. Bio. Chem. 271(24):14617-14622 (1996).
Adzick et al., "Cells, matrix, growth factors, and the surgeon. The biology of scarless fetal wound repair," Ann. Surg. 220(1):10-18 (1994).
Akiyama et al., "Intraocular Injection of an Aptamer that Binds PDGF-B: A Potential Treatment for Proliferative Retinopathies," J. Cell. Physiol. 207(2):407-412 (2006).
Alemany et al., "Stimulation of Sphingosine-1-Phosphate Formation by the P2Y2 Receptor in HL-60 Cells: Ca2+ Requirement and Implication in Receptor-Mediated Ca2+ Mobilization, but not MAP Kinase Activation," Mol. Pharm. 58(3):491-497 (2000).
Allen, "Myocardial protection: is there a role for gene therapy?," Ann. Thorac. Surg. 68(5):1924-1928 (1999).
Allende et al., "Sphingosine-1-Phosphate Receptors and the Development of the Vascular System," Biochim. Biophys. Acta 1582(1-3):222-227 (2002).
Ambati et al., "Age-Related Macular Degeneration: Etiology, Pathogenesis, and Therapeutic Strategies," Surv. Ophthalmol. 48(3):257-293 (2003).
Amin et al., "Growth Factor Localization in Choroidal Neovascular Membranes of Age-Related Macular Degeneration," Investigat. Ophthalmol. Vis.Sci. 35(8):3178-3188 (1994).
Andrews et al., "Platelet-Derived Growth Factor Plays a Key Role in Proliferative Vitreoretinopathy," Investigat. Ophthalmol. Vis.Sci. 40(11):2683-2689 (1999).
Annabi et al., "Matrix Metalloproteinase Regulation of Sphingosine-1-Phosphate-Induced Angiogenic Properties of Bone Marrow Stromal Cells," Exp. Hematol. 31(7):640-649 (2003).
Antman et al., "Abciximab Facilitates the Rate and Extent of Thrombolysis: Results of the Thrombolysis in Myocardial Infarction (TIMI) 14 Trial," Circulation 99(21):2720-2732, (1999).
Argraves et al., "Sphingosine-1-Phosphate Signaling Promotes Critical Migratory Events in Vasculogenesis," J. Bio. Chem. 279(48):50580-50590 (2004).
Armulik et al, "Endothelial-Pericyte Interactions," Circ. Res. 97(6):512-523 (2005).
Asahara et al., "Tie2 Receptor Ligands, Angiopoietin-1 and Angiopoietin-2, Modulate VEGF-Induced Postnatal Neovascularization," Circ. Res. 83(3):233-240 (1998).

Awad et al., "Selective Sphingosine-1-Phosphate 1 Receptor Activation reduces Ischemia-Reperfusion Injury in Mouse Kidney," Am. J. Physiol. Renal Physiol. 290(6):F1516-F1524 (2006).

Baker et al., "Direct Quantitative Analysis of Lysophosphatidic Acid Molecular Species by Stable Isotope Dilution Electrospray Ionization Liquid Chromatography-Mass Spectrometry," Anal. Biochem. 292(2):287-295 (2001).

Barnes et al., "Methods for Growth of Cultured Cells in Serum-Free Medium," Anal. Biochem. 102(2):255-270 (1980).

Baroni et al., "Stimulatory Autoantibodies to the PDGF Receptor in Systemic Sclerosis," New Engl. J. Med. 354(25):2667-2676 (2006).

Baudhuin et al., "S1P3-Mediated Akt Activation and Cross-Talk with Platelet-Derived Growth Factor Receptor (PDGFR)," FASEB J. 18(2):341-343 (2004).

Becerril et al., "Growth Factor Levels and ROP," Ophthalmology 112(12):2238 (2005).

Beeler et al., " The *Saccharomyces cerevisiae* TSC10-YBR265w Gene Encoding 3-Ketosphinganine Reductase Is Identified in a Screen for Temperature-sensitive Suppressors of the Ca2+-sensitive csg2DELTA Mutant" J. Biol. Chem. 273(46):30688-30694 (1998).

Benjamin et al., "A Plasticity Window for Blood Vessel Remodeling is Defined by Pericyte Coverage of the Preformed Endothelial and is Regulated by PDGF-B and VEGF," Development 125(9):1591-1598 (1998).

Berge et al., "Pharmaceutical Salts," J. Pharm. Sci. 66(1):1-19 (1977).

Bergers et al., "The Role of Pericytes in Blood Vessel Formation and Maintenance," Neuro. Oncol. 7(4):452-464 (2005).

Bohler et al., "FTY720 Exerts Differential Effects on CD4+ and CD8+ T-Lymphocyte Subpopulations Expressing Chemokine and Adhesion Receptors," Nephrol. Dial. Transplant. 19(3):702-713 (2004).

Bohler et al, "Novel Mediators of FTY720 in Human Lymphocytes," Transplantation 79(4):492-495 (2005).

Boulton et al., "Intravitreal Growth Factors in Proliferative Diabetic Retinopathy: Correlation with Neovascular Activity and Glycaemic Management," Br. J. Ophthalmol. 81(3):228-233 (1997).

Boushey et al., "Basic Mechanisms of Asthma," Environ. Health Perspect. 103(Suppl 6):229-233 (1995).

Brennan et al., "Preparation of bispecific antibodies by chemical recombination of monoclonal immunoglobulin G1 fragments," Science 229(4708):81-83 (1985).

Brenner et al., "Fas- or Ceramide-induced Apoptosis Is Mediated by a Rac1-regulated Activation of Jun N-terminal Kinase-p38 Kinases and GADD153," J. Biol. Chem. 272(35):22173-22181 (1997).

Brill et al., "Altromycins, Novel Pluramycin-like Antibiotics. II. Isolation and Elucidation of Structure," J. Antibiot. (Tokyo) 43(3):229-237 (1990).

Brindley, "Lipid Phosphate Phosphatases and Related Proteins: Signaling Functions in Development, Cell Division, and Cancer," J. Cell. Biochem. 92(5):900-912 (2004).

Brown et al., "Ranibizumab versus Verteporfin for Neovascular Age-Related Macular Degeneration," New Engl. J. Med. 355(14):1432-1444 (2006).

Buchschacher et al., "Development of Lentiviral Vectors for Gene Therapy for Human Diseases," Blood 95(8):2499-2504 (2000).

Budde et al., "First Human Trial of FTY720, A Novel Immunomodulator, in Stable Renal Transplant Patients," J. Am. Soc. Nephrol. 13(4):1073-1083 (2002).

Bugg et al., "Drugs by Design," Sci. Am. 269(6):92-98 (1993).

Butrus et al., "Increased Numbers of Mast Cells in Pterygia," Am. J. Ophthalmol. 119(2):236-237 (1995).

Bylsma et al., "Treatment of Age-Related Macular Degeneration," Clin. Exp. Optom. 88(5):322-334 (2005).

Calder et al., "Increased CD4+ Expression and Decreased IL-10 in the Anterior Chamber in Idiopathic Uveits," Invest. Ophthalmol. Vis. Sci. 40(9):2019-2024 (1999).

Carter et al., "High Level *Escherichia coli* Expression and Production of a Bivalent Humanized Antibody Fragment," Bio/Technology 10(2):163-167 (1992).

Cassidy et al., "Platelet Derived Growth Factor and Fibroblast Growth Factor Basic Levels in the Vitreous of Patients with Vitreoretinal Disirders," Br. J. Ophthalmol. 82(2):181-185 (1998).

Chae et al., "Requirement for Sphingosine-1-Phosphate Receptor-1 in Tumor Angiogenesis Demonstrated by in Vivo RNA Interference," J. Clin. Invest. 114(8):1082-1089 (2004).

Champe et al., "Monoclonal Antibodies That Block the Activity of Leukocyte Function-associated Antigen 1 Recognize Three Discrete Epitopes in the Inserted Domain of CD11a," J. Biol. Chem. 270(3):1388-1394 (1995).

Chen et al., "Analogous' Organic Synthesis of Small-Compound Libraries: Validation of Combinatorial Chemistry in Small-Molecule Synthesis," J. Amer. Chem. Soc. 116(6):2661-2662 (1994).

Chen et al., "Production and Appliction of LPA Polyclonal Antibodies," Bioorg. Medic. Chem. Lett. 10(15):1691-1693 (2000).

Chen et al., "Specific Receptor Subtype Mediation of LPA-Induced Dual Effects in Cardiac Fibroblasts," FEBS Lett. 580(19):4737-4745 (2006).

Chiba et al., "FTY720, a Novel Immunosuppressant, Induces Sequestration of Circulating Mature Lymphocytes by Acceleration of Lymphocyte Homing in Rats. I. FTY720 Selectively Decreases the Number of Circulating Mature Lymphocytes by Acceleration of Lymphocyte Homing," J. Immunol. 160(10):5037-5044 (1998).

Chmura et al. "Down-Regulation of Ceramide Production Abrogates Ionizing Radiation-Induced Cytochrome c Release and Apoptosis," Mol. Pharmcol. 57(4):792-796 (2000).

Chothia et al., "Domain Association in Immunoglobulin Molecules: The Packing of Variable Domains," J. Mol. Biol. 186(3):651-663 (1985).

Chothia et al., "Canonical Structures for the Hypervariable Regions of Immunoglobulins," J. Mol. Biol. 196(4):901-917 (1987).

Chun et al, "Lysophospholipid Receptors as Potential Drug Targets in Tissue Transplantation and Autoimmune Diseases," Curr. Pharm. Des. 12(2):161-171 (2006).

Cinamon et al., "Sphingosine 1-Phosphate Receptor 1 Promotes B Cell Localization in the Splenic Marginal Zone," Nat. Immunol. 5(7):713-720 (2004).

Ciulla et al., "Presumed Ocular Histoplasmosis Syndrome: Update on Epidemiology, Pathogenesis, and Photodynamic, Antiangiogenic, and Surgical Therapies," Curr. Opin. Ophthalmol. 12(6):442-449 (2001).

Condrescu et al., "Inhibition of Sodium-Calcium Exchange by Ceramide and Sphingosine," J. Biol. Chem. 276(6):4046-4054 (2001).

Cousins et al., "Monocyte Activation in Patients with Age-Related Macular Degeneration," Arch Ophthal. 122(7):1013-1018 (2004).

Cunningham et al., "High-resolution epitope mapping of hGH-receptor interactions by alanine-scanning mutagenesis," Science 244(4908):1081-1085 (1989).

Cuvillier et al., "Sphingosine-1-Phosphate Antagonizes Apoptosis of Human Leukemia Cells by Inhibiting Release of Cytochrome C and SMAC-DIABLO From Mitochondria," Blood 98(9):2828-2836 (2001).

Cyster, "Chemokines, Sphingosine-1-Phosphate, and Cell Migration in Secondary Lymphoid Organs," Annu. Rev. Immunol. 23:127-159 (2005).

Dantas et al., "Sphingosine-1-Phosphate and Control of Vascular Tone," Am. J. Physiol. Heart Circ. Physiol. 284(6):H2045-H2052 (2003).

Danthinne et al., "Production of First Generation Adenovirus Vectors: A Review," Gene Ther. 7(20):1707-1714 (2000).

Dart, "Corneal Toxicity: The Epithelium and Stroma in Iatrogenic and Factitous Disease," Eye 17(8):886-892 (2003).

Davaille et al., "Antiproliferative Properties of Sphingosine 1-Phosphate in Human Hepatic Myofibroblasts," J. Biol. Chem. 275(44):34268-34633 (2000).

Dawson, "Activity of SC33428, a Novel Bishydrazone-Bridged Derivative of 4-Demethoxydaunorubicin, against Experimental Tumors in Mice," Cancer Res. 43(6):2880-2883 (1983).

Deguchi et al., "The S1P Receptor Modulator FTY720 Prevents the Development of Experimental Colitis in Mice," Oncol. Rep. 16(4):699-703 (2006).

Denk et al., "Effect of Growth Factors on the Activation of Human Tenon's Capsule Fibroblasts," Curr. Eye Res. 27(1):35-44 (2003).

Desmouliere et al., "Transforming Growth Factor β1 Induces α Smooth Muscle Actin Expression in Granulation Tissue Myofibroblasts and in Quiescent and Growing Cultured Fibroblasts," J. Cell Biol. 122(1):103-111 (1993).

Deutschman et al., "Predicting Obstructive Coronary Artery Disease with Serum Sphingosine-1-Phosphate," Am. Heart J. 146(1):62-68 (2003).

Di Girolamo et al., "UVB-Mediated Induction of Cytokines and Growth Factors in Pterygium Epithelial Cells Involves Cell Surface Receptors and Intracellular Signaling," Invest. Ophthalmol. Vis. Sci. 47(6):2430-2437 (2006).

Doherty et al., "Site-Specific PEGylation of Engineered Cysteine Analogues of Recombinant Human Granulocyte-Macrophage Colony-Stimulating Factor," Bioconjug. Chem. 16(5):1291-1298 (2005).

Dougherty et al., "Corneoscleral Melt after Pterygium Surgery Using A Single Intraoperative Application of Mitomycin-C," Cornea 15(5):537-540 (1996).

Ecker et al. "Rational Screening of Oligonucleotide Combinatorial Libraries for Drug Discovery," Nucl. Acids Res. 21(8):1853 (1993).

Egan et al., "Fortimicins A and B, New Aminoglycoside Antibiotics. III. Structural Identification," J. Antibiot. (Tokyo) 30(7):552-563 (1977).

Eichler et al., "Generation and Utilization of Synthetic Combinatorial Libraries," Mol. Med. Today 1(4):174-180 (1995).

Eichler et al., "Antineovascular Agents in the Treat of Eye Diseases," Curr. Pharm. Des. 12(21):2645-2660 (2006).

Eljarrat-Binstock et al., "Iontophoresis: A Non-Invasive Ocular Drug Delivery," J. Control. Release 110(3):479-489 (2006).

Ellington et al. "In Vitro Selection of RNA Molecules that Bind Specific Ligands," Nature 346(6287):818-822 (1990).

English et al., "Induction of Endothelial Cell Chemotaxis by Sphingosine-1-Phosphate and Stabilization of Endothelial Monolayer Barrier Function by Lysophosphatidic Acid, Potential Mediators of Hematopoietic Angiogenesis," J. Hematother. Stem Cell Res. 8(6):627-634 (1999).

English et al., "Sphingosine 1-Phosphate Released from Platelets during Clotting Accounts for the Potent Endothelial Cell Chemotactic Activity of Blood Serum and Provides a Novel Link between Hemostasis and Angiogenesis," FASEB J. 14(14):2255-2265 (2000).

Eppstein et al., "Biological activity of liposome-encapsulated murine interferon γ is mediated by a cell membrane receptor," Proc. Natl. Acad. Sci. USA 82(11):3688-3692 (1985).

Erber et al., "Combined Inhibition of VEGF- and PDGF-Signaling Enforces Tumor Vessel Regression by Interfering with Pericytemediated Endothelial Cell Survival Mechanisms," FASEB J. 18(2):338-340 (2004).

Espinosa-Heidmann et al., "Macrophage Depletion Diminishes Lesion Size and Severity in Experimental Choroidal Neovascularization," Invest. Ophthalmol. Vis. Sci. 44(8):3586-3592 (2003).

Felinski et al., "Glucocorticoid Regulation of Endothelial Cell Tight Junction Gene Expression: Novel Treatments for Diabetic Retinopathy," Curr. Eye Res. 30(11):949-957 (2005).

Fini, "Keratocyte and Fibroblast Phenotypes in the Repairing Cornea," Prog. Retin. Eye Res. 8(4):529-551 (1999).

Fitzgerald et al., "3,4-Dihydroxybenzylamine: An Improved Dopamine Analog Cytotoxic for Melanoma Cells in part through Oxidation Products Inhibitory to DNA pPolymerase," J. Invest. Dermatol. 80(2):119-123 (1983).

Folger et al., "Transforming Growth Factor—b-Stimulated Connective Tissue Growth Factor Expression during Corneal Myofibroblast Differentiation," Invest. Ophthalmol. Vis. Sci. 42(11):2534-2541 (2001).

Fontana et al., "Trabeculectomy with Mitomycin C: Outcomes and Risk Factors for Failure in Phakic Open-Angle Glaucoma," Ophthalmology 113(6):930-936 (2006).

Foote et al., "Antibody Framework Residues Affecting the Conformation of the Hypervariable Loops," J. Mol. Biol. 224(2):487-499 (1992).

Forrester, "Macrophages Eyed in Macular Degeneration," Nat. Med. 9(11):1350-1351 (2003).

French et al., "Discovery and Evaluation of Inhibitors of Human Sphingosine Kinase," Cancer Res. 63(18): 5962-5969 (2003).

Fujino et al., "Amelioration of Experimental Autoimmune Encephalomyelitis in Lewis Rats by FTY720 Treatment," J. Pharmacol. Exp. Ther. 305(1):70-77 (2003).

Fujiwara et al., "Production of a New Aminoglycoside Antibiotic by a Mutant of *Bacillus circulans*," J. Antibiot. (Tokyo) 33(8):836-841 (1980).

Fujiwara et al., "Identification of Residues Responsible for Ligand Recognition and Regioisomeric Selectivity of Lysophosphatidic Acid Receptors Expressed in Mammalian Cells," J. Biol. Chem. 280(41):35038-35050 (2005).

Ganguly, "Ziracin, A Novel Oligosaccharide Antibiotic," J. Antibiot. (Tokyo) 53(10):1038-1044 (2000).

Gao et al., "The Wt1+-R394W Mouse Displays Glomerulosclerosis and Early-Onset Renal Failure Characteristic of Human Denys-Drash Syndrome," Mol. Cell. Biol. 24(22):9899-9910 (2004).

Gardell et al., "Emerging medicinal roles for lysophospholipid signaling," Trends Mol. Med. 12(2):65-75 (2006).

Gariano et al., "Retinal Angiogenesis in Development and Disease," Nature 438(7070):960-966 (2005).

Gavilondo et al., "Antibody Engineering at the Millennium," BioTechniques, 29(1):128-145 (2000).

Gerhardt et al., "Endothelial-Pericyte Interactions in Angiogenesis," Cell Tissue Res. 314(1):15-23 (2003).

Goetzl et al., "An IgM-kappa rat monoclonal antibody specific for the type 1 sphingosine 1-phosphate G protein-coupled receptor with antagonist and agonist activities," Immonol. Lett. 93(1):63-69 (2004).

Goetzl et al., "Regulation of immunity by lysosphingolipids and their G protein-coupled receptors," J. Clin. Invest. 114(11):1531-1537 (2004).

Gorin et al., "The Genetics of Age-Related Macular Degeneration," Mol. Vis. 5:29-34 (1999).

Gragoudas et al., "Pegaptanib for Neovascular Age-Related Macular Degeneration," New Eng. J. Med. 351(27):2805-2816 (2004).

Graham et al., "Characteristics of a Human Cell Line Transformed by DNA from Human Adenovirus Type 5," J. Gen Virol. 36(1):59-72 (1977).

Grines et al., "A Comparison of Immediate Angioplasty with Thrombolytic Therapy for Acute Myocardial Infarction," New Eng. J. Med. 328(10):673-679 (1993).

Grosskreutz et al., "Vascular Endothelial Growth Factor-Induced Migration of Vascular Smooth Muscle Cells in Vitro," Microvasc. Res. 58(2):128-136 (1999).

Grossniklaus et al., "Clinicopathologic Features of Surgically Excised Choroidal Neovascular Membranes," Ophthalmology 101(6):1099-1111 (1994).

Grossniklaus et al., "Macrophage and Retinal Pigment Epithelium Expression of Angiogenic Cytokines in Choroidal Neovascularization," Mol. Vis. 8:119-126 (2002).

Gruber et al., "Efficient tumor cell lysis mediated by a bispecific single chain antibody expressed in *Escherichia coli*," J. Immunol. 152(11):5368-5374 (1994).

Gryziewicz, "Regulatory Aspects of Drug Approval for Macular Degeneration," Adv. Drug Deliv. Rev. 57:2092-2098 (2005).

Gu et al., "In Vitro Activity of Dactimicin, a Novel Pseudodisaccharide Aminoglycoside, Compared with Activities of other Aminoglycosides," Antimicrob. Agents Chemother. 33(11):1998-2003 (1989).

Guillon et al., "Disruption of the Gene for Met-tRNA(fMet) Formyltransferase Severely Impairs Growth of *Escherichia coli*," J. Bacteriol. 174(13):4294-4301 (1992).

Guo et al., "Platelet-Derived Growth Factor-B Enhances Glioma Angiogenesis by Stimulating Vascular Endothelial Growth Factor Expression in Tumor Endothelia and by Promoting Pericyte Recruitment," Am. J. Pathol. 162(4):1083-1093 (2003).

Guss et al., "Structure of the IgG-binding regions of streptococcal protein G," EMBO J. 5(7):1567-1575 (1986).

Hageman et al., "A Common Haplotype in the Complement Regulatory Gene Factor H (HF1_CFH) Predisposes Individuals to Age-Related Macular Degeneration," Proc. Natl. Acad. Sci. USA 102(20):7227-7232 (2005).

Haimovitz-Friedman et al., "Ionizing Radiation Acts on Cellular Membranes to Generate Ceramide and Initiate Apoptosis," J. Exp. Med. 180(2):525-535 (1994).

Hajjar et al., "Prospects for Gene Therapy for Heart Failure," Circ. Res. 86(6):616-621 (2000).

Ham et al., "Media and Grown Requirements," Methods Enzmol. 58:44-93 (1979).

Hama et al., "Lysophosphatidic Acid and Autotaxin Stimulate Cell Motility of Neoplastic and Non-neoplastic Cells through LPA," J. Biol. Chem. 279(17):17634-17639 (2004).

Hammer et al., "Glucocorticoids Mediate Differential Anti-Apoptotic Effects in Human Fibroblasts and Keratinocytes via Sphingosine-1-Phosphate Formation," J. Cell. Biochem. 91(4):840-851 (2004).

Hanessian et al., "Aminoglycoside Antibiotics: Oxidative Degradations Leading to Novel Biochemical Probes and Synthetic Intermediates," J. Antibiot. (Tokyo) 28(10):835-837 (1975).

Hanselman et al., "A cDNA-Dependent Scintillation Proximity Assay for Quantifying Apolipoprotein A-I," J. Lipid Res. 38(11):2365-2373 (1997).

Harada et al., "The Role of Cytokines and Trophic Factors in Epiretinal Membranes: Involvement of Signal Transduction in Glial Cells," Prog. Retin. Eye Res. 25(2):149-164 (2006).

Harris et al., "Effect of Pegylation on Pharmaceuticals," Nat. Rev. Drug Disc. 2(3):214-221 (2003).

Hashimoto et al., "Lysophosphatidic Acid (LPA) Induces Plasma Exudation and Histamine Release in Mice via LPA Receptors," J. Pharmacol. Sci. 100(1):82-87 (2006).

Hayashi et al., "Phenotypic Modulation of Vascular Smooth Muscle Cells Induced by Unsaturated Lysophosphatidic Acids," Circ. Res. 89(3):251-258 (2001).

Hegde et al., "CD4+ T-Cell-Mediated Mechanisms of Corneal Allograft Rejection: Role of Fas-Induced Apoptosis," Transplantation 79(1):23-31 (2005).

Heim et al., "Engineering Green Fluorescent Protein for Improved Brightness, Longer Wavelengths and Fluorescence Resonance Energy Transfer," Curr. Biol. 6(2):178-182 (1996).

Heymans et al., "Loss or Inhibition of uPA or MMP-9 Attenuates LV Remodeling and Dysfunction after Acute Pressure Overload in Mice," Am. J. Pathol. 166(1):15-25 (2005).

Hla, "Physiological and Pathological Actions of Sphingosine 1-Phosphate," Semin. Cell Dev. Biol. 15(5):513-520 (2004).

Hobbs Dewitt et al., "'Diversomers': An Approach to Nonpeptide, Nonoligomeric Chemical Diversity," Proc. Nat. Acad. Sci. USA 90(15):6909-6913 (1993).

Hochlowski et al., "Phenelfamycins, A Novel Complex of Elfamycin-Type Antibiotics. II. Isolation and Structure Determination," J. Antibiot. (Tokyo) 41(10):1300-1315 (1988).

Hollinger et al., "'Diabodies:' Small bivalent and bispecific antibody fragments," Proc. Natl. Acad. Sci. USA 90(14):6444-6448 (1993).

Holmes et al., "Scar Remodeling and Transmural Deformation after Infarction in the Pig," Circulation 90(1):411-420 (1994).

Hoogenboom et al., "By-passing immunisation. Human antibodies from synthetic repertoires of germline VH gene segments rearranged in vitro," J. Mol. Biol. 227(2):381-388 (1991).

Horkko et al. "Antiphospholipid Antibodies are Directed against Epitopes of Oxidized Phospholipids. Recognition of Cardiolipin by Monoclonal Antibodies to Epitopes of Oxidized low density Lipoprotein," J. Clin. Invest. 98(3):815-825 (1996).

Hotta et al., "The Novel Enzymatic 3'-N-Acetylation of Arbekacin by an Aminoglycoside 3-N-Acetyltransferase of Streptomyces Origin and the Resulting Activity," J. Antibiot. (Tokyo) 51(8):735-742 (1998).

Hueber et al., "Basic Fibroblast Growth Factor mRNA, bFGF Peptide and FGF Receptor in Epiretinal Membranes of Intraocular Proliferative Disorders (PVR and PDR)," Int. Ophthalmol. 20(6):345-350 (1996).

Hughes et al., "Characterization of Smooth Muscle Cell and Pericyte Differentiation in the Rat Retina in Vivo," Investigat. Ophthalmol. Vis. Sci. 45(8):2795-2806 (2004).

Hwang et al., "Hepatic uptake and degradation of unilamellar sphingomyelin-cholesterol liposomes: A kinetic study," Proc. Natl. Acad. Sci. USA 77(7):4030-4034 (1980).

Igarashi et al., "Sphingosine 1-Phosphate and Isoform-specific Activation of Phosphoinositide 3-Kinase Beta," J. Biol. Chem. 276(39):36281-36288 (2001).

Igarashi et al., "VEGF Induces S1P1 Receptors in Endothelial Cells: Implications for Cross-Talk between Sphingolipid and Growth Factor Receptors," Proc. Natl. Acad. Sci. USA 100(19):10664-10669 (2003).

Ikeda et al., "Biological Activities of novel Lipid Mediator Sphingosine 1-Phosphate in Rat Hepatic Stellate Cells," Am J. Physiol. Gastrointest. Liver Physiol. 279(2):G304-G310 (2000).

Ing et al., "Ten-year Postoperative Results of Penetrating Keratoplasty," Ophthalmology 105(10):1855-1865 (1998).

Inouye et al., "A Novel Aminoglycoside Antibiotic, Substance SF-2052," J. Antibiot. (Tokyo) 32(12):1354-1356 (1979).

Ishibashi et al., "Pericytes of Newly Formed Vessels in Experimental Subretinal Neovascularization," Arch. Ophthalmol. 113(2):227-231 (1995).

Isobe et al., "Early Detection of Rejection and Assessment of Cyclosporine Therapy by 111In Antimyosin Imaging in Mouse Heart Allografts," Circulation 84(3):1246-1255 (1991).

Jackson et al., "Phenelfamycins, a Novel Complex of Elfamycin-type Antibiotics. I. Discovery, Taxonomy and Fermentation," J. Antibiot. (Tokyo) 41(10):1293-1299 (1988).

Jackson et al., "Altromycins, Novel Pluramycin-like Antibiotics. I. Taxonomy of the Producing Organism, Fermentation and Antibacterial Activity," J. Antibiot. (Tokyo) 43(3):223-228 (1990).

Jakobovits et al., "Germ-line transmission and expression of a human-derived yeast artificial-chromosome," Nature 362(6417):255-258(1993).

Jakobovits et al., "Analysis of homozygous mutant chimeric mice:Deletion of the immunoglobulin heavy-chain joining region blocks B-cell development and antibody production," Proc. Natl. Acad. Sci. USA 90(6):2551-2555 (1993).

Janda, "Tagged Versus Untagged Libraries: Methods for the Generation and Screening of Combinatorial Chemical Libraries," Proc. Natl. Acad. Sci. USA 91(23):10779-10785 (1994).

Janeway et al., Immunobiology, Fifth Edition, Garland Publishing (2001) (Electronic Table of Contents Only).

Jerdan et al., "Proliferative Vitreoretinopathy Membranes," Ophthalmology 96(6):801-810 (1989).

Jester et al., "Modulation of Cultured Corneal Keratocyte Phenotype by Growth Factors—Cytokines Control in Vitro Contractility and Extracellular Matrix Contraction," Exp. Eye Res. 77(5):581-592 (2003).

Johnson et al., "A Potential Role for Immune Complex Pathogenesis in Drusen Formation," Exp. Eye Res. 70(4):441-449 (2000) 43(3):223-228 (1990).

Jolly et al., "Transactivation of Sphingosine-1-Phosphate Receptors by Fc RI Triggering Is Required for Normal Mast Cell Degranulation and Chemotaxis," J. Exp. Med. 199(7):959-970 (2004).

Jolly et al, "Expression of SphK1 Impairs Degranulation and Motility of RBL-2H3 Mast Cells by Desensitizing S1P Receptors," Blood 105(12):4736-4742 (2005).

Jones et al., "Replacing the complementarity-determining regions in a human antibody with those from a mouse," Nature 321(6069):522-525 (1986).

Jones et al., "Pathological CNS Autoimmune Disease Triggered by Traumatic Spinal Cord Injury: Implications for Autoimmune Vaccine Therapy," J. Neurosci. 22(7):2690-2700 (2002).

Joosten et al., "Antibody Response Against Perlecan and Collagen Types IV and VI in Chronic Renal Allograft Rejection in the Rat," Am. J. Pathol. 160(4):1301-1310 (2002).

Jordan et al., "The Role of Neutrophils in Myocardial Ischemia-Reperfusion Injury," Cardiovasc. Res. 43(4):860-878 (1999).

Joussen et al., "Suppression of Fas-FasL-Induced Endothelial Cell Apoptosis Prevents Diabetic Blood—Retinal Barrier Breakdown in a Model of Streptozotocin-Induced Diabetes," FASEB J. 17(1):76-78 (2003).

Kabat, "Antibody Diversity Versus Antibody Complementarity," Pharmacol. Rev. 34(1):23-38 (1982).

Kang et al., "Serum Bioactive Lysophospholipids Prevent Trail-Induced Apoptosis Via PI3K-Akt-Dependent cFLIP Expression and Bad Phosphorylation," Cell Death Differ 11(12):1287-1298 (2004).

Kappos et al., "Oral Fingolimod (FTY720) for Relapsing Multiple Sclerosis," New Eng. J. Med. 355(11):1124-1140 (2006).
Kaur et al., "Ocular Preparations: The Formulation Approach," Drug Dev. Ind. Pharm. 28(5):473-493 (2002).
Kawasaki et al., "Conjunctival Inflammation in the Chronic Phase of Stevens-Johnson Syndrome," Br. J. Ophthalmol. 84(10):1191-1193 (2000).
Kent et al., "Choroidal Neovascularization: A Wound Healing Perspective," Mol.Vis. 9:747-755 (2003).
Khachigan, "Early growth response-1 in cardiovascular pathobiology," Circ. Res. 98(2):186-191 (2006).
Kim et al., "Identification of Sphingomyelin Turnover as an Effector Mechanism for the Action of Tumor Necrosis Factor alpha and gamma-Interferon. Specific role in cell differentiation," J. Biol. Chem. 266(1):484-489 (1991).
Kimura et al., "Reciprocal Regulation between Nitric Oxide and Vascular Endothelial Growth Factor in Angiogenesis," Acta Biochim. Pol. 50(1):49-59 (2003).
Kinumaki et al., "Macrolide Antibiotics M-4365 produced by Micromonospora. II. Chemical Structures," J. Antibiot. (Tokyo) 30(6):450-454 (1977).
Kinzler et al., "Whole Genome PCR: Application to the Identification of Sequences bound by Gene Regulatory Protein," Nucl. Acids Res. 17(10):3645-3653 (1989).
Klein et al., "Complement Factor H Polymorphism in Age-Related Macular Degeneration," Science 308(5720):385-389 (2005).
Kohler et al., "Continuous Cultures of Fused Cells Secreting Antibody of Predefined Specificity," Nature 256(5517):495-497 (1975).
Kostelny et al., "Formation of a bispecific antibody by the use of leucine zippers," J. Immunol. 148(5):1547-1553 (1992).
Kozbor et al., "A human hybrid myeloma for production of human monoclonal antibodies," J. Immunol. 133(6):3001-3005 (1984).
Krag et al., "Excimer Laser Treatment of Pterygium," Acta Ophthalmol. (Copenh) 70(4):530-533 (1992).
Kria et al., "Growth Factors in Cultured Pterygium Fibroblasts: Immunohistochemical and ELISA analysis," Graefes Arch. Clin. Exp. Ophthalmol. 236(9):702-708 (1998).
Krown et al. "TNFα receptor Expression in Rat Cardiac Myocytes: TNFα Inhibition of L-type Ca2+ Current and Ca2+ Transients," FEBS Lett. 376(1-2):24-30 (1995).
Kugelman et al., "Letter: The Preparation of Garamine, a Novel Pseudodisaccharide from Sisomycin," J. Antibiot. (Tokyo) 26(7):394-395 (1973).
Kurian et al., "Retroviral vectors," J. Clin. Mol. Pathol. 53(4):173-176 (2000).
Kwon et al., "Sphingosine 1-Phosphate Protects Human Umbilical Vein Endothelial Cells from Serum-deprived Apoptosis by Nitric Oxide Production," J. Biol. Chem. 6(14):10627-10633 (2001).
La Cour et al., "Age-Related Macular Degeneration: Epidemiology and Optimal Treatment," Drugs Aging 19(2):101-133 (2002).
La Heij et al., "Basic Fibroblast Growth Factor, Glutamine Synthetase, and Interleukin-6 in Vitreous Fluid From Eyes With Retinal Detachment Complicated by Proliferative Vitreoretinopathy," Am. J. Ophthalmol. 134(3):367-375 (2002).
Lagerqvist et al., "Lower Threshold for Adenosine-Induced Chest Pain in Patients with Angina and Normal Coronary Angiograms," British Heart J. 68(9):282-285 (1992).
Lam et al., "Production and Isolation of Two Novel Esperamicins in a Chemically defined Medium," J. Antibiot. (Tokyo) 48(12):1497-1501 (1995).
Lamontagne et al., "Antagonism of Sphingosine-1-Phosphate Receptors by FTY720 Inhibits Angiogenesis and Tumor Vascularization," Cancer Res. 66(1):221-231 (2006).
Lee et al., "Sphingosine 1-Phosphate Induces Angiogenesis: Its Angiogenic Action and Signaling Mechanism in Human Umbilical Vein Endothelial Cells," Biochem. Biophys Res. Comm. 264(3):743-750 (1999).
Lee et al., "Vascular Endothelial Cell Adherens Junction Assembly and Morphogenesis Induced by Sphingosine-1-Phosphate," Cell 99(3):301-312 (1999).
Lee et al., "Akt-Mediated Phosphorylation of the G Protein-Coupled Receptor EDG-1Is Required for Endothelial Cell Chemotaxis," Mol. Cell 8(3):693-704 (2001).

Lee et al., "Lysophosphatidic Acid Is a Major Regulator of Growth-Regulated Oncogene-alpha in Ovarian Cancer," Cancer Res. 66(5):2740-2748 (2006).
Levade et al., "Sphingolipid Mediators in Cardiovascular Cell Biology and Pathology," Circ. Res. 89(11):957-968 (2001).
Li et al., "Nonviral Gene Therapy: Promises and Challenges," Gene Ther. 7(1):31-34 (2000).
Liang et al., "Parallel Synthesis ans Screening of a Solid Phase Carbohydrate Library," Science 274(5292):1520-1522 (1996).
Liliom et al., "Growth Factor-Like Phospholipids Generated after Corneal Injury," Am. J. Physiol. 274(4):C1065-C1074 (1998).
Limaye et al., "Sphingosine Kinase-1 Enhances Endothelial Cell Survival through a PECAM-1-Dependent Activation of PI-3K-Akt and Regulation of Bcl-2 Family Members," Blood 105(8):3169-3177 (2005).
Lindahl et al., "Pericyte Loss and Microaneurysm Formation in PDGF-B-Deficient Mice," Science 277(5323):242-245 (1997).
Lindmark et al., "Binding of immunoglobulins to protein A and immunoglobulin levels in mammalian sera," J. Immunol. Meth. 62(1):1-13 (1983).
Lingen, "Role of Leukocytes and Endothelial Cells in the Development of Angiogenesis in Inflammation and Wound Healing," Arch. Pathol. Lab Med. 125(1):67-71 (2001).
Liu et al., "A Review of Treatments for Macular Degeneration: A Synopsis of Currently Approved Treatments and Ongoing Clinical Trials," Curr. Opin. Ophthalmol. 15(3):221-226 (2004).
Long et al., "The Functional PDGFB Receptor—S1P1 Receptor Signaling Complex is Involved in Regulating Migration of Mouse Embryonic Fibroblasts in Response to Platelet Derived Growth Factor," Prostaglandins. Other Lipid Med. 80(1-2):74-80 (2006).
Lowe et al., "Sphingosine Differentially Inhibits Activation of the Na+-H+exchange by Phorbol Esters and Growth Factors," J. Biol. Chem. 265(13):7188-7194 (1990).
Luberto et al., "Inhibition of Tumor Necrosis Factor-induced Cell Death in MCF7 by a Novel Inhibitor of Neutral Sphingomyelinase," J. Biol. Chem. 277(43):41128-41139 (2002).
Macaya et al., "Thrombin-Binding DNA Aptamer forms a Unimolecular Quadruplex Structure in Solution," Proc. Natl Acad. Sci. USA 90(8):3745-3749 (1993).
MacDonnell et al., "Depression of Excitability by Sphingosine 1-Phosphate in Rat Ventricular Myocytes," Am. J. Physiol.Heart Circ. Physiol. 275(6):H2291-H2299 (1998).
Marchini et al., "4-Demethoxy-3'-Deamino-3'-Aziridinyl-4'-Methylsulphonyl-Daunorubicin (PNU-159548), a Novel Anticancer Agent Active Against Tumor Cell Lines with Different Resistance Mechanisms," Cancer Res. 61(5):1991-1995 (2001).
Marcovich et al., "Angiogenesis in Pterygium: Morphometric and Immunohistochemical Study," Curr. Eye Res. 25(1):17-22 (2002).
Marks et al., "By-passing Immunization Human Antibodies from V-gene Libraries Displayed on Phage," J. Mol. Biol. 222(3):581-597 (1991).
Martin et al., "Irreversible Coupling of Immunoglobulin Fragments to Preformed Vesicles: An Improved Method for Liposome Targeting,"J. Biol. Chem. 257(1):286-288 (1982).
Martin et al., "Iontophoresis of Lysophosphatidic Acid into Rabbit Cornea Induces HSV-1 Reactivation: Evidence that Neuronal Signaling Changes after Infection," Mol. Vis. 5:36-42 (1999).
Massberg et al.,"Fingolimod and Sphingosine-1-Phosphate—Modifiers of Lymphocyte Migration," New Eng. J. Med. 355(11):1088-1091 (2006).
Mather, "Establishment and Characterization of Two Distinct Mouse Testicular Epithelial Cell Lines," Biol. Reprod. 23(1):243-252 (1980).
Matsuhashi et al., "In Vitro and in Vivo Antibacterial Activities of Dactimicin, a Novel Pseudodisaccharide Aminoglycoside, Compared with those of other Aminoglycoside Antibiotics," Antimicrob. Agents Chemother. 27(4):589-594 (1985).
Matsumoto et al., "Synthesis of Novel 13-Methyl-13-Dihydroanthracyclines," Chem. Pharm. Bull. (Tokyo) 34(11):4613-4619 (1986).
Matsunaga et al., "Bacterial Uptake of Habekacin, a Novel Aminoglycoside Antibiotic," J. Antibiot. (Tokyo) 37(5):596-601 (1984).

Matsuura et al., "Effect of FTY720, A Novel Immunosuppressant, on Adjuvant- and Collagen-Induced Arthritis in Rats," Int. J. Immunopharmacol. 22(4):323-331 (2000).

McCormick, "Anti-TGF-β Treatment Prevents Skin and Lung Fibrosis in Murine Sclerodermatous Graft-Versus-Host Disease: A Model for Human Scleroderma," J. Immunol. 163(10):5693-5699 (1999).

McDonough et al. "Control of Cardiac Ca2+ levels: Inhibitory Actions of Sphingosine on Ca2+ Transients and L-type Ca2+ Channel Conductance," Circ. Res. 75(6):981-989 (1994).

Meldrum et al., "Increased Myocardial Tumor Necrosis Factor- in a Crystalloid-Perfused Model of Cardiac Ischemia-Reperfusion Injury," Ann. Thorac. Surg. 65(2):439-443 (1998).

Merrifield, "Solid Phase Peptide Synthesis. I. The Synthesis of a Tetrapeptidem," J. Am. Chem. Soc. 85(14):2149-2154 (1964).

Miller et al., "Clinical Pharmacology and Toxicity of 4'-O-Tetrahydropyranyladriamycin," Cancer Res. 47(5):1461-1465 (1987).

Milstien et al., "Targeting Sphingosine-1-Phosphate: A Novel Avenue for Cancer Therapeutics," Cancer Cell 9(3):148-150 (2006).

Monahan et al., "AAV Vectors: is Clinical Success on the Horizon?," Gene Ther. 7(1):24-30 (2000).

Moolenaar, "Bioactive Lysophospholipids and Their G Protein-Coupled Receptors," Exp. Cell Res. 253(1):230-238 (1999).

Moolenaar et al., "The Ins and Outs of Lysophosphatidic Acid Signaling," BioEssays 26(8):870-881 (2004).

Morea et al., "Antibody Modeling: Implications for Engineering and Design," Methods 20(3):267-279 (2000).

Morimoto et al., "Single-step purification of F(ab')2 fragments of mouse monoclonal antibodies (immunoglobulins G1) by hydrophobic interaction high-performance liquid chromatography using TSKgel Phenyl-5PW," J. Biochem. Biophys. Methods 24(1-2):107-117 (1992).

Morrison et al., "Chimeric Human Antibody Molecules: Mouse Antigen-Binding Domains with Human Constant Region Domains," Proc. Natl. Acad. Sci. USA 81(21):6851-6855 (1984).

Moulin, "The Clinical Management of Neoropathic Pain," Pain Res. Manag. 11(Suppl A):30A-36A (2006).

Munson et al., "Ligand: A versatile computerized approach for characterization of ligand-binding systems," Anal. Biochem. 107(1):220-239 (1980).

Murali-Krishna et al., "Counting Antigen-Specific CD8 T Cells: A Reevaluation of Bystander Activation during Viral Infection," Immunity 8(2):177-187 (1998).

Mutsch et al., "Success Criteria and Success Rates in Trabeculectomy with and without Intraoperative Antimetabolites using Intensified Postoperative Care (IPC)," Graefe Arch. Clin. Exp. Ophthalmol. 238(11):884-891 (2000).

Myles et al., "Recent Progress in Ocular Drug Delivery for Posterior Segment Disease: Emphasis on Transscleral Iontophoresis," Adv. Drug Deliv. Rev. 57(14):2063-2079 (2005).

Nagineni et al., "Expression of PDGF and Their Receptors in Human Retinal Pigment Epithelial Cells and Fibroblasts: Regulation by TGF-B" J. Cell. Physiol. 203(1):35-43 (2005).

Netto et al., "Wound Healing in the Cornea," Cornea 24(5):509-522 (2005).

Neuberger et al., "Recombinant antibodies possessing novel effector functions," Nature 312(5995):604-608 (1984).

Newton et al., "Formylation Is Not Essential for Initiation of Protein Synthesis in All Eubacteria," J. Biol. Chem. 274(32):22143-22146 (1999).

Nickenig et al., "Statin-Sensitive Dysregulated AT1 Receptor Function and Density in Hypercholesterolemic Men," Circulation 100(21):2131-2134 (1999).

Norata et al., "High-Density Lipoproteins Induce Transforming Growth Factor-β2 Expression in Endothelial Cells," Circulation 111(21):2805-2811 (2005).

O'Sullivan et al., "Methods for the Preparation of Enzyme-Antibody Conjugates for use in Enzyme Immunoassay," Methods Enzymol. 73(Pt. B):147-166 (1981).

Ogretmen et al., "Biologically active sphingolipids in cancer pathogenesis and treatment," Nat. Rev. Cancer 4(8):604-616 (2004).

Oh et al., "The Potential Angiogenic Role of Macrophages in the Formation of Choroidal Neovascular Membranes," Invest. Ophthalmol. Vis. Sci. 40(9):1891-1898 (1999).

Ohashi et al., "In Vitro and in Vivo Antibacterial Activity of KW1070, a New Aminoglycoside Antibiotic," Antimicrob. Agents Chemother. 17(2):138-143 (1980).

Okachi et al., "Fortimicins A and B, New Aminoglycoside Antibiotics. II. Isolation, Physico—Chemical and Chromatographic Properties," J. Antibiot. (Tokyo) 30(7):541-551 (1977).

Olivera et al., "Sphingosine Kinase Expression Increases Intracellular Sphingosine-1-Phosphate and Promotes Cell Growth and Survival," J. Cell Biol. 147(3):545-558 (1999).

Olivera, "Sphingolipids and the Balancing of Immune Cell Function: Lessons from the Mast Cell," J. Immunol. 174(3):1153-1158 (2005).

Otani et al., "Expressions of Angiopoietins and Tie2 in Human Choroidal Neovascular Membranes," Invest. Ophthalmol. Vis. Sci. 40(9):1912-1920 (1999).

Padmanabhan et al., "The Structure of a-Thrombin Inhibited by a 15-Mer Single-stranded DNA Aptamer," J. Biol. Chem. 268(24):17651-17654 (1993).

Paik et al., "Sphingosine 1-Phosphate Receptor Regulation of N-Cadherin Mediates Vascular Stabilization," Genes Dev. 18(19):2392-2403 (2004).

Palinski et al. "Cloning of Monoclonal Autoantibodies to Epitopes of Oxidized Lipoproteins from Apolipoprotein E-deficient Mice (Demonstration of Epitopes of Oxidized Low Density Lipoprotein in Human Plasma)," J. Clin. Invest, 98(3):800-814 (1996).

Parrill et al., "Identification of Edg1 Receptor Residues That Recognize Sphingosine 1-Phosphate," J. Biol. Chem. 275(50):39379-39384 (2000).

Pauleikhoff, "Neovascular Age-Related Macular Degeneration: Natural History and Treatment Outcomes," Retina 25(8):1065-1084 (2005).

Pelyvas et al., "Synthesis of New Pseudodisaccharide Aminoglycoside Antibiotics from Carbohydrates," J. Antibiot. (Tokyo) 48(7):683-695 (1995).

Perzynski et al., "Effects of Apramycin, A Novel Aminoglycoside Antibiotic on Bacterial Protein Synthesis," Eur. J. Biochem. 99(3):623-628 (1979).

Peters et al., "Selective Lymphocyte Inhibition by FTY720 slows the Progressive Course of Chronic Anti-Thy 1 Glomerulosclersis," Kidney Int. 66(4):1434-1443 (2004).

Phillipson et al., "Lanomycin and Glucolanomycin, Antifungal Agents Produced by Pycnidiophora dispersa. II. Structure Elucidation," J. Antibiot. (Tokyo) 45(3):313-319 (1992).

Planck et al., "Expression of Growth Factor mRNA in Rabbit PVR Model Systems," Curr. Eye Res. 11(11):1031-1039 (1992).

Ponder, "Systemic Gene Therapy for Cardiovascular Disease," Trends Cardiovasc. Med. 9(6):158-162 (1999).

Pournaras et al., "Myofibroblasts and Epiretinal Membranes," Klin. Monatsbl. Fur Augenheilkd. 212(5):356-358 (1998) (English Abstract Only).

Presta, "Antibody Engineering," Curr. Opin. Struct. Biol. 2(6):593-596 (1992).

Priebe et al., "3'-Hydroxyesorubicin. Synthesis and Antitumor Activity," J. Antibiot. (Tokyo) 43(7):838-846 (1990).

Pyne et al., "Sphingosine 1-Phosphate Signalling in Mammalian Cells," Biochem. J. 349(Pt. 2):385-402 (2000).

Queen et al., "A Humanized Antibody that Binds to the Interleukin 2 Receptor," Proc. Natl. Acad. Sci. USA 86(24):10029-10033 (1989).

Radeff-Huang et al., "G Protein Mediated Signaling Pathways in Lysophospholipid Induced Cell Proliferation and Survival," J. Cell. Biochem. 92(5):949-966 (2004).

Rao et al., "Expression of Nonphagocytic NADPH Oxidase System in the Ocular Lens," Mol. Vis. 10:112-121 (2004).

Razzaque et al., "Role of Macrophage Migration Inhibitory Factor in Conjunctival Pathology in Ocular Cicatricial Pemphigoid," Invest. Ophthalmol. Vis. Sci. 45(4):1174-1181 (2004).

Reza et al., "Anti-Idiotypic Monoclonal Antibody Recognizes a Consensus Recognition Site for Phosphatidylserine in Phosphatidylserine-Specific Monoclonal Antibody and Protein Kinase C," FEBS Lett. 339(3):229-233 (1994).

Rikitake et al., "Involvement of Endothelial Nitric Oxide in Sphingosine-1-Phosphate-Induced Angiogenesis," Arterioscler. Thromb. Vasc. Biol. 22(1):108-114 (2002).
Robaye et al., "Tumor necrosis factor induces apoptosis (programmed cell death) in normal endothelial cells in vitro," Am. J. Pathol. 138(2):447-453 (1991).
Robbins et al., "Platelet-Derived Growth Factor Ligands and Receptors Immunolocalized in Proliferative Retinal Diseases," Invest. Ophthalmol. Vis. Sci. 35(10):3649-3663 (1994).
Rosen et al., "Sphingosine 1-Phosphate and its Receptors: An Autocrine and Paracrine Network," Nat. Rev. Immunol. 5(7):560-570 (2005).
Rosenfeld et al., "Ranibizumab for Neovascular Age-Related Macular Degeneration," New Eng.J. Med. 355(14):1419-1431 (2006).
Saika et al., "Loss of Tumor Necrosis Factor α Potentiates Transforming Growth Factor B-mediated Pathogenic Tissue Response during Wound Healing," Am. J. Pathol. 168(6):1848-1860 (2006).
Saishin et al., "VEGF-TRAPR1R2 Suppresses Choroidal Neovascularization and VEGF-Induced Breakdown of the Blood-Retinal Barrier," J. Cell. Physiol. 195(2):241-248 (2003).
Saitoh et al., "Boholmycin, A New Aminoglycoside Antibiotic. I. Production, Isolation and Properties," J. Antibiot. (Tokyo) 41(7):855-861 (1988).
Sanchez et al., "Phosphorylation and Action of the Immunomodulator FTY720 Inhibits Vascular Endothelial Cell Growth Fctor-induced Vascular Permeability," J. Biol. Chem. 278(47):47281-47290 (2003).
Scherer et al., "Sphingosine-1-phosphate modulates spiral modiolar artery tone: A potential role in vascular-based inner ear pathologies?," Cardiovasc. Res. 70(1):79-87 (2006).
Schnitzer et al., "Segmental Differentiation of Permeability, Protein Glycosylation, and Morphology of Cultured Bovine Lung Vascular Endothelium," Biochem. Biophys. Res. Comm. 199(1):11-19 (1994).
Schottenfeld et al., "Chronic Inflammation: A Common and Important Factor in the Pathogenesis of Neoplasia," CA Cancer J. Clin. 56(2):69-83 (2006).
Schwab et al., "Lymphocyte Sequestration Through S1P Lyase Inhibition and Disruption of S1P Gradients," Science 309(5741):1735-1739 (2005).
Seddon et al., "The Epidemiology of Age-Related Macular Degeneration," Int. Ophthalmol. Clin. 44(4):17-39 (2004).
Sedlakova et al., "FTY720 in Corneal Concordant Xenotransplantation," Transplantation 79(3):297-303 (2005).
Ségui et al., "Involvement of FAN in TNF-induced apoptosis," J. Clin. Invest. 108(1):143-151 (2001).
Sena-Esteves et al., "HSV-1 Amplicon Vectors—Simplicity and Versatility," Mol. Ther. 2(1):9-15 (2000).
Shalaby et al., "Development of Humanized Bispecific Antibodies Reactive with Cytotoxic Lymphocytes and Tumor Cells Overexpressing the HER2 Protooncogene," J. Exp. Med. 175(1):217-225 (1992).
Shaunak et al., "Site-Specific PEGylation of Native Disulfide Bonds in Therapeutic Proteins," Nat. Chem. Biol. 2(6):312-313 (2006).
Simon et al., "Peptoids: A Modular Approach to Drug Discovery," Proc. Natl. Acad. Sci. USA 89(20):9367-9371 (1992).
Simon et al., "Lysophosphatidic Acid Inhibits Adipocyte Differentiation via Lysophosphatidic Acid 1 Receptor-dependent Down-regulation of Peroxisome Proliferator-activated Receptor γ2," J. Biol. Chem. 280(15):14656-14662 (2005).
Sinnaeve et al., "Gene Therapy in the Cardiovascular System: An Update," Cardiovasc. Res. 44(3):498-506 (1999).
Sivalingam et al., "Basic Fibroblast Growth Factor Levels in the Vitreous of Patients with Proliferative Diabetic Retinopathy," Arch. Ophthalmol. 108(6):869-872 (1990).
Smith et al., "Purified Fumonisin B1 Decreases Cardiovascular Function but Does Not Alter Pulmonary Capillary Permeability in Swine," Toxicol. Sci. 56(1):240-249 (2000).
Sotozono et al., "Cytokine Expression in the Alkali-Burned Cornea," Curr. Eye Res. 16(7):670-676 (1997).
Spiegel et al., "Sphingosine-1-Phosphate as a Therapeutic Agent," Leukemia 16(9):1596-1602 (2002).

Spiegel et al. "Sphingosine-1-Phosphate an Enigmatic Signalling Lipid," Nat. Rev. Mol. Cell Biol. 4(5):397-407 (2003).
Squires et al., "Altered Fibroblast Function following Myocardial Infarction," J. Mol. Cell. Cardiol. 39(4):699-707 (2005).
Stavri et al., "Basic Fibroblast Growth Upregulates the Expression of Vascular Endothelial Growth Factor in Vascular Smooth Muscle Cells," Circulation 92(1):11-14 (1995).
Stephan et al., "Gene Therapy for Coronary Disease," Ann. Endocrinol. (Paris) 61(1):85-90 (2000) (English Abstract Only).
Stramer et al., "Molecular Mechanisms Controlling the Fibrotic Repair Phenotype in Cornea: Implications for Surgical Outcomes," Invest. Ophthalmol. Vis. Sci. 44(10):4237-4246 (2003).
Strom et al., "Effect of Ruboxistaurin on Blood-Retinal Barrier Permeability in Relation to Severity of Leakage in Diabetic Macular Edema," Invest. Ophthalmol. Vis. Sci. 46(10, (2005).
Su et al., "Sphingosine 1-Phosphate, a Novel Signaling Molecule, Stimulates DNA Binding Activity of AP-1 in Quiescent Swiss 3T3 Fibroblasts," J. Biol. Chem. 269(23):16512-1651, (1994).
Sun et al., "Angiotensin Converting Enzyme and Myofibroblasts during Tissue Repair in the Rat Heart," J. Mol. Cell. Cardiol. 28(5):851-858 (1996).
Sun et al., "Infarct Scar: A Dynamic Tissue," Cardiovasc. Res. 46(2):250-256 (2000).
Sunada et al., "Acetylation of Aminoglycoside Antibiotics with 6'-Methylamino Group, Istamycin B and Micronomicin, by a Novel Aminoglycoside 6'-Acetyltransferase of Actinomycete Origin," J. Antibiot. (Tokyo) 53(12):1416-1419 (2000).
Suomalainen et al., "Sphingosine-1-Phosphate Inhibits Nuclear Factor κB Activation and Germ Cell Apoptosis in the Human Testis Independently of Its Receptors," Am. J. Pathol. 166(3):773-781 (2005).
Suzuki et al., "Preparation and Some Microbiological Properties of Novel Kanamycin-Glucoside Derivatives," J. Antibiot. (Tokyo) 32(7):753-755 (1979).
Svetlov et al., "EDG receptors and hepatic Pathophysiology of LPA and S1P: EDG-ology of Liver Injury," Biochim. Biophys. Acta 1582(1-3):251-256 (2002).
Takahashi et al., "Production of Novel Antibiotic, Dopsisamine, by A New Subspecies of Nocardiopsis Mutabilis with Multiple Antibiotic Resistance," J. Antibiot. (Tokyo) 39(2):175-183 (1986).
Tanaka, "Effects of Habekacin, A Novel Aminoglycoside Antibiotic, on Experimental Corneal Ulceration due to *Pseudomonas aeruginosa*," J. Antibiot. (Tokyo) 34(7):892-897 (1981).
Tanaka et al., "Mechanism of Action of Habekacin, A Novel Amino Acid-Containing Aminoglycoside Antibiotic," Antimicrobi. Agents Chemoth. 24(5):797-802 (1983).
Tanimoto et al., "Transactivation of Vascular Endothelial Growth Factor (VEGF) Receptor Flk-1-KDR Is Involved in Sphingosine 1-Phosphate-stimulated Phosphorylation of Akt and Endothelial Nitric-oxide Synthase (eNOS)," J. Biol. Chem. 277(45):42997-43001 (2002).
Tezel et al., "Pathogenesis of Age-Related Macular Degeneration," Trends Mol. Med. 10(9):417-420 (2004).
Tomasek et al., "Myofibroblasts and Mechano-Regulation of Connective Tissue Remoldeling," Nat. Rev. Mol. Cell Biol. 3(5):349-363 (2002).
Tonnetti et al., "A Role for Neutral Sphingomyelinase-mediated Ceramide Production in T Cell Receptor-induced Apoptosis and Mitogen-activated Protein Kinase-mediated Signal Transduction," J. Exp. Med. 189(10):1581-1589 (1999).
Torre-Amione et al, "Expression and Functional Significance of Tumor Necrosis Factor Receptors in Human Myocardium," Circulation 92(6):1487-1493 (1995).
Trautmann et al, "Mast Cell Involvement in Normal Human Skin Wound Healing: Expression of Monocyte Chemoattractant Protein-1 is Correlated with Recruitment of Mast Cells which Synthesize Interleukin-4 in Vivo," J. Pathol. 190(1):100-106 (2000).
Trentham et al, "Autoimmunity to Type II Collagen an Experimental Model of Arthritis," J. Exp. Med. 146(3):857-868 (1977).
Treston et al., "Biochemical Characterization of Peptide Alpha-Amidation Enzyme Activities of Human Neuroendocrine Lung Cancer Cell Lines," Cell Growth Differ. 4(11):911-920 (1993).

Trono, "Lentiviral Vectors: Turning a Deadly Foe into a Therapeutic Agent," Gene Ther. 7(1):20-23 (2000).
Tsunakawa et al., "Inosamycin, A Complex of New Aminoglycoside Antibiotics. I. Production, Isolation and Properties," J. Antibiot. (Tokyo) 38(10):1302-1312 (1985).
Tsutsumi et al., "The Critical Role of Ocular-Infiltrating Macrophages in the Development of Choroidal Neovascularization," J. Leukoc. Biol. 74(1):25-32 (2003).
Tuerk et al., "Systematic Evolution of Ligands by Exponential Enrichment: RNA Ligands to Bacteriophage T4 DNA Polymerase," Science 249(4968):505-510 (1990).
Tutt et al., "Trispecific F(ab')3 derivatives that use cooperative signaling via the TCR-CD3 complex and CD2 to activate and redirect resting cytotoxic T cells," J. Immunol. 147(1):60-69 (1991).
Ueno et al., "Accelerated Wound Healing of Alkali-Burned Corneas in MRL Mice Is Associated with a Reduced Inflammatory Signature" Invest. Ophthalmol. Vis. Sci. 46(11):4097-4106 (2005).
Urata et al., "Sphingosine 1-Phosphate Induces A-Smooth Muscle Actin Expression in Lung Fibroblasts via Rho-kinase," Kobe J. Med. Sci. 51(1):17-27 (2005).
Urban et al., "Comparative In-Vitro Activity of SCH 27899, a Novel Everninomicin, and Vancomycin," J. Antimicrob. Chemother. 37(2):361-364 (1996).
Urlaub et al., "Isolation of Chinese hamster cell mutants deficient in dihydrofolate reductase activity," Proc. Natl. Acad. Sci. USA 77(7):4216-4220 (1980).
Usui et al., "Blood Lipid Mediator Sphingosine 1-Phosphate Potently Stimulates Platelet-derived Growth Factor-A and -B Chain Expression through S1P1-Gi-Ras-MAPK-dependent Induction of Krüppel-like Factor 5," J. Biol. Chem. 279(13):12300-12311 (2004).
Vadas et al., "Endothelial Adhesion Molecules in Atherogenesis A Concerto or a Solo?," Circ. Res. 79(6):1216-1217 (1996).
Van Brocklyn et al., "Dual Actions of Sphingosine-1-Phosphate: Extracellular through the Gi-coupled Receptor Edg-1 and Intracellular to Regulate Proliferation and Survival," J. Cell Biol. 142(1):229-240 (1998).
Van Craenenbroeck et al., "Episomal Vectors for Gene Expression in Mammalian Cells" Eur. J. Biochem. 267(18):5665-5678 (2000).
Van Leeuwen et al., "Lysophosphatidic Acid: Mitogen and Motility Factor," Biochem. Soc. Trans. 31(Pt 6):1209-1212 (2003).
Van Meeteren et al., "Autotaxin, a Secreted Lysophospholipase D, Is Essential for Blood Vessel Formation during Development," Mol. Cell Biol. 26(13):5015-5022 (2006).
Van Wijngaarden et al., "Inhibitors of Ocular Neovascularization: Promises and Potential Problems," J. Am. Med. Assoc. 293(12):1509-1513 (2005).
Vekich et al., "Tumorigenic and angiogenic effects of S1P mAb in multiple murine models of cancer," Proceedings of the American Associaton for Cancer Research Annual Meeting 46:557 (2005) (Abstract Only).
Verma et al., "Chemokines in Acute Anterior Unveitis," Curr. Eye Res. 16(12):1202-1208 (1997).
Vidinova et al., "Ultrastrukturelle Veränderungen in der Struktur epiretinaler Membranen bei PVR—Anspruch und Wirklichkeit [Alterations in the Structure of the Epiretinal Membranes in PVR—Assumptions and Reality]," Klin Monatsbl. Augenheilkd. 222(7):568-571 (2005) (English Abstract Only).
Vinores et al., "Experimental Models of Growth Factor-Mediated Angiogenesis and Blood-Retinal Barrier Breakdown," Gen. Pharmacol. 35(5):233-239 (2000).
Virag et al., "Myofibroblast and Endothelial Cell Proliferation during Murine Myocardial Infarct Repair," Am. J. Pathol. 163(6):2433-2440 (2003).
Visentin et al., "Validation of an anti-sphingosine-1-phosphate antibody as a potential therapeutic in reducing growth, invasion, and angiogenesis in multiple tumor lineages," Cancer Cell, 9(3):225-238 (2006).
Waitz et al., "Biological Activity of Sch 14342, an Aminoglycoside Antibiotic Coproduced in the Gentamicin Fermentation," Antimicrob. Agents Chemother. 2(6):464 (1972).

Wang et al., "Sphingosine-1-phosphate inhibits motility of human breast cancer cells independently of cell surface receptors," Cancer Res. 59(24):6185-6191 (1999).
Wang et al., "Sphingosine 1-Phosphate Stimulates Cell Migration through a Gi-coupled Cell Surface Receptor," J. Biol. Chem. 274(50):35343-35350 (1999).
Wang et al., "In Vivo Activity and Pharmacokinetics of Ziracin (SCH27899), a New Long-Acting Everninomicin Antibiotic, in a Murine Model of Penicillin-Susceptible or Pneumococcal Pneumonia," Antimicrob. Agents Chemother. 44(4):1010-1018 (2000).
Weinstein et al., "Antibiotic 6640, A New *Micromonospora*-Produced Aminoglycoside Antibiotic," J. Antibiot. (Tokyo) 23(11):551-554 (1970).
Wells, "Eek, a XenoMouse: Abgenix, Inc.," Chem. Biol. 7(8):R185-R186 (2000).
Witmer et al., "Vascular EndothelialGrowth Factors and Angiogenesis in Eye Disease," Prog. Retin. Eye Res. 22(1):1-29 (2003).
Wu et al., "Lysophospholipids Enhance Matrix Metalloproteinase-2 Expression in Human Endothelial Cells," Endocrinology 146(8):3387-3400 (2005).
Xia et al., "An oncogenic role of sphingosine kinase," Curr. Biol. 10(23):1527-1530 (2000).
Yamagami et al., "Early Ocular Chemokine Gene Expression and Leukocyte Infiltration after High-Risk Corneal Transplantation," Mol. Vis. 11:632-640 (2005).
Yamakage et al., "Selective Upregulation of Platelet-Derived Growth Factor α Receptors by Transforming Growth Factor β in Scleroderma Fibroblasts," J. Exp. Med. 175(5):1227-1234 (1995).
Yamamoto et al., "Vitrectomy for Diabetic Macular Edema: The Role of Posterior Vitreous Detachment and Epimacular Membrane," Am. J. Ophthalmol. 132(3):369-377 (2001).
Yamanaka et al., "Sphingosine Kinase 1 (SPHK1) Is Induced by Transforming Growth Factor- β and Mediates TIMP-1 Up-regulation," J. Biol. Chem. 279(52):53994-54001 (2004).
Yanaga et al., "Tumor necrosis factor α stimulates sphingomyelinase through the 55 kDa receptor in HL-60 cells," FEBS Lett. 314(3):297-300 (1992).
Yasuda et al., "Total Synthesis of 3-0-Demethylsporaricin A," J. Antibiot. (Tokyo) 38(11):1512-1525 (1985).
Yatomi et al., "Sphingosine 1-Phosphate as a Major Bioactive Lysophospholipid that is Released from Platelets and interacts with Endothelial Cells," Blood 96(10):3431-3438 (2000).
Zager et al., "Altered Ceramide and Sphingosine Expression during the Induction Phase of Ischemic Acute Renal Failure," Kidney Int. 52(1):60-70 (1997).
Zapata et al. "Engineering linear F(ab')2 fragments for efficient production in *Escherichia coli* and enhanced antiproliferative activity," Protein Eng. 8(10):1057-1062 (1995).
Zarbin, "Current Concepts in the Pathogenesis of Age-Related Macular Degeneration," Arch. Ophthalmol. 122(4):598-614 (2004).
Zhang et al., "Sphingosine-1-phosphate, a novel lipid, involved in cellular proliferation," J. Cell Biol. 114(1):155-167 (1991).
Zhang et al., "Editorial: Signaling, through the Sphingomyelin Pathway," Endocrinology 136(10):4157-4160 (1995).
Zhang et al., "Sphingosine 1-Phosphate Stimulates Fibronectin Matrix Assembly Through a Rho-Dependent Signal Pathway," Blood 93(9):2984-2990 (1999).
Zhang et al., "Significant Prolongation of Orthotopic Corneal-Graft Survival in FTY720-Treated Mice," Transplantation 76(10):1511-1513 (2003).
Zheng et al., "Platelet-derived Growth Factor Receptor Kinase Inhibitor AG1295 and Inhibition of Experimental Proliferative Vitreoretinopathy," Jpn. J. Ophthalmol 47(2):158-165 (2003).
Zhu et al., "Both Apolipoprotein E and Immune Deficiency Exacerbate Neointimal Hyperplasia After Vascular Injury in Mice," Arterioscler. Thromb. Vasc. Biol. 22(3):450-455 (2002).

* cited by examiner

COMPOSITIONS AND METHODS FOR THE TREATMENT AND PREVENTION OF HYPERPROLIFERATIVE DISEASES

RELATED APPLICATIONS

This application claims priority to, the benefit of, and incorporates by reference for all purposes the following patent-related documents, each in its entirety: U.S. provisional patent application Ser. No. 60/623,197, filed 28 Oct. 2004; U.S. provisional patent application Ser. No. 60/257, 926, filed 22 Dec. 2000; U.S. patent application Ser. No. 10/028,156, filed 21 Dec. 2001 (now U.S. Pat. No. 6,881, 546); and U.S. patent application Ser. No. 10/820,582, filed 7 Apr. 2004, of which this application is a continuation-in-part.

GOVERNMENT FUNDING

This invention was funded at least in part by SBIR grant numbers NIH/NCI R43 CA110298-01 and NIH/NCI R43 CA110298-02. As a result, the U.S. government may have certain rights therein.

TECHNICAL FIELD

The invention relates generally to the area of treatment and/or prevention of hyperproliferative diseases and disorders and, in particular, cancer and other pathologies characterized by excessive neovascularization. These useful results are achieved by the use of agents, and compositions that contain such agents that interfere with the production and/or biological activities of sphingolipids and their metabolites.

BACKGROUND OF THE INVENTION

1. Introduction

The following description includes information that may be useful in understanding the present invention. It is not an admission that any such information is prior art, or relevant, to the presently claimed inventions, or that any publication specifically or implicitly referenced is prior art.

2. Background

There are many known hyperproliferative disorders, in which cells of various tissues and organs exhibit aberrant patterns of growth, proliferation, migration, signaling, senescence, and death. While a number of treatments have been developed to address some of these diseases, many still remain largely untreatable with existing technologies, while in other cases, while treatments are available, they are frequently less than optimal and are seldom curative.

Cancer represents perhaps the most widely recognized class of hyperproliferative disorders. Cancers are a devastating class of diseases, and together, they have a mortality rate second only to cardiovascular disease. Many cancers are not fully understood on a molecular level. As a result, cancer is a major focus of research and development programs for both the United States government and pharmaceutical companies. The result has been an unprecedented R&D effort and the production of many valuable therapeutic agents to help in the fight against cancer.

Unfortunately the enormous amount of cancer research has not been enough to overcome the significant damage caused by cancer. There are still over one million new cases of cancer diagnosed annually and over five hundred thousand deaths in the United States alone. This is a dramatic demonstration that even though an enormous effort has been put forth to discover new therapeutics for cancer, effective therapeutic agents to combat the disease remain elusive.

Cancer is now primarily treated with one or a combination of three types of therapies, surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia. Radiation therapy involves the exposure of living tissue to ionizing radiation causing death or damage to the exposed cells. Side effects from radiation therapy may be acute and temporary, while others may be irreversible. Chemotherapy involves the disruption of cell replication or cell metabolism.

Further insult is that current therapeutic agents usually involve significant drawbacks for the patient in the form of toxicity and severe side effects. Therefore, many groups have recently begun to look for new approaches to fighting the war against cancer. These new so-called "innovative therapies" include gene therapy and therapeutic proteins such as monoclonal antibodies.

The first monoclonal used in the clinic for the treatment of cancer was Rituxan (rituximab) which was launched in 1997, and has demonstrated the utility of biospecific monoclonal antibodies as therapeutic agents. Thus, not surprisingly, sixteen other monoclonal antibodies have since been approved for use in the clinic, including six that are prescribed for cancer. The success of these products, as well as the reduced cost and time to develop monoclonal antibodies as compared with small molecules has made monoclonal antibody therapeutics the second largest category of drug candidates behind small molecules. Further, the exquisite specificity of antibodies as compared to small molecule therapeutics has proven to be a major advantage both in terms of efficacy and toxicity. For cancer alone there are currently more than 270 industry antibody R&D projects with more than 50 companies involved in developing new cancer antibody therapeutics. Consequently, monoclonal antibodies are poised to become a major player in the treatment of cancer and they are estimated to capture an increasing share of the cancer therapeutic market.

The identification of extracellular mediators that promote tumor growth and survival is a critical step in discovering therapeutic interventions that will reduce the morbidity and mortality of cancer. As described below, sphingosine-1-phosphate (S1P), a key component of sphingolipid signaling cascade, is considered to be a pleiotropic, tumorigenic growth factor. S1P promotes tumor growth by stimulating cell proliferation, cell survival, and metastasis. S1P also promotes tumor angiogenesis by supporting the migration and survival of endothelial cells as they form new vessels within tumors. Taken together, S1P initiates a proliferative, pro-angiogenic, and anti-apoptotic sequence of events contributing to cancer progression. Thus, therapies that modulate, and, in particular, reduce S1P levels in vivo will be effective in the treatment of cancer.

3. Definitions

Before describing the instant invention in detail, several terms used in the context of the present invention will be defined. In addition to these terms, others are defined elsewhere in the specification, as necessary. Unless otherwise expressly defined herein, terms of art used in this specification will have their art-recognized meanings.

An "anti-S1P molecule" refers to any molecule that interferes with S1P activity, particularly an S1P activity on cells that are, or are capable of, proliferating. Representative examples of such molecules include anti-S1P antibodies, fragments from anti-S1P antibodies capable of specifically interacting with S1P, and agents that comprising a first binding moiety and a second binding moiety, wherein one of the binding moieties is specifically reactive with S1P.

The term "chemotherapeutic agent" means anti-cancer and other anti-hyperproliferative agents. Put simply, a "chemotherapeutic agent" refers to a chemical intended to destroy cells and tissues. Such agents include, but are not limited to: (1) DNA damaging agents and agents that inhibit DNA synthesis: anthracyclines (doxorubicin, donorubicin, epirubicin), alkylating agents (Cyclophosphamide, Mitomycin C, chemical mustards), platinum derivatives (cisplatin, carboplatin, cis diamminedichloroplatinum), telomerase and topoisomerase inhibitors (Camptosar), (2) tubulin-depolymerizing agents: taxoids (paclitaxel, docetaxel, BAY 59-8862), (3) anti-metabolites: fluorinated pyrimidines (5-FU, capecitabine, 5-DFUR, gemcitabine), proteosome inhibitors (Velcade), methotrexates, (4) anti-angiogenics (Avastin, thalidomide), vascular disrupting agents (flavonoids/flavones, DMXAA), combretastatin derivatives (CA4DP, ZD6126, AVE8062A), (5) biologics such as antibodies (Herceptin, Avastin, Panorex, Rituxin, Zevalin, Mylotarg, Campath, Bexxar, Erbitux), and (6) endocrine therapy: aromatase inhibitors (4-hydroandrostendione, exemestane, aminoglutehimide, anastrzole, letozole), anti-estrogens (Tamoxifen, Toremifine, Raoxifene, Faslodex), steroids such as dexamethasone, (7) Immuno-modulators: cytokines such as IFN-beta and IL2), inhibitors to integrins, other adhesion proteins and matrix metalloproteinases), (8) histone deacetylase inhibitors, (9) inhibitors of signal transduction such as inhibitors of tyrosine kinases like gleevec, (10) inhibitors of heat shock proteins, (11) retinoids such as all trans retinoic acid and (12) inhibitors of growth factor receptors or the growth factors themselves.

One class of chemotherapeutic agents are alkylating agents. An "alkylating agent" refers to a chemotherapeutic compound that chemically modify DNA and disrupt its function. Some alkylating agents alkylate DNA, others cause formation of cross links between nucleotides on the same strand, or the complementary strand, of a double-stranded DNA molecule, while still others cause base-pair mismatching between DNA strands. Exemplary alkylating agents include bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine. Another class of chemotherapeutic agents is the anti-metabolites. An "anti-metabolite" refers to a chemotherapeutic agent that interferes with the synthesis of biomolecules, including those required for DNA synthesis (e.g., nucleosides and nucleotides) needed to synthesize DNA. Examples of anti-metabolites include capecitabine, chlorodeoxyadenosine, cytarabine (and its activated form, ara-CMP), cytosine arabinoside, dacabazine, floxuridine, fludarabine, 5-fluorouracil, gemcitabine, hydroxyurea, 6-mercaptopurine, methotrexate, pentostatin, trimetrexate, and 6-thioguanine. An "anti-mitotic" chemotherapeutic agent refers to a chemotherapeutic agent that interferes with mitosis, typically through disruption of microtubule formation. Examples of anti-mitotic compounds include navelbine, paclitaxel, taxotere, vinblastine, vincristine, vindesine, and vinorelbine. An "intercalating agent" refers to a chemotherapeutic agent that inserts itself between adjacent base pairs in a double-stranded DNA molecule, disrupting DNA structure and interfering with DNA replication, gene transcription, and/or the binding of DNA binding proteins to DNA.

The term "combination therapy" refers to a therapeutic regimen that involves the provision of at least two distinct therapies to achieve an indicated therapeutic effect. For example, a combination therapy may involve the administration of two or more chemically distinct active ingredients, for example, a fast-acting chemotherapeutic agent and an anti-S1P antibody. Alternatively, a combination therapy may involve the administration of an anti-S1P molecule (e.g., an anti-S1P antibody) and/or one or more chemotherapeutic agents, alone or together with the delivery of radiation therapy and/or surgery. In the context of the administration of two or more chemically distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician. Similarly, when one or more anti-S1P molecule species, alone or in conjunction with a chemotherapeutic agents are combined with, for example, radiation and/or surgery, the drug(s) may be delivered before or after surgery or radiation treatment.

The term "hyperproliferative disorder" refers to diseases and disorders associated with, the uncontrolled proliferation cells, including but not limited to uncontrolled growth of organ and tissue cells resulting in cancers and benign tumors. Hyperproliferative disorders associated with endothelial cells can result in diseases of angiogenesis such as angiomas, endometriosis, obesity, Age-related Macular Degeneration and various retinopaties, as well as the proliferation of ECs and smooth muscle cells that cause restenosis as a consequence of stenting in the treatment of atherosclerosis. Hyperproliferative disorders involving fibroblasts (i.e., fibrogenesis) include but are not limited to disorers of excessive scaring (i.e., fibrosis) such as Age-related Macular Degeneration, cardiac remodeling and failure associated with myocardial infarction, excessive wound healing such as commonly occurs as a consequence of surgery or injury, keloids, and fibroid tumors and stenting.

In the context of this invention, a "liquid composition" refers to one that, in its filled and finished form as provided from a manufacturer to an end user (e.g., a doctor or nurse), is a liquid or solution, as opposed to a solid. Here, "solid" refers to compositions that are not liquids or solutions. For example, solids include dried compositions prepared by lyophilization, freeze-drying, precipitation, and similar procedures.

"Monotherapy" refers to a treatment regimen based on the delivery of one therapeutically effective compound, whether administered as a single dose or several doses over time.

"Neoplasia" refers to abnormal and uncontrolled cell growth. A "neoplasm", or tumor, is an abnormal, unregulated, and disorganized proliferation of cell growth, and is generally referred to as cancer. A neoplasm may be benign or malignant. A neoplasm is malignant, or cancerous, if it has properties of destructive growth, invasiveness, and metastasis. Invasiveness refers to the local spread of a neoplasm by infiltration or destruction of surrounding tissue, typically breaking through the basal laminas that define the boundaries of the tissues, thereby often entering the body's circulatory system. Metastasis typically refers to the dissemination of tumor cells by lymphatics or blood vessels. Metastasis also refers to the migration of tumor cells by direct extension through serous cavities, or subarachnoid or other spaces. Through the process of metastasis, tumor cell migration to other areas of the body establishes neoplasms in areas away from the site of initial appearance A "patentable" composition, process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude the unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that (1) preserves their validity and (2) provides the broadest reasonable interpretation under the circumstances.

The term "pharmaceutically acceptable salt" refers to salts which retain the biological effectiveness and properties of the agents and compounds of this invention and which are not biologically or otherwise undesirable. In many cases, the agents and compounds of this invention are capable of forming acid and/or base salts by virtue of the presence of charged groups, for example, charged amino and/or carboxyl groups or groups similar thereto. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) *J. Pharm. Sci.*, vol. 66, 1).

A "plurality" means more than one.

The terms "separated", "purified", "isolated", and the like mean that one or more components of a sample contained in a sample-holding vessel are or have been physically removed from, or diluted in the presence of, one or more other sample components present in the vessel. Sample components that may be removed or diluted during a separating or purifying step include, chemical reaction products, unreacted chemicals, proteins, carbohydrates, lipids, and unbound molecules.

The term "species" is used herein in various contexts, e.g., a particular species of chemotherapeutic agent. In each context, the term refers to a population of chemically indistinct molecules of the sort referred in the particular context.

"Specifically associate", "specific association," and the like refer to a specific, non-random interaction between two molecules, which interaction depends on the presence of structural, hydrophobic/hydrophilic, and/or electrostatic features that allow appropriate chemical or molecular interactions between the molecules.

Herein, "stable" refers to an interaction between two molecules (e.g., a peptide and a TLR molecule) that is sufficiently stable such that the molecules can be maintained for the desired purpose or manipulation. For example, a "stable" interaction between a peptide and a TLR molecule refers to one wherein the peptide becomes and remains associated with a TLR molecule for a period sufficient to achieve the desired effect.

A "subject" or "patient" refers to an animal in need of treatment that can be effected by molecules of the invention. Animals that can be treated in accordance with the invention include vertebrates, with mammals such as bovine, canine, equine, feline, ovine, porcine, and primate (including humans and non-humans primates) animals being particularly preferred examples.

A "therapeutically effective amount" (or "effective amount") refers to an amount of an active ingredient, e.g., an agent according to the invention, sufficient to effect treatment when administered to a subject in need of such treatment. Accordingly, what constitutes a therapeutically effective amount of a composition according to the invention may be readily determined by one of ordinary skill in the art. In the context of cancer therapy, a "therapeutically effective amount" is one that produces an objectively measured change in one or more parameters associated with cancer cell survival or metabolism, including an increase or decrease in the expression of one or more genes correlated with the particular cancer, reduction in tumor burden, cancer cell lysis, the detection of one or more cancer cell death markers in a biological sample (e.g., a biopsy and an aliquot of a bodily fluid such as whole blood, plasma, serum, urine, etc.), induction of induction apoptosis or other cell death pathways, etc. Of course, the therapeutically effective amount will vary depending upon the particular subject and condition being treated, the weight and age of the subject, the severity of the disease condition, the particular compound chosen, the dosing regimen to be followed, timing of administration, the manner of administration and the like, all of which can readily be determined by one of ordinary skill in the art. It will be appreciated that in the context of combination therapy, what constitutes a therapeutically effective amount of a particular active ingredient may differ from what constitutes a therapeutically effective amount of the active ingredient when administered as a monotherapy (i.e., a therapeutic regimen that employs only one chemical entity as the active ingredient).

The term "treatment" or "treating" means any treatment of a disease or disorder, including preventing or protecting against the disease or disorder (that is, causing the clinical symptoms not to develop); inhibiting the disease or disorder (i.e., arresting or suppressing the development of clinical symptoms; and/or relieving the disease or disorder (i.e., causing the regression of clinical symptoms). As will be appreciated, it is not always possible to distinguish between "preventing" and "suppressing" a disease or disorder since the ultimate inductive event or events may be unknown or latent. Accordingly, the term "prophylaxis" will be understood to constitute a type of "treatment" that encompasses both "preventing" and "suppressing". The term "protection" thus includes "prophylaxis".

The term "therapeutic regimen" means any treatment of a disease or disorder using chemotherapeutic and cytotoxic agents, radiation therapy, surgery, gene therapy, DNA vaccines and therapy, siRNA therapy, anti-angiogenic therapy, immunotherapy, bone marrow transplants, apatamers and other biologics such as antibodies and antibody variants, receptor decoys and other protein-based therapeutics.

According to the Merck Manual ($14^{th}$ edition, p. 1206) cancer is "a cellular malignancy whose unique characteristics—loss of normal controls—results in unregulated growth, lack of differentiation, and ability to invade local tissue and metastasize." Similarly, the National Cancer Institute of the NIH (see http://cancer.gov/) defines cancer as, "A term for diseases in which abnormal cells divide without control. Cancer cells can invade nearby tissues and can spread through the bloodstream and lymphatic system to other parts of the body." Cancer cells also avoid natural cell death and stimulate the formation of their own blood supply through a process known as angiogenesis. The NCI defines angiogenesis as "blood vessel formation. Tumor angiogenesis is the growth of blood vessels from surrounding tissue to a solid tumor. This is caused by the release of chemicals by the tumor." Inflammation is defined by the NIH as, "A response of redness, swelling, pain, and a feeling of heat in certain areas that is meant to protect tissues affected by injury or disease."

SUMMARY OF THE INVENTION

One aspect of the invention concerns methods for treating a hyperproliferative disorder. These methods comprise administering to a mammal (e.g., a bovine, canine, equine, ovine, or porcine animal, particularly a human) known or suspected to suffer from an S1P-associated hyperproliferative disorder a therapeutically effective amount of a composition comprising an agent that interferes with S1P activity, preferably in a pharmaceutically or veterinarily acceptable carrier, as the intended application may require. S1P-associated hyperproliferative disorders include neoplasias, disorder associated with endothelial cell proliferation, and disorders associated with fibrogenesis. Most often, the neoplasia will be a cancer. Typical disorders associated with endothelial cell proliferation are angiogenesis-dependent disorders, for example, cancers caused by a solid tumors, hematological tumors, and age-related macular degeneration. Disorders associated with fibrogenesis include those than involve aberrant cardiac remodeling, such as cardiac failure.

In preferred embodiments, the agent that interferes with S1P activity is an antibody specifically reactive with S1P. In other embodiments, the agent comprises a first binding moiety and a second binding moiety, wherein the first binding moiety is specifically reactive S1P and the second binding moiety is specifically reactive with a second molecule other than S1P. In some embodiments, the agent will comprise a first binding moiety and a second binding moiety, wherein the first binding moiety is specifically reactive with a first molecule that is a sphingolipid or sphingolipid metabolite and the second binding moiety is specifically reactive with a second molecule that is a molecular species different from the first molecule. Representative examples include bispecific antibodies. In those wherein the first moiety is an antibody, the binding moiety may also be an antibody. In preferred embodiments, the first and second moieties are linked via a linker moiety, which may have two to many 100's or even thousand of valencies for attachment of first and second binding moieties by one or different chemistries.

Such agents may comprise a plurality of first binding moieties, a plurality of second binding moieties, or a plurality of first binding moieties and a plurality of second binding moieties. Preferably, the ratio of first binding moieties to second binding moieties is about 1:1, although it may range from about 1000:1 to about 1:1000, wherein the ratio is preferably measured in terms of valency.

The compositions of the invention may also comprise a first agent and a second agent, wherein the first agent comprises a first binding moiety specifically reactive with a first molecule selected from the group consisting of a sphingolipid and a sphingolipid metabolite and the second agent comprises a second binding moiety specifically reactive with a second molecular that is a molecular species different than the first molecule. The first and/or second agent may be an antibody. The ratio of first agent to second agent may range from about 1,000:1 to 1:1,000, although the preferred ratio is about 1:1.

In preferred embodiment, the composition comprising an agent that interferes with S1P activity is administered as a monotherapy, while in other preferred embodiments, the composition comprising the agent that interferes with S1P activity is administered as part of a combination therapy. Preferred combination therapies include, in addition to administration of the composition comprising an agent that interferes with S1P activity, delivering a second therapeutic regimen selected from the group consisting of administration of a chemotherapeutic agent, radiation therapy, surgery, and a combination of any of the foregoing.

Another aspect of the invention relates to kits containing a composition according to the invention or for performing a method according to the invention.

Another object of the invention concerns agents that comprise a first binding moiety and a second binding moiety. Here, a "binding moiety" is any molecule that specifically binds to the desired, target analyte. The first binding moiety is specifically reactive with a first molecule selected from the group consisting of a sphingolipid and a sphingolipid metabolite. The second binding moiety is specifically reactive with a second molecule that is a molecular species different from the first molecule. Preferred examples of first and second binding moieties include antibodies (including polyclonal, monoclonal, humanized antibodies and antibodies derived from humanized transgenic animals), antibody fragments, single chain antibodies, and T cell receptors and receptor fragments.

In some embodiments, the agent comprises a plurality of first binding moieties. In other, it comprises a plurality of second binding moieties. In still others, it comprises a plurality of first and second binding moieties. In some embodiments, the ratio of first binding moieties to second binding moieties is from about 1000:1 to about 1:1000. A preferred ratio of first to second binding moieties is about 1:1. Preferably, such ratios are measured in terms of valency, as the first and/or second binding moieties may have one or more valencies, i.e., sites for binding their intended target moieties. In some embodiments, the agent is a bispecific antibody, i.e., an antibody wherein one of the two antigen binding domains of the antibody binds one epitope of an antigen, whereas the other antigen-binding domain of the antibody binds a different epitope species. The different epitopes bound by the two antigen-binding domains may be from the same antigen, or from different antigens. In other embodiments, the agent comprises a plurality of antibody fragments, single chain antibodies, and/or T cell receptors and/or receptor fragments that bind at least two different target analytes.

The agents of the invention include those wherein the first and second binding moieties are linked, directly or through a linker moiety. Alternatively, the first and second binding moieties may be associated through incorporation in a vesicle, for example, a liposome. They may also be linked by the use of dendrimer, which dendrimer has multiple reactive sites for the addition of desired molecules, e.g., first and/or second binding moieties, using appropriate chemistries.

In a related aspect, the invention concerns compositions that comprise an agent and a carrier. These compositions may be packaged in any suitable container, and they may be further incorporated into a package, preferably with directions for use.

Another aspect of the invention concerns compositions that comprise a first agent and a second agent, wherein the first agent comprises a first binding moiety specifically reactive with a first molecule selected from the group consisting of a sphingolipid and a sphingolipid metabolite and the second agent comprises a second binding moiety specifically reactive with a second molecule that is a molecular species different than the first molecule.

Still another aspect of the invention relates to methods of treating or preventing a hyperproliferative disorder, e.g., a cancer. Typically, these methods involve administering to a subject suffering from a hyperproliferative disorder an effective amount of each of an agent (or a plurality of different agent species) according to the invention and a cytotoxic agent. Cytotoxic agents include chemotherapeutic drugs.

A related aspect concerns methods of reducing toxicity of a therapeutic regimen for treatment or prevention of a hyperproliferative disorder. Such methods comprise administering to a subject suffering from a hyperproliferative disorder an effective amount of an agent (or a plurality of different agent species) according to the invention before, during, or after administration of a therapeutic regimen intended to treat or prevent the hyperproliferative disorder.

Yet another aspect of the invention concerns methods of enhancing a survival probability of a subject treated for a hyperproliferative disorder by administering to a subject suffering from a hyperproliferative disorder an agent (or a plurality of different agent species) according to the invention before, during, or after administration of a therapeutic regimen intended to treat or prevent the hyperproliferative disorder to enhance the subject's survival probability.

Other features and advantages of the invention will be apparent from the following drawings, detailed description, and appended claims.

As those in the art will appreciate, the following detailed description describes certain preferred embodiments of the invention in detail, and is thus only representative and does not depict the actual scope of the invention. Before describing the present invention in detail, it is understood that the invention is not limited to the particular aspects and embodiments described, as these may vary. It is also to be understood that the terminology used herein is for the purpose of describing particular embodiments only, and is not intended to limit the scope of the invention defined by the appended claims.

DETAILED DESCRIPTION

The present invention is based on the surprising discovery that anti-S1P molecules, particularly anti-S1P antibodies, can be used to treat hyperproliferative diseases associated with S1P activity. Additionally, a patentable class of anti-S1P molecules, namely, agents that comprise a first binding moiety and a second binding moiety, one of which moieties bind S1P, is also described.

1. Introduction.
  A. Sphingolipids

Figure 1:
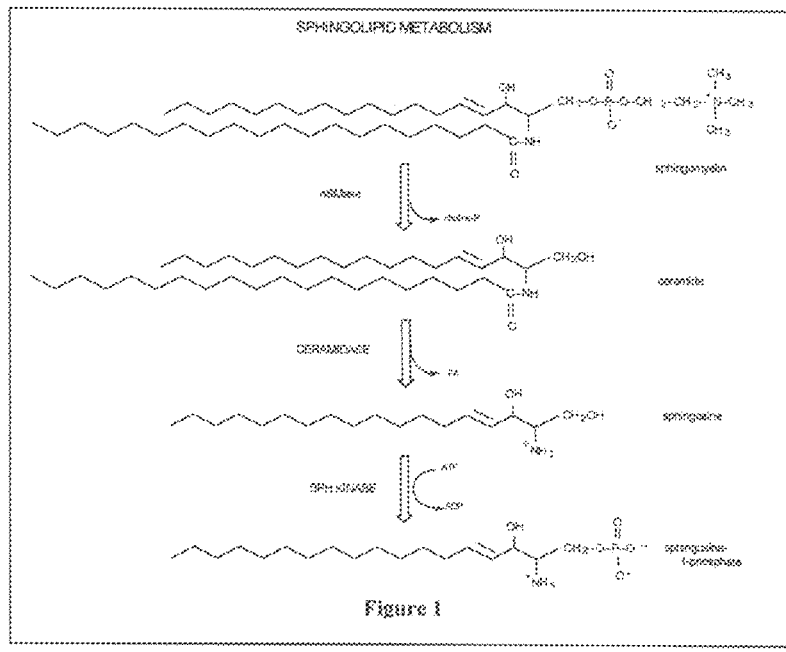
FIG. 1 is an illustration showing the components of the sphingomyelinase signaling cascade.
Figure 2:
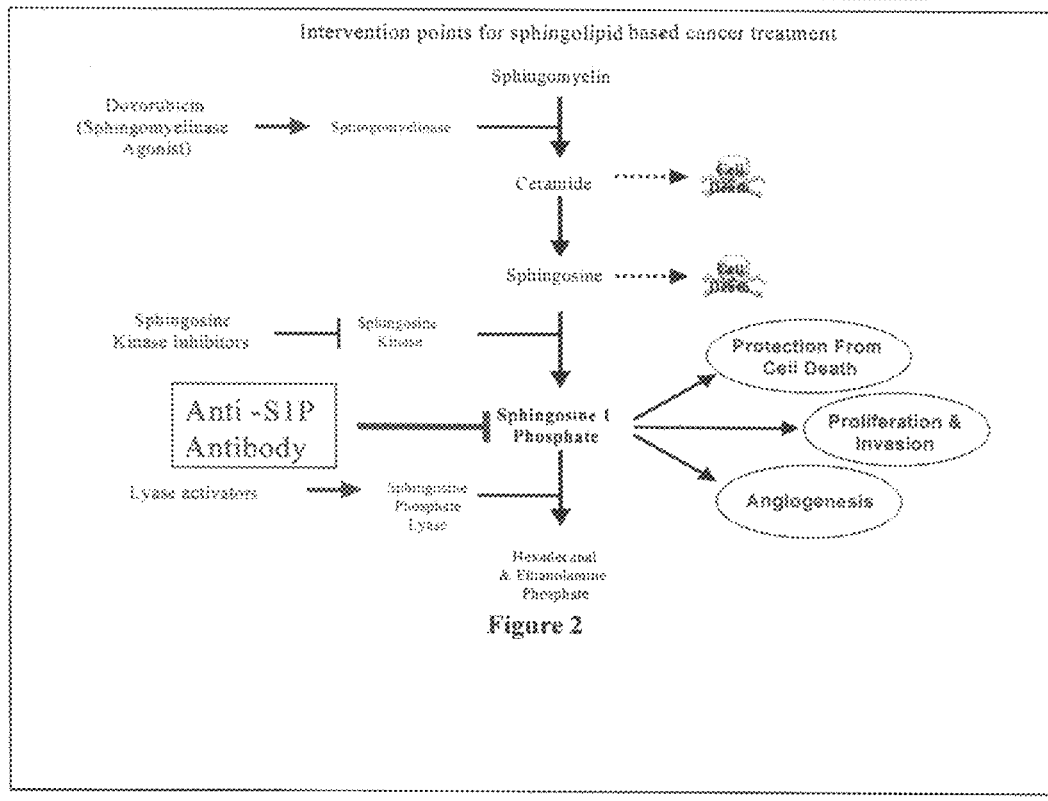
FIG. 2 is an diagram showing several intervention points for a sphingolipid-based treatments for hyperproliferative disorders, including cancer. As illustrated, most of the intervention points are protein targets, typically enzymes in the sphingolipid signaling pathway, the most prominent of which is SK. An anti-S1P molecular sponge approach, as represented by an anti-S1P antibody, allows S1P to be neutralized, thereby inhibiting its pro-tumorigenic effects. In favor of the antibody approach is the low toxicity, long-half life and specificity of the therapeutic antibody to its target.

Sphingolipids are primary structural components of cell membranes that also serve as cellular signaling and regulatory molecules. FIG. 1 shows the sphingolipid signaling cascade, including the bioactive lipid mediators, ceramide (CER), sphingosine (SPH), and sphingosine-1-phosphate (S1P). These mediators are derived from sphingomyelin, which is present in the plasma membranes of all mammalian cells.

The neutral form of sphingomyelinase (nSMase) is a key early component of the sphingolipid signaling pathway (FIG. 1). Tumor necrosis factor alpha (TNFα) is a well-known activator of nSMase, CER production, and apoptosis in many cell types, including cancer cell lines, and the activation of nSMase has been shown to be critical for TNFα-induced apoptosis, making it a target for drug discovery.

The sphingolipid signaling molecule, S1P, is produced from SPH through the action of sphingosine kinase (SPHK). Two isoforms of the kinase have been identified, SPHK1 and SPHK2. While CER and SPH are commonly associated with apoptosis, S1P is typically viewed as an extracellular mediator of cell proliferation and activation of survival pathways. S1P can act as a ligand for a set of G Protein Coupled Receptors (GPCRs) belonging to the S1P/LPA receptor family, formerly known as Edg receptors; however, intracellular actions of S1P have also been suggested. Moreover, it has been suggested that the balance between CER/SPH levels versus S1P provides a rheostat mechanism that decides whether a cell is sent into the death pathway or is protected from apoptosis by S1P.

The key regulatory enzyme of the rheostat mechanism is SPHK, whose role is to convert the death-promoting sphingolipids (CER/SPH) into the growth-promoting S1P. It has been shown that NIH-3T3 fibroblasts stably transfected with SPHK exhibit enhanced cell proliferation accompanied by increased S1P production, and SPHK over-expressers can escape contact inhibition, a property commonly exhibited by transformed cells. Thus, S1P can enhance metastatic potential of selected human cancer cell lines. Moreover, the SPHK transfectants can produce tumors when injected subcutaneous into NOD/SCID mice. Significantly, SPHK is over-expressed in many solid tumors, such as those of the breast, colon, lung, ovary, stomach, uterus, kidney, and rectum. It has been shown that apoptosis can be induced in several human tumor-derived cell lines by treatment with a small molecule inhibitor of SPHK, which also reduce S1P levels. Also, genotoxics and other anti-neoplastics down-regulate SPHK as part of their mechanisms of action. Similarly, down-regulation of SPHK by siRNA can decrease melanoma cells resistance to apoptosis, while the protective effect of enhanced Bcl-2 expression has been attributed to increased SPHK expression. Further, the anti-neoplastic effect of FTY70 has been attributed to its down-regulation of S1P receptors, suggesting that interfering with S1P action at the receptor level could also be valuable in anti-tumor therapy, for example, through the use of an antibody that interferes with S1P receptor binding.

Taken together, these findings demonstrate that S1P is a growth factor likely produced by tumor cells themselves, and that lowering the concentration of S1P may cause the apoptosis seen upon growth factor withdrawal.

B. S1P as a Valid Target for Cancer Therapy.

One cancer therapy strategy is to reduce the biologically available extracellular levels of the tumor-promoter, S1P, either alone or in combination with traditional anti-cancer treatments, including the administration of chemotherapeutic agents, such as an anthracycline. To this end, a monoclonal antibody (mAb) has been developed that is specific for S1P, which can selectively adsorb S1P from the serum, acting as a molecular sponge to neutralize extracellular S1P. Since S1P has been shown to be pro-angiogenic, an added benefit to the antibody's effectiveness can be derived from the antibody's ability to starve the blood supply of the growing tumor. Thus, another sphingolipid-based anti-neoplastic strategy involves combining known activators of CER and SPH production (doxorubicin, doxorubicin, radiation therapy) coupled with a strategy to reduce S1P levels.

While sphingolipid-based anti-cancer strategies that target key enzymes of the sphingolipid metabolic pathway, such as SPHK, have been proposed, S1P itself has not been emphasized, largely because of difficulties in attacking this and related targets. As described herein, a highly specific monoclonal antibody to S1P has been produced that recognizes S1P in the physiological range and is capable of neutralizing S1P by molecular combination. Use of this antibody (and its derivatives) will deprive growing tumor cells of an important growth and survival factor. Moreover, use of such an antibody-based cancer therapy could also be effective when used in combination with conventional cancer treatments, such as surgery, radiation therapy, and/or the administration of cytotoxic anti-cancer agents. An antibody-based combination therapy may improve the efficacy of chemotherapeutic agents by sensitizing cells to apoptosis while minimizing their toxic side effects, although administration of the antibody alone may also have efficacy in delaying the progression of disease. Indeed, the ability of the anti-S1P mAb to retard tumor progression in mouse models of human cancer and in allograft mouse models demonstrates the utility of anti-S1P antibody approaches in treating both human and animal tumors. Moreover, the discovery that several human cancers types (e.g., ovarian, breast, lung, and melanoma) can be treated in xenograft models demonstrates that the anti-S1P antibody approaches are not limited to one cancer cell or tissue type.

C. Sphingolipids and Angiogenesis.

Angiogenesis is the process by which new blood vessels are formed from existing blood vessels. The angiogenesis associated with solid and circulating tumors is now considered to be a crucial component of tumorigenesis, as today the view that tumor growth is dependent upon neovascularization is scientifically well accepted.

S1P stimulates DNA synthesis and chemotactic motility of human venous endothelial cells (HUVECs), while inducing differentiation of multicellular structures essential early blood vessel formation. S1P also promotes the migration of bone marrow-derived endothelial cell precursors to neovascularization sites, and cells that over-express S1P receptors are resistant the anti-angiogenic agents, thalidomide and Neovastat. Thus, S1P, and particularly S1 receptors, are required for angiogenesis and neovascularization. Finally, cross-talk occurs between S1P and other pro-angiogenic growth factors such as VEGF, EGF, PDGF, bFGF, and IL-8. For example, S1P transactivates EGF and VEGF2 receptors, and VEGF up-regulates S1P receptor expression (Igarashi, Erwin et al. 2003).

As will be appreciated, clinical control of angiogenesis is a critical component for the treatment of cancer and other angiogenesis-dependent diseases such as age-related macular degeneration (AMD) and endometriosis. Anti-angiogenic therapeutics are also particularly attractive because the vascular endothelial cells that are involved in tumor angiogenesis do not mutate as easily as do cancer cells; consequently, vascular endothelial cells are less likely than cancer cells to gain resistance to prolonged therapy, making them useful therapeutic targets.

There are several lines of evidence suggesting that S1P is a potentially significant pro-angiogenic growth factor that may be important in tumor angiogenesis, including that: anti-S1P antibodies can neutralize S1P-induced tube formation, migration of vascular endothelial cells, and protection from cell death in various in vitro assays using HUVECs; injection of breast adenocarcinoma MCF-7 cells expressing elevated S1P levels into mammary fat pads of nude mice results in an increase of angiogenesis-dependent tumors that are both larger and more numerous than when control cells are used; anti-S1P antibodies can dramatically reduce tumor-associated angiogenesis in an orthotopic murine melanoma allograft model; S1P increases new capillary growth into Matrigel plugs implanted in mice, an effect that can be neutralized by the systemic administration of anti-S1P antibodies; in vivo administration of anti-S1P antibodies can completely neutralize pro-angiogenic growth factor-induced angiogenesis (e.g., by bFGF and VEGF) in murine Matrigel plug assays; S1P stimulates the release of bFGF and VEGF from tumor cells in vitro and in vivo, an effect that can be reversed by anti-S1P antibodies; S1P enhances in vitro motility and invasion of a large number of different types of cancer cells, including glioblastoma multiforme cells; and anti-S1P antibodies significantly reduce the neovascularization associated with animal models of AMD.

The importance of S1P in the angiogenic-dependent tumors makes S1P an excellent target for cancer treatment. Indeed, antibody neutralization of extracellular S1P may result in a marked decrease in cancer progression in mammals, including humans, as a result of inhibition of blood vessel formation with concomitant loss of the nutrients and oxygen needed to support tumor growth. Thus, anti-S1P antibodies have several mechanisms of action, including: (1) direct effects on tumor cell growth; (2) indirect anti-angiogenic effects on vascular endothelial cells; and (3) the indirect anti-angiogenic effects that prevent the release and action of other pro-angiogenic growth factors. Accordingly, anti-S1P antibodies can also serve as anti-metastatic therapeutics, in addition to an anti-angiogenic therapeutics. They will also be useful in treating other hyperproliferative disorders associated with S1P activity, such as those cause by aberrant endothelial cell proliferation, as occurs with the angiogenesis associated with AMD.

D. S1P Fibrogenesis and Scaring.

i. S1P, Fibroblasts and the Remodeling Process

It is clear that cardiac fibroblasts, particularly myofibroblasts, are key cellular elements in scar formation in response to the cell death and inflammation of a myocardial infarction (MI). Myofibroblast collagen gene expression is a hallmark of remodeling and necessary for scar formation. In addition to its other activities, S1P is also an inflammatory mediator that makes profound contributions to wound healing by activating fibroblast migration and proliferation, in addition to activating platelets, stimulating angiogenesis, and promoting smooth muscle function. Thus, S1P, perhaps produced locally by injured myocardium, could, in part, be responsible for the maladaptive wound healing associated with cardiac remodeling and failure, particularly by activating myofibroblasts in the heart.

There are three general responses of cells to S1P: protection from cell death; stimulation of proliferation; and the promotion of migratory responses. Accordingly, S1P activity or involvement with a particular disorder, cell line, etc. can be assessed by adapting assays of this sort for this purpose. There is evidence that fibroblasts respond to S1P in all three ways to promote wound healing. For instance, in several of the examples in the Example section below, evidence is presented that demonstrates that S1P contributes to remodeling by promoting cardiac myofibroblast activity (proliferation, migration, and collagen gene expression).

ii. S1P and Protection From Cell Death

As is the case for many cell types, fibroblasts are directly protected from apoptosis by addition of S1P, and apoptosis is enhanced by inhibitors of SPHK, and S1P blocks cytochrome C release and the resultant caspase activation. Further, fibroblasts transfected with SPHK1 exhibit protection from apoptosis, an effect that may depend upon translocation of SPHK1 to the plasma membrane. It is well-established that SPHK1 up-regulates Akt, thereby regulating Bcl-2 family members and protecting from apoptosis. Also, $S1P_3$ is required for Akt phosphorylation in mouse embryonic fibroblasts (MEFs). Also, up-regulation of SPHK and resulting increases in S1P levels protect cardiofibroblasts from apoptosis.

Ceramide, an upstream metabolite of S1P, decreases mitochondrial membrane potential coincident with increasing the transcription of death inducing mitochondrial proteins. Because of the rheostat mechanism, S1P may have the opposite effect and protect cardiac myofibroblasts (i.e., fully differentiated fibroblasts in the heart) from apoptosis. Indeed, S1P may even activate autophagy as a protection mechanism. These effects could be reversed by the neutralizing anti-S1P antibodies (or other molecules that bind and act to sequester S1P).

iii. S1P Induces Fibroblast Proliferation, Differentiation, and Promotes Collagen Gene Expression It has been demonstrated that fibroblasts respond to S1P treatment by increasing DNA synthesis, and fibroblasts transfected with SPHK1 exhibit increased cellular proliferation. Similar to its effects on non-cardiac fibroblasts, S1P is believed to stimulate cardiofibroblast proliferation (and subsequent differentiation). This effect occurs during remodeling and is another mechanism that explains S1P's maladaptive behavior (in this case, scar formation), particularly since S1P stimulates proliferation in multiple cell types, and results in S1P-dependent DNA synthesis in cultured cardiofibroblasts (see Example 14, below).

A salient characteristic of fibroblasts, including cardiac myofibroblasts, is their ability to express collagen and lay down scar. It is well known that TGFβ up-regulates collagen production and promotes fibrosis in the remodeling heart. TGFβ has been shown specifically in cardiac fibroblasts to up-regulate several pro-fibrotic proteins, convert fibroblasts to myofibroblasts, and stimulate inflammatory protein expression. Interestingly, TGFβ increases SPHK mRNA, protein, and activity associated S1P levels, and up-regulation of TIMP1 by TGFβ is blocked by siRNA for SPHK and TIMP1. TIMP1 is generally expressed in cells transitioning from fibroblasts to myofibroblasts. Also, TGFβ-stimulated transition to myofibroblasts requires constitutive phosphorylation of FAK, which is regulated by signaling through $S1P_1$. Thus, signaling by TGFβ is closely linked to S1P. It has also been established that proliferating fibroblasts do not have high levels of collagen expression, while non-proliferating fibroblasts can be stimulated to transition to myofibroblasts and express large amounts of alpha smooth muscle actin (αSMA).

iv. S1P Induces Migration in Fibroblasts

Migration is necessary for cardiac fibroblast invasion of an infarcted area. S1P is likely involved in this process due to its profound stimulation of migration in other cell types, and thus may contribute to fibrosis. Reducing fibrosis would reduce scar formation and, in the context of cardiac tissue, would allow for improved heart function after a myocardial infarction (MI). Recognizing that some scar formation is necessary, however, to prevent cardiac rupture in the immediate post-MI period, it would be desirable to initiate limiting scar formation after the time that the risk of cardiac rupture subsides, particularly in the peri-infarct zone but also in the infarct zone itself.

It has also been demonstrated that S1P activates signaling systems, especially Rho, and resulting gene expression is consistent with its substantial effects on cellular migration. While it $S1P_1$ is required for mitogenicity and survival effects of fibroblasts, $S1P_1$ expression is associated with enhanced cell migration.

Assembly of contractile actin/myosin filaments is controlled by Rho/Rac/Cdc42 system and activation of all three Rho GTPases is necessary for cellular migration to take place. It is necessary for all three Rho GTPases to be expressed for migration to take place, but their localization of expression must vary for the coordination of their separate activities. For example, Rac and Cdc42 are responsible for lamellipodia and filopodial protrusion formation through actin polymerization. Importantly, Rho, Rac, and Cdc42 are responsible for S1P stimulated cellular migration. $S1P_2$, $S1P_3$, and $S1P_4$ activate Rho through coupling to $G_{13}$. The activation of these Rho GTPases by S1P is thus believed to be responsible for migration of cardiac fibroblasts in response to the wound created by an acute MI.

The examples in the Examples section below provide strong evidence that specific, sensitive anti-S1P antibodies can act as molecular sponges to selectively absorb and neutralize S1P so that it cannot bind to the complement of S1P receptors on the surfaces of fibroblasts and inflammatory cells, thus decreasing inflammation and scaring. The effective extracellular concentration of S1P would thus be lowered by such a molecular sponge much in the same way anti-TNFα antibodies and receptor decoys (Embrel, Remicade) neutralize TNFα or the mAb sponge, Avastin, neutralizes the pro-angiogenic growth factor, vascular endothelial growth factor (VEGF).

2. Binding Sphingolipids for Therapeutic Benefit.

The methods and compositions of the invention, whether based on monotherapy or combination therapy, are said to be "sphingolipid-based" in order to indicate that these therapies can change the relative, absolute, or available concentration (s) of certain disease- or disorder-associated sphingolipids. Examples of disease- and disorder-associated sphingolipids, particularly hyperproliferative disorder-associated sphingolipids include, but are not limited, to ceramide (CER), sphingosine-1-phosphate (S1P), and sphingosine (SPH).

One way to control the amount hyperproliferative disorder-associated sphingolipids in a patient is by providing a composition that binds one or more sphingolipids or sphingolipid metabolites. Antibodies and other compounds that provide such binding may, for example, be used as therapeutic "sponges" that reduce the level of one or more free sphingolipid species in tissues and extracellular fluids, particularly blood. By "sponge" is meant that the sphingolipid-binding molecule (i.e., an anti-sphingolipid molecule), particularly an S1P-binding molecules (i.e., an anti-S1P molecule), specifically interacts with the target sphingolipid. Antibodies and other compounds that bind to cellular receptors of sphingolipids may also (or alternatively) be used to compete with and/or prevent sphingolipids from binding to receptors.

A. Antibodies that Bind Sphingolipids

One aspect of the invention concerns antibodies that bind sphingolipids, particularly S1P, that can be delivered to a patient to provide treatment for a hyperproliferative disorder, particularly an S1P-associated hyperproliferative disorder. Such methods may, by way of non-limiting example, (1) modulate the effective concentration of a specific sphingolipid or metabolite (e.g., S1P), (2) sterically inhibit the binding of a sphingolipid or a sphingolipid metabolite to a cellular receptor therefor, or to lower the concentration of a sphingolipid that is available for binding to such a receptor; (3) sterically inhibit the enzymatic conversion of a sphingolipid or a sphingolipid metabolite; or (4) remove sphingolipid or a sphingolipid metabolite from blood in vivo or ex vivo. In preferred embodiments, such antibodies are used as part of a combination therapy, while in other embodiments, they (or one or more of their antigen-binding domains) are incorporated into an agent that contains other moiety that binds to or otherwise specifically interacts with a different molecular species than that of the anti-sphingolipid moiety.

The term "antibody" is meant to encompass an immunoglobulin molecule obtained by in vitro or in vivo generation of an immunogenic response, and includes polyclonal, monospecific, and monoclonal antibodies, as well as T cell receptors, and fragments and derivatives thereof. An "immunogenic response" is one that results in the production of antibodies directed to one or more epitopes of an antigen. An "epitope" is a single antigenic determinant in a molecule.

Polyclonal antibodies are generated in an immunogenic response to an antigen (very often a protein or polypeptide) having many epitopes, and thus generally include a population of different antibodies directed to different epitopes within the antigen. Methods for producing polyclonal antibodies are well known in the art (see, e.g., Cooper et al, Section III of Chapter 11 in: Short Protocols in Molecular Biology, 2nd Ed., Ausubel et al., eds., John Wiley and Sons, New York, 1992, pages 11-37 to 11-41).

Monospecific antibodies are generated in a humoral response to a short (typically, 5 to 20 amino acids) immunogenic polypeptide that corresponds to a few (preferably one) isolated epitopes of the protein from which it is derived. A plurality of monospecific antibodies includes a variety of different antibodies directed to a specific portion of the protein, i.e., to an amino acid sequence that contains at least one, preferably only one, epitope. Methods for producing monospecific antibodies are known in the art (see, e.g., Id., pages 11-42 to 11-46).

A monoclonal antibody is a specific antibody that recognizes a single, specific epitope of an antigen. In a population of a monoclonal antibody molecules, each antibody molecule is identical to the others in the population. In order to isolate a monoclonal antibody, a clonal cell line that expresses, displays, and/or secretes a particular monoclonal antibody is first identified. This clonal cell line can be used to produce the desired monoclonal antibodies. Methods for the preparation of clonal cell lines and of monoclonal antibodies expressed thereby are known in the art (see, for example, Fuller et al, Section II of Chapter 11 in: Short Protocols in Molecular Biology, 2nd Ed., Ausubel et al., eds., John Wiley and Sons, New York, 1992, pages 11-22 to 11-11-36).

T cell receptors (TCR) are a distinct class of proteins that are genetically and structurally related to antibodies. TCR proteins belong to the immunoglobulin superfamily and have molecular structures similar to those of antibodies. Like antibodies, TCRs specifically recognize (i.e., specifically and bind) specific ligands. Complexes of TCRs are displayed on T cells and bind specific antigens for the purpose of triggering molecular events associated with T cell differentiation and activation. Like antibodies, TCRs recognize particular antigens. However, because of differences in the precise structures of the portions of TCR proteins that bind ligands and the amino acid sequences associated with those structures, as well as different mechanisms by which genes encoding a protein are diversified by rearrangement and mutation.

Antibody fragments and derivatives are proteins that are derived from antibodies and T-cell receptors and which retain the ability to specifically recognize the ligand recognized by the "parent" antibody or TCR. Preferred fragments include Fab fragments (i.e., an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')2 (two Fab' molecules joined by interchain disulfide bonds in the hinge regions of the heavy chains; the Fab' molecules may be directed toward the same or different epitopes); and a bispecific Fab (an Fab molecule having two antigen binding domains, each of which may be directed to a different epitope).

Single chain antibodies (scFv) comprise a variable, antigen-binding determinative region of a single light and heavy chain of an antibody linked together by a chain of 10-25 amino acids. U.S. Pat. Nos. 5,260,203; 5,869,620; 5,455,030; 5,518,889; 5,534,621; 4,946,778; 6,025,165; and 6,027,725.

Complexes of single chain antibodies are also within the scope of the invention and include, but are not limited to, a disulfide-linked Fv, or dsFv (the variable, antigen-binding determinative region of a single light and heavy chain of an antibody linked together by a disulfide bond; a bispecific sFv (a scFv or a dsFv molecule having two antigen-binding domains, each of which may be directed to a different epitope); a diabody (a dimerized scFv formed when the VH domain of a first scFv assembles with the VL domain of a second scFv and the VL domain of the first scFv assembles with the VH domain of the second scFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes).

The term "antibody" also includes genetically engineered antibodies and/or antibodies produced by recombinant DNA techniques and "humanized" antibodies. Humanized antibodies have been modified, by genetic manipulation and/or in vitro treatment to be more human, in terms of amino acid sequence, glycosylation pattern, etc., in order to reduce the antigenicity of the antibody or antibody fragment in an animal to which the antibody is intended to be administered.

B. A Preferred Anti-S1P Monoclonal Antibody

A preferred biospecific monoclonal anti-S1P antibody (anti-S1P mAb) has been developed, and has been deposited with the A.T.C.C. and assigned accession number 306D326.1#26. This antibody can be used as a therapeutic molecular sponge to selectively absorb S1P and thereby thus lower the effective in vivo extracellular S1P concentrations for the purpose of treating hyperproliferative disorders that associated with S1P activity. This can result in the reduction of tumor volume and metastatic potential, as well as the simultaneous blockage of new blood vessel formation that otherwise can feed the growing tumor. This antibody (and molecules having an equivalent activity) can also be used to treat other hyperproliferative disorders impacted by S1P, including unwanted endothelial cell proliferation, as occurs, for example, in age-related macular degeneration and endometriosis, disorders related to fibrogenesis, and in many cancers. In addition, the ability of S1P to protect cells from apoptosis can be reversed by the agents such as the antibody, thus increasing the efficacy of standard pro-apoptotic chemotherapeutic drugs.

3. Pharmaceutical Compositions.

Another aspect of the invention is drawn to compositions, including but not limited to pharmaceutical and/or biological compositions. According to the invention, a "composition" refers to a mixture comprising at least one carrier, preferably a physiologically acceptable carrier, and one or more therapeutic agents according to the invention. The term "carrier" defines a chemical compound that does not inhibit or prevent the incorporation of therapeutic agents into cells or tissues. A carrier typically is an inert substance that allows an active ingredient to be formulated or compounded into a suitable dosage form (e.g., a pill, a capsule, a gel, a film, a tablet, a microparticle (e.g., a microsphere), a solution etc.). A "physiologically acceptable carrier" is a carrier suitable for use under physiological conditions that does not abrogate (reduce, inhibit, or prevent) the biological activity and properties of the compound. For example, dimethyl sulfoxide (DMSO) is a carrier as it facilitates the uptake of many organic compounds into the cells or tissues of an organism. Preferably, the carrier is a physiologically acceptable carrier, preferably a pharmaceutically or veterinarily acceptable carrier, in which the therapeutic agent is disposed. A "pharmaceutical composition" refers to a composition wherein the carrier is a pharmaceutically acceptable carrier, while a "veterinary composition" is one wherein the carrier is a veterinarily acceptable carrier. The term "pharmaceutically acceptable carrier" or "veterinarily acceptable carrier" includes any medium or material that is not biologically or otherwise undesirable, i.e., the carrier may be administered to an organism along with a therapeutic agent, composition or compound without causing any undesirable biological effects or interacting in a deleterious manner with the complex or any of its components or the organism. Examples of pharmaceutically acceptable reagents are provided in The United States Pharmacopeia, The National Formulary, United States Pharmacopeial Convention, Inc., Rockville, Md. 1990, hereby incorporated by reference herein into the present application.

The compositions of the invention can further comprise other chemical components, such as diluents and excipients. A "diluent" is a chemical compound diluted in a solvent, preferably an aqueous solvent, that facilitates dissolution of the therapeutic agent in the solvent, and it may also serve to stabilize the biologically active form of the therapeutic agent or one or more of its components. Salts dissolved in buffered solutions are utilized as diluents in the art. For example, preferred diluents are buffered solutions containing one or more different salts. A preferred buffered solution is phosphate buffered saline (particularly in conjunction with compositions intended for pharmaceutical administration), as it mimics the salt conditions of human blood. Since buffer salts can control the pH of a solution at low concentrations, a buffered diluent rarely modifies the biological activity of a therapeutic agent.

An "excipient" is any more or less inert substance that can be added to a composition in order to confer a suitable property, for example, a suitable consistency or to form a drug. Suitable excipients and carriers include, in particular, fillers such as sugars, including lactose, sucrose, mannitol, or sorbitol cellulose preparations such as, for example, maize starch, wheat starch, rice starch, agar, pectin, xanthan gum, guar gum, locust bean gum, hyaluronic acid, casein potato starch, gelatin, gum tragacanth, methyl cellulose, hydroxypropylmethyl-cellulose, polyacrylate, sodium carboxymethylcellulose, and/or polyvinylpyrrolidone (PVP). If desired, disintegrating agents can also be included, such as cross-linked polyvinyl pyrrolidone, agar, or alginic acid or a salt thereof such as sodium alginate. Other suitable excipients and carriers include hydrogels, gellable hydrocolloids, and chitosan.

The compositions of the invention can be formulated in any suitable manner. Therapeutic agents may be uniformly (homogeneously) or non-uniformly (heterogeneously) dispersed in the carrier. Suitable formulations include dry and liquid formulations. Dry formulations include freeze dried and lyophilized powders, which are particularly well suited for aerosol delivery to the sinuses or lung, or for long term storage followed by reconstitution in a suitable diluent prior to administration. Other preferred dry formulations include those wherein a composition according to the invention is compressed into tablet or pill form suitable for oral administration or compounded into a sustained release formulation. When the composition is intended for oral administration but the therapeutic agent is to be delivered to epithelium in the intestines, it is preferred that the formulation be encapsulated with an enteric coating to protect the formulation and prevent premature release of the therapeutic agents included therein. As those in the art will appreciate, the compositions of the invention can be placed into any suitable dosage form. Pills and tablets represent some of such dosage forms. The compositions can also be encapsulated into any suitable capsule or other coating material, for example, by compression, dipping, pan coating, spray drying, etc. Suitable capsules include those made from gelatin and starch. In turn, such capsules can be coated with one or more additional materials, for example, and enteric coating, if desired. Liquid formulations include aqueous formulations, gels, and emulsions.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition that may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

Those skilled in the art will appreciate that when the compositions of the present invention are administered as agents to achieve a particular desired biological result, which may include a therapeutic or protective effect(s) (including vaccination), it may be necessary to combine the therapeutic agents of the invention with a suitable pharmaceutical carrier. The choice of pharmaceutical carrier and the preparation of the therapeutic agent as a therapeutic or protective agent will depend on the intended use and mode of administration. Suitable formulations and methods of administration of therapeutic agents include those for oral, pulmonary, nasal, buccal, ocular, dermal, rectal, or vaginal delivery.

Those skilled in the art will appreciate that when the compositions of the present invention are administered as agents to achieve a particular desired biological result, which may include a therapeutic or protective effect(s) (including vaccination), it may be necessary to combine the therapeutic agents of the invention with a suitable pharmaceutical carrier. The choice of pharmaceutical carrier and the preparation of the therapeutic agent as a therapeutic or protective agent will depend on the intended use and mode of administration. Suitable formulations and methods of administration of therapeutic agents include those for oral, pulmonary, nasal, buccal, ocular, dermal, rectal, or vaginal delivery.

Those skilled in the art will appreciate that when the compositions of the present invention are administered as agents to achieve a particular desired biological result, which may include a therapeutic or protective effect(s) (including vaccination), it may be necessary to combine the therapeutic agents of the invention with a suitable pharmaceutical carrier. The choice of pharmaceutical carrier and the preparation of the therapeutic agent as a therapeutic or protective agent will depend on the intended use and mode of administration. Suitable formulations and methods of administration of therapeutic agents include those for oral, pulmonary, nasal, buccal, ocular, dermal, rectal, or vaginal delivery.

Pharmaceutical compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers that can be used include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

A therapeutic kit of the invention comprises a reagent of the invention with one or more additional components, including vials or other containers for storage of a composition according to the invention, instructions for use, and packaging materials.

EXAMPLES

The following Examples are provided to illustrate certain aspects of the present invention and to aid those of skill in the art in practicing the invention. These Examples are in no way to be considered to limit the scope of the invention in any manner.

The examples in this Example section demonstrate favorable outcomes from pharmacokinetic and toxicology studies in animal models of human and animal tumors. The S1P-responsiveness of multiple tumor cell lines, including, but not limited to HeLa cells (human cervical adenocarcinoma), U-87 (human brain glioblastoma), U266 (human multiple myeloma), A549 (human lung carcinoma), U937 (human histocytic lymphoma), MCF-7 (human mammary gland adenocarcinoma), SKOV3 (human ovarian cancer), OVCAR3 (human ovarian cancer), MDA MB 231 (human breast cancer), MDA MB 468 (human breast cancer), H929 (human myeloma), RPMI-8226 (human multiple myeloma, U937 (human lymphoma), SKBR-3 (human breast cancer), and HT-29 (human colorectal adenocarcinoma) cells, is also described. These tumor cell lines represent a spectrum of histological subtypes, genetic aberration and levels of the receptors and enzymes producing and metabolizing S1P. This includes cellular proliferation, motility, invasion, apoptosis, and, for a select group, production of angiogenic factors. It is also demonstrated that many tumor cell lines are also S1P-responsive in their abilities to escape apoptosis induced by the representative chemotherapeutic agents doxorubicin and paclitaxel.

The S1P-induced protection from apoptosis can also be reversed in the presence of an anti-S1P agent, the anti-S1P mAb. An important characteristic of metastatic cancers is that the tumor cells escape contact inhibition and can migrate away from their tissue of origin. The potent ability of S1P to induce cell invasion in multiple tumor cell lines is also reported, as is the ability of the anti-S1P mAb to inhibit the metastatic potential of S1P. In a limited number of cell types, S1P promotes cell proliferation above the already substantial basal levels. Importantly, in vivo xenograft studies demonstrate that the anti-S1P mAb reduces tumor volume in mice given a variety of human cancer cells and one mouse melanoma cell line (B16-F10).

S1P has been shown to promote angiogenesis by the migration of Human Umbilical Vein Endothelial Cells (HUVECs) both in vitro and in vivo. The studies described below confirm that S1P stimulates the formation of capillary-like tubules in vitro and in vivo. Moreover, this process can be inhibited by the anti-S1P mAb. For example, in vivo Matrigel plug assays reveals that the anti-S1P mAb is anti-angiogenic. This was confirmed in vitro using HUVECs. Thus, it has been shown that S1P not only protects HUVECs from doxorubicin and paclitaxel-induced apoptosis, but it also stimulates HUVEC migration and blood vessel formation. Further, examples are presented demonstrating the ability of the anti-S1P mAb to reduce tumor angiogenesis in vivo using a B16-F10 allograft model. All these effects are mitigated by the anti-S1P mAb.

In addition to S1P produced by tumor cells themselves, serum is a rich source of this important tumorigenic factor. Anti-S1P agents such as an anti-S1P mAb can neutralize S1P present not only in the serum but also in the vicinity of solid tumors.

Examples are presented to illustrate the pleiotropic effects of S1P as a tumorigenic growth factor in several tumor-derived human cell lines, suggesting that our anti-S1P mAb may be successfully used in a variety of cancer types. Further, data presented demonstrates that mouse-derived tumors can be treated with the anti-S1P mAb, suggesting a veterinary application of the antibody.

Example 1

Anti-S1P mAb Alone Decreases Tumor Progression

The anti-tumor efficacy of an anti-S1P monoclonal antibody (mAb) was evaluated in two orthotopic breast cancer models and one ovarian cancer model. Tumors were developed by injection of MDA MB 231 human tumor cells into the mammary fat pads of nude (NCr Nu/Nu) mice using standard protocols. After 10 days, when solid tumors had formed (~100 mm$^3$), intraperitoneal treatments of anti-S1P mAb or vehicle alone were initiated. The anti-S1P mAb was administered 25 mg/kg intraperitoneally (i.p.) every other day in saline. Treatments were administered every other day for the duration of the study. Tumor volumes were also determined and recorded every other day. The study was concluded and the animals were sacrificed when the tumors reached their maximal size as defined by IACUC standards (about 1.5 cm$^3$). Tumors were harvested, measured, and processed for immunohistochemical evaluations of micro-vascular changes.

Figure 3:
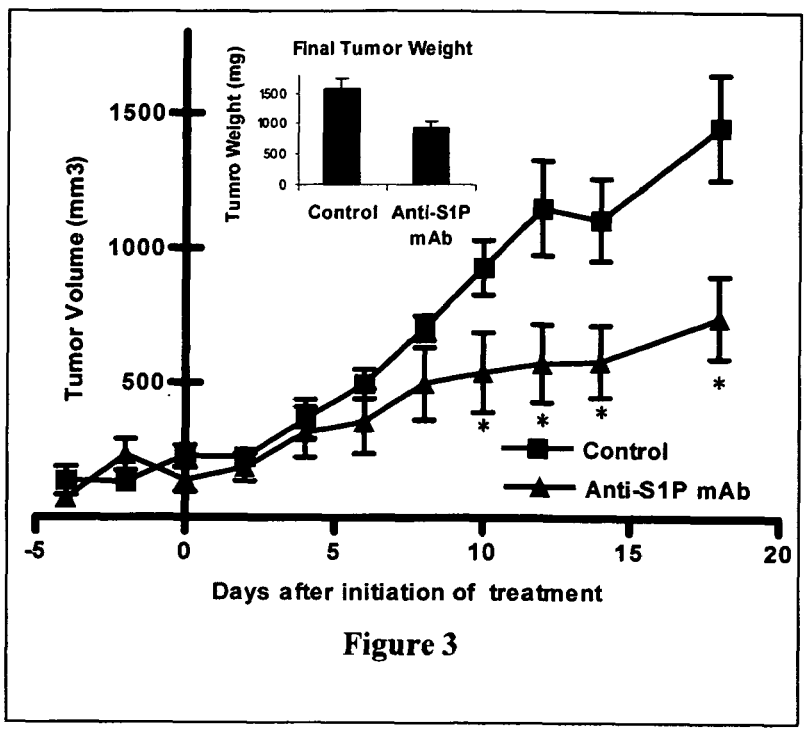
FIG. 3 is a graph showing that an anti-S1P mAb slows MDA MB 231 breast cancer progression. Orthotopic tumor volumes from control and anti-S1P mAb-treated animals are shown. The inset represents final tumor volume (*p<0.01).

FIG. 3 demonstrates the efficacy of the anti-S1P mAb in reducing tumor volume over time. The ability of the anti-S1P mAb to reduce tumor volume was apparent only after the tumors reached approximately 400 mm$^3$. At this point, the tumors from the control animals continued to grow, while the tumors from the anti-S1P treated animals nearly stopped growing. At the end of the study, tumor volumes were reduced by 60% ($p<0.001$ by ANOVA) in the antibody treated animals. The anti-S1P mAb significantly reduced the final tumor weights by an average of 40% when compared to tumors from control treated animals.

Figure 4:
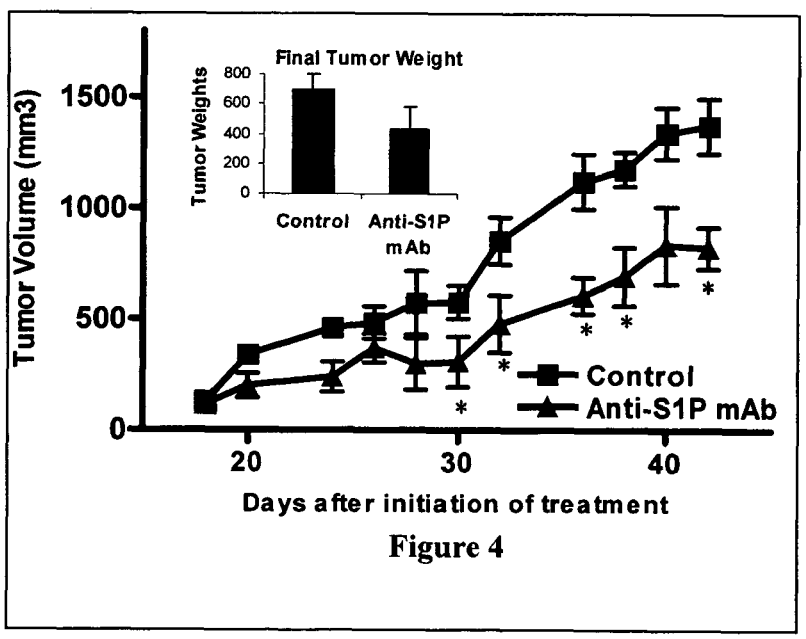
FIG. 4 is a graph showing that an anti-S1P mAb slows MDA MB 468 breast cancer progression. Orthotopic tumor volumes from control and anti-S1P mAb-treated animals are shown. The inset represents final tumor volume (*p<0.01).

Favorable in vivo efficacy data has also been obtained with MDA MB 468 human breast cancer cells in an equivalent orthotopic mammary fat pad model (FIG. 4). In this model, a 40% reduction in average tumor volume was observed for the antibody-treated animals. The reduction in the size of tumors from animals treated with the anti-S1P mAb correlated to reduced serum levels of the pro-angiogenic and tumorigenic factor, IL-8. Thus, in both of the xenograft models tested, the anti-S1P antibody markedly inhibited tumor growth.

Example 2

Anti-S1P mAb Inhibits Tumor Angiogenesis in Vivo

Figure 5:
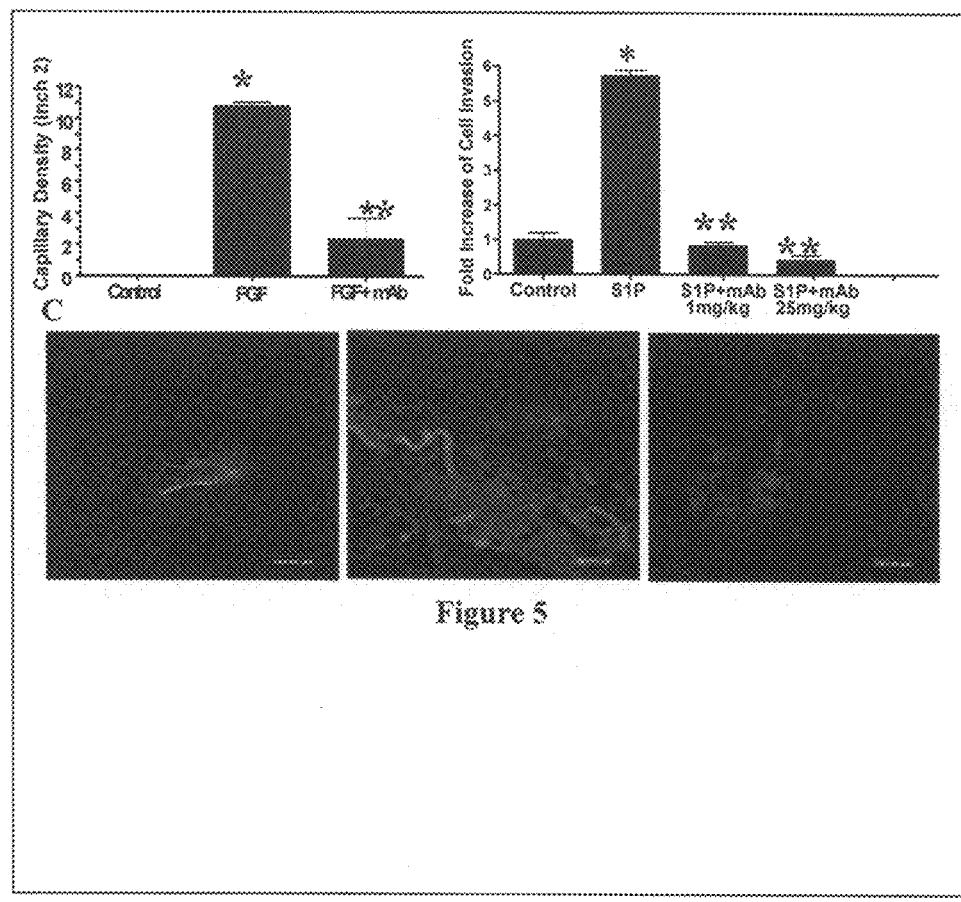
FIG. 5 shows data indicating that S1P and other growth factors stimulate micro-vascularization of implanted Matrigel plugs in vivo, effects which can be potently inhibited by an anti-S1P mAb. Panel A: Quantification of relative fluorescence from Matrigel plugs after 10 days as an indicator of vascularization. Panel B: H&E staining of Matrigel plug cryosections to determine cell invasion. Values are expressed as fold increase over controls. Panel C: Cryosections of Isolectin-FITC-stained Matrigel plugs demonstrates the micro-vascularization of plugs containing hGF and the reduction of blood vessels in plugs containing hGF from mice treated with 25 mg/kg of the anti-S1P mAb. T-test was used to determine significance. *p<0.01 for control vs. hGF or S1P; **p<0.01 for hGF or S1P vs. hGF or S1P+mAb.

To investigate the ability of anti-S1P mAb to neutralize the pro-angiogenic effects of S1P, an in vivo Matrigel Plug assay was used. This assay is a well-established animal model for tumor angiogenesis using Matrigel, a proprietary mixture of tumor remnants including basement membranes derived from mouse tumors. When Matrigel is injected subcutaneously (s.c.) into an animal, it forms a 'plug'. Upon addition of angiogenic factors, the plug is invaded by vascular endothelial cells, which then form capillary-like blood vessels. Matrigel can be prepared either alone or mixed with recombinant growth factors (rGF) such as FGF or VEGF as a pro-angiogenic compounds, then injected s.c. in the back of 6 week old C57B1/6N female mice. Endogenous S1P from the blood and surrounding tissue could supply the plug with an additional pro-angiogenic stimulus. Based on the in vivo performance characteristics of the antibody (see below), it was presumed that treatment of mice with the anti-S1P mAb would reduce available serum and tissue S1P levels and, consequently, reduce the concentration of endogenous S1P available to the plug. In these experiments, the ability of the antibody to reduce angiogenesis in an optimally stimulated plug (added protein growth factors, plus endogenous S1P) was studied. One group of mice that received Matrigel containing hGF also received intraperitoneal (i.p.) injections of anti-S1P mAb every 48 hr. starting 1 day prior to Matrigel implantation. Each treatment group (Matrigel, Matrigel plus hGF, or Matrigel plus hGF with mAb treatment) consisted of a minimum of six mice. After 10 days, the mice were heparinized and injected with the fluorescent lectin, Isolectin B4-FITC, which binds to adhesion molecules expressed by vascular endothelial cells. The plugs were then excised. Visual examination of the plugs revealed that the control (Matrigel only) plugs were colorless, whereas those plugs containing hGF had clearly undergone angiogenesis as indicated by the red, bloody appearance. The plugs from animals treated with the anti-S1P mAb and containing hGF were colorless, thus suggesting an inhibition of micro-vascularization. The plugs were then embedded in OCT freezing medium and sectioned. Microvascular density was qualitatively accessed by lectin-FITC stained vessels, as shown in FIG. 5. Blood vessel staining was sporadic in control (untreated) plugs, whereas the plugs containing hFGF demonstrated significant evidence of vascularization (middle photo of panel C). The plugs from mice treated with the anti-S1P mAb demonstrated a significant reduction in blood vessel formation compared to the hGF plugs from untreated mice (no mAb). Quantification of stained vessels revealed an 11-fold decrease in neo-vascularization of hGF containing plugs from animals treated with the antibody in comparison to non-treated animals (FIG. 5). This evaluation further demonstrates the ability of endogenous serum and tissue S1P to enhance micro-vascularization as well as the ability of the anti-S1P mAb to neutralize endogenous S1P's pro-angiogenic effects in vivo.

These results demonstrate the anti-angiogenic effects of the anti-S1P mAb in vivo and the dramatic effects of the anti-S1P mAb in reducing tumor progression without the benefit of cytotoxic chemotherapeutic agents. While not wishing to be bound to a particular theory, this data reveals that the anti-tumorigenic effects of the anti-S1P mAb may be due to the mitigation of the angiogenic effects of S1P that would normally promote tumor progression. Thus, some effective cancer treatments will result from the additive effects of the anti-S1P agent in combination with one or more other cytotoxic agents. In vitro and in vivo work demonstrating the additive anti-tumor effects of a combination treatment are described below.

Example 3

In Vivo Pharmacokinetics and Toxicology

Figure 6:
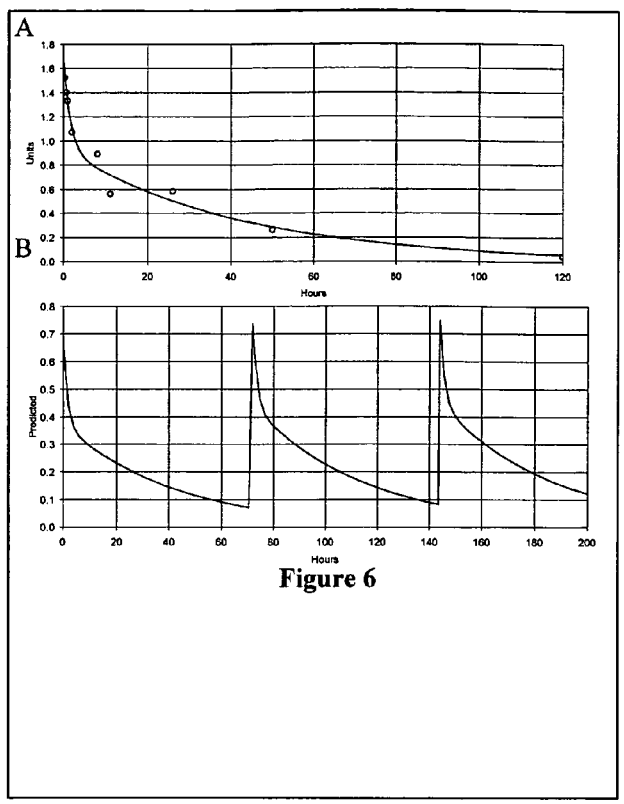
FIG. 6 shows two graphs, A and B, that establish that the half-life of a particular anti-S1P mAb in mice is 26 hr. Panel A. Mice were treated with a bolus dose of 25 mg/kg of the anti-S1P mAb. The concentration of mAb in the serum at designated time points was determined using a competitive ELISA. Using a two-compartment calculation, the half-life of the antibody was determined to be 26 hr. This experiment was repeated three times with duplicate mice at each time point. Panel B. Simulation of administration of 10 mg/kg anti-S1P mAb, dosed every three days for eight days.

Prior to initiating in vivo studies, the toxological and pharmacokinetic characteristics of the anti-S1P mAb were determined in mice. The half-life of the antibody was measured to determine how to optimally dose the animals to maintain a reasonable blood level of the anti-S1P mAb. Mice were dosed with 25 mg/kg of the anti-S1P mAb intravenously (i.v.) and bled at designated time points. A competitive ELISA employing a Biotin-labeled anti-S1P mAb was used to determine the concentration of antibody remaining in the mouse blood between 20 min. and 120 hr. after the bolus dose of antibody. FIG. 6 demonstrates that the serum half-life of the mAb was approximately 20-25 hr. In addition to i.v. injections, mice were administered a bolus dose of anti-S1P mAb by intraperitoneal (i.p.) injection. After 20 minutes, over 95% of the antibody appeared in the bloodstream. Taken together, these data indicate that mice can effectively be dosed either i.p. or i.v. with the anti-S1P mAb.

Due to the pleiotropic nature of S1P, potential adverse effects on physiological functions that might be caused by a reduction of systemic S1P as a result of treatment with the anti-S1P mAb were investigated. Mice were treated with 1, 3, 10, 30, or 50 mg/kg of the anti-S1P mAb or vehicle (PBS) for seven consecutive days by tail vein injection. Due to the long half-life of the antibody, simulations of the dosing regimen indicated that the animals accumulated over twice the amount of antibody over the 7 days. Twenty-four hours after the final treatment, the mice were sacrificed, biological fluid was collected, and organs were harvested. Even at the highest dose, all chemical and CBC panel analyses were within normal ranges. Furthermore, histopathological examination by a board certified veterinary pathologist revealed no lesions or other pathological changes in the liver, kidney, heart, lungs, or spleen of mice in any treatment group. Throughout the duration of the study, mice in all treatment groups consumed similar amounts of food and water and socialized no differently than control animals. Body weights and activity levels were also normal. Therefore, at all doses tested, including 50 mg/kg, the antibody appeared to be well-tolerated.

The information from the pilot pharmacokinetic and toxicity studies provided insight as to how to dose animals in animal efficacy studies. A simulation of dosing of 10 mg/kg anti-S1P mAb every third day demonstrates the constant presence of the antibody in the mouse that does not accumulate appreciably over time (FIG. 6).

Example 4

Antibody Characteristics

Figure 7:
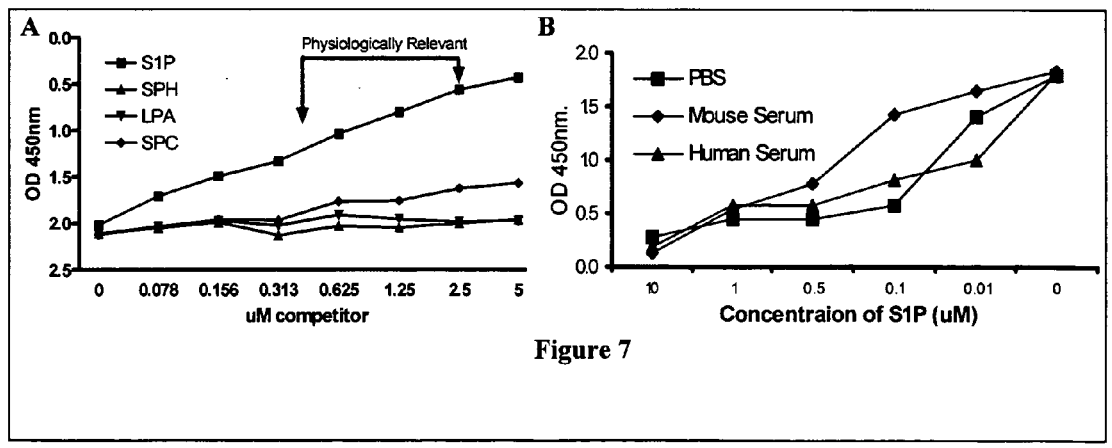
FIG. 7 shows two graphs, A and B, demonstrating that an anti-S1P mAb is specific and sensitive for S1P and does not recognize structurally similar bioactive lipids. Panel A shows the results of a competitive ELISA with S1P, SPH, LPA, or SPC competing for the mAb binding to S1P on the plate. Only free S1P can compete for binding, demonstrating the specificity of the anti-S1P mAb. Panel B shows the results of a competitive ELISA demonstrating the sensitivity of the anti-S1P mAb. This anti-S1P mAb can detect a difference of 5 nM S1P.

One important performance characteristic of an antibody is its specificity towards its antigen, i.e., does it specifically react with its intended target. FIG. 7 shows a competitive ELISA using the anti-S1P mAb tested against a gold-standard S1P sample (obtained from Avanti Polar Lipids and confirmed by HPLC and mass spectroscopy) as well as several other lysolipid controls. Importantly, the antibody demonstrated no cross-reactivity to sphingosine (SPH), the immediate metabolic precursor of S1P. Moreover, the anti-S1P mAb did not recognize lysophosphatic acid (LPA) or sphingosylphosphorylcholine (SPC). Both LPA and SPC are structurally similar to S1P.

Another important performance characteristic of a good therapeutic antibody is that it can recognize the target (i.e., S1P) in the physiological range. Studies using the industry standard HPLC technique for measuring serum S1P revealed that normal serum S1P levels are within the 400-700 pmol/mL range, while patients with significant coronary artery disease display higher serum S1P levels, in the 900-2,500 pmol/mL range. Data indicates that ascites from ovarian patients contain a large amount of S1P that is close to serum S1P levels. FIG. 7 demonstrates the dynamic range of the anti-S1P mAb used in these examples, and indicates that the antibody is capable of recognizing S1P at both normal and clinically relevant S1P concentrations. Consequently, the anti-S1P mAb has a dynamic range that is sensitive as well as specific, i.e., it is "specifically reactive" with its intended target. A comparison between the industry standard HPLC measurement of human serum S1P from a normal volunteer and ELISA-based measurements using the anti-S1P mAb showed good correspondence between the two methods, thus validating the use of an ELISA as an accurate platform for S1P determination.

An additional important characteristic of an antibody is its ability to recognize its ligand in an in vivo environment. Accordingly, the ability of the anti-S1P mAb to recognize and selectively absorb S1P from human and mouse serum was studied in an in vitro assay utilizing both radioactivity and mass spectrometry analysis. The mAb was efficiently able to absorb up to 88% and 77% of $^3$H-S1P added to PBS and mouse serum, respectively. The difference in the ability of the mAb to absorb similar levels of the $^3$H-S1P in the mouse serum when compared to the control (PBS) was most likely due to the mAb also binding to endogenous S1P, which is present in large concentrations in mouse serum. These data are consistent with in vitro cellular bioassays performed in serum plus in vivo efficacy experiments, demonstrating that the mAb can effectively neutralize S1P in serum.

Taken together, these results demonstrate the successful development of biospecific monoclonal antibody to S1P that is both specific and sensitive. Thus, the mAb, and other agents capable of specifically reacting with S1P, can be used therapeutically as a molecular "sponge" or "sink" to efficiently and selectively absorb S1P from serum, thereby reducing its effective concentration in extracellular fluids in vivo. In addition, the anti-S1P mAb (and like reagents) can be used as a detection reagent in an assay to detect (quantitatively, semi-quantitatively, or qualitatively) levels of S1P (or other target analytes) in biological samples (e.g., tissue samples (e.g., from biopsies) or bodily fluids (e.g., blood, ascites, serum, lymph, saliva, urine, cerebrospinal fluid, etc.). Evaluation of S1P as a biomarker could be used in conjunction with genomic profiling of tissue S1P receptor levels and levels of SPHK to stratify patients by there dependence on S1P for tumor growth. Such assays will have application in "theranostic" platforms in which a patient's serum, ascites, or tumor biopsy material would be measured for S1P content, preferably paired with genomics analysis, thereby allowing it to be predicted which patients would most benefit from a therapeutic treatment that employs the detection reagent formulated as a therapeutic in a subsequently delivered therapy.

Example 5

Anti-S1P mAb Increases Chemotherapeutic-Induced Tumor Cell Death

Figure 8:
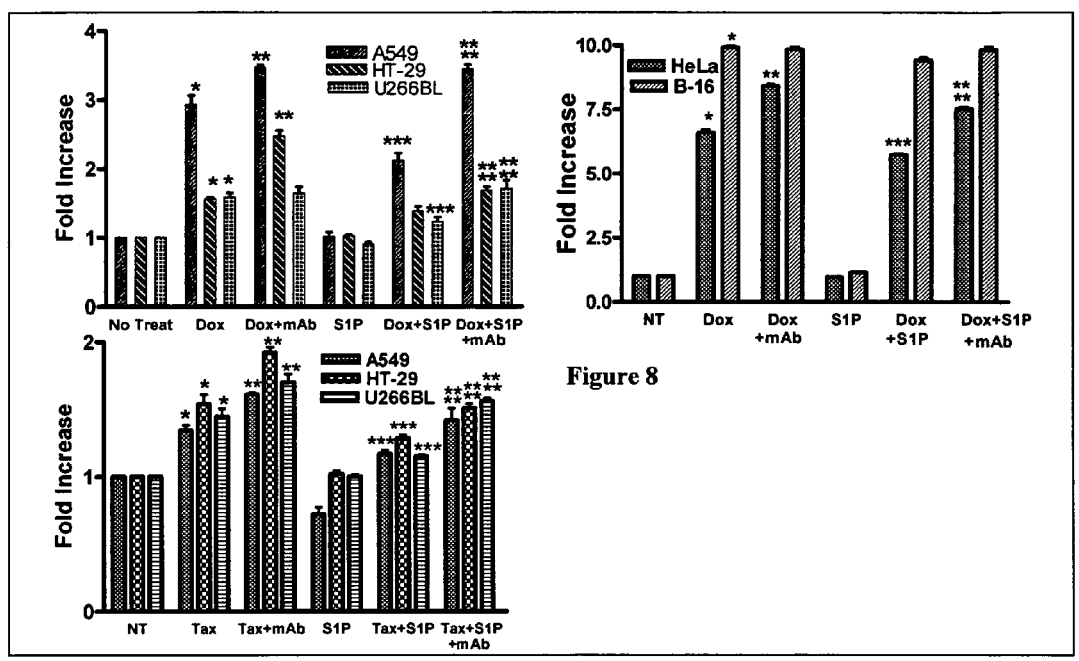
FIG. 8 shows three bar graphs, plotting the fold-increase in tumor volume against treatment regimen. These data show that S1P specifically protects multiple tumor cells from death in the presence of chemotherapeutic agents, but that this protective effect can be reversed by the anti-S1P mAb used in these experiments. Cells were treated for 48 hrs with 500 nM paclitaxel (Tax) or 1 μM doxorubicin (Dox) and +/−100 nM S1P and the anti-S1P mAb (1 μg/mL). Cell death was assayed by detection of activated caspase-3. All data are the means±SEM of at least three independent experiments. P<0.01, * for NT vs. Dox, Dox vs. Dox+mAb, Dox vs. Dox+S1P, ****Dox+S1P vs. Dox+S1P+mAb.

In addition to the pro-angiogenic properties of S1P (see above), it has been demonstrated that the actions of S1P in promoting tumor growth can be attributed to the molecule's ability to directly promote cell proliferation and to protect the cells against pro-apoptotic chemotherapeutic agents. The ability of S1P to block the up-regulation and activation of the apoptotic terminal effector, caspase-3, has been studied in several tumor cell lines when exposed to clinically-relevant levels of the chemotherapeutic agents, paclitaxel (Taxol) and doxorubicin (Andriamycin). FIG. 8 demonstrates the ability of S1P to protect A549, HT-29, U266BL, and HeLa cells from apoptosis triggered by these chemotherapeutic agents. FIG. 8 shows that paclitaxel and doxorubicin potently induced caspase-3 activation by 50-1000% after 48 hr. of treatment in media containing 10% serum. In an attempt to promote conditions resembling physiological levels of S1P, the 10% serum was supplemented with additional S1P (100 nM), and then the cells were treated with cytotoxic agents. In comparison to cells treated with 10% serum, cells supplied with additional exogenous S1P were protected from paclitaxel- and doxorubicin-induced apoptosis. This was demonstrated by the significant ($p<0.001$) reduction in caspase activity seen in the presence of the added sphingolipid. Importantly, the mAb was effective in mitigating the protective effects of S1P in the presence of the chemotherapeutic agents. Even in the absence of added S1P, paclitaxel- and doxorubicin-induced caspase activation was enhanced by the anti-S1P mAb (25% and 50-200% increases, respectively), indicating that the protective anti-apoptotic effect of endogenous S1P was eliminated by selective antibody absorption of S1P present in the serum. Considering that serum has substantial endogenous S1P, the efficacy of the antibody in the absence of added S1P (third set of bars) shows that endogenous levels of S1P in the serum were sufficient to afford some protection against doxorubicin or paclitaxel-induced cell death.

The specificity of the anti-S1P mAb was demonstrated in control experiments utilizing a structurally similar bioactive lipid mediator and a nonspecific isotype matched monoclonal antibody. Experiments utilizing the A549, HT-29 and U266BL cell lines, LPA failed to reduce caspase activation. Moreover, the nonspecific monoclonal antibody failed to neutralize S1P-responsiveness, showing specificity of the anti-S1P mAb in mitigating S1P effects.

Similar data demonstrated the anti-apoptotic effects of S1P in U266BL, MCF-7, and HT-29 cells. However, not all tumor cell lines respond to S1P. For example, mouse melanoma B16-F10, human lymphoma U937, and human ovarian MDA MB 2774 carcinoma cells did not respond to S1P when evaluated for the ability of the lipid mediator to protect those cell types from doxorubicin- or paclitaxel-induced cell death. Moreover, the anti-S1P mAb did not increase the killing potential of the chemotherapeutic agents, thus demonstrating the lack of effect that S1P exerts on these tumor cell lines.

Example 6

Anti-S1P mAb Inhibits Release of Tumor-Promoting Cytokines and VEGF

Figure 9:
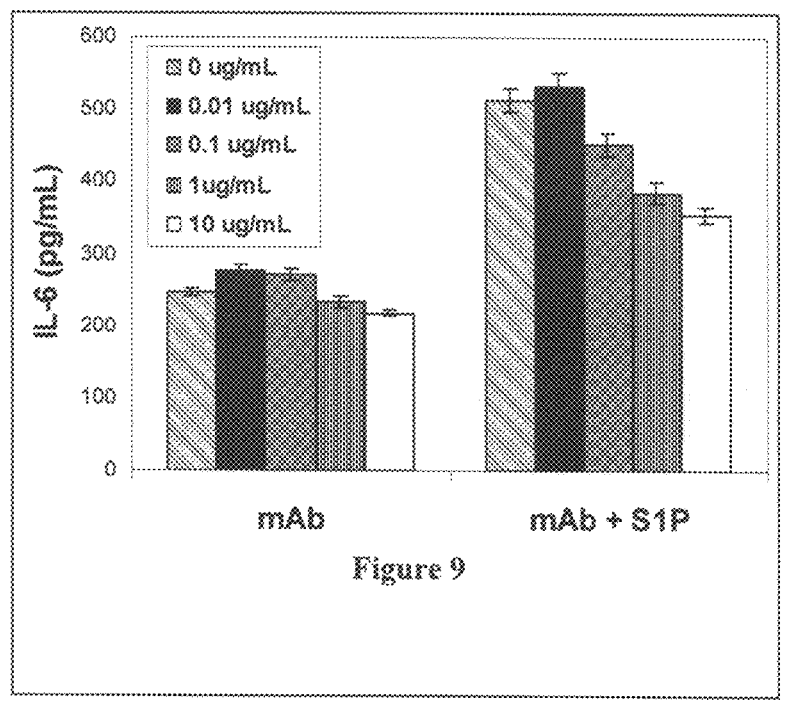
FIG. 9 shows a histogram that shows S1P-induces expreassion of IL-6 from OVCAR3 cells is mitigated by an anti-S1P mAb (0-10 μg/mL) and +/−10 μM S1P. S1P induces the release of IL-6 and is reversed by the mAb.

In animal models, expression of interleukin-6 and 8 are associated with increased tumorigenicity, ascites formation, angiogenesis, and invasiveness of ovarian cancer cells. In ovarian cancer patients, serum levels of IL-6 are elevated by several magnitudes. Taken together, these studies indicate that IL-6 is an important modulator or, at least, an indicator of ovarian cancer progression. For these reasons, it was decided to investigate whether an anti-S1P monoclonal antibody could reduce IL-6 production as a measure of the antibody's ability to reduce ovarian cancer progression. For these studies, it was demonstrated that 10 µM S1P could stimulate IL-6 release from ovarian cancer cells. Culture supernatants of ovarian cancer OVCAR3 cells, treated with or without S1P, were collected and analyzed for IL-6 release into the cell-conditioned media using an ELISA. As FIG. 9 demonstrates, S1P increased the expression of IL-6 by an average of 275% when compared to non-treated cells. For cells pre-treated with the anti-S1P mAb, IL-6 expression was significantly reduced. Increasing amounts of the mAb (from 0.01-10 µg/mL), resulted in a dose-dependent loss of IL-6 expression. Similar significant results were obtained utilizing two other neo-vascularization factors, IL-8 and VEGF, using several tumor cell lineages. These data show that the blockade of growth factor release is an additional effect of anti-S1P agents.

Example 7

Anti-S1P mAb Decreases S1P-Stimulated Increases in Cancer Cell Proliferation

Figure 10:
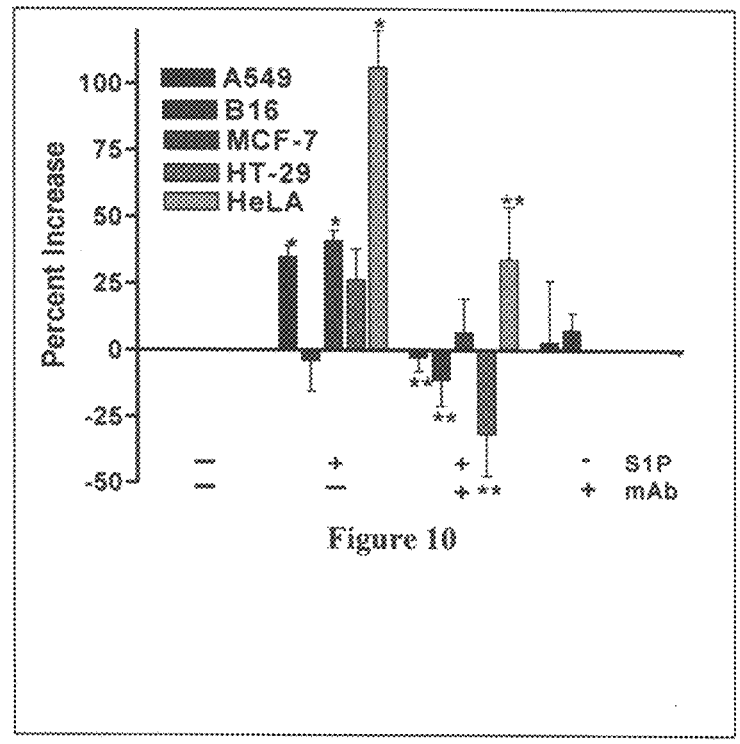
FIG. 10 shows data demonstrating that S1P stimulates tumor cell proliferation, which activity can be quenched by an anti-S1P monoclonal antibody. Cells were incubated in the presence or absence of 100 nM S1P and 1 ug/mL anti-S1P mAb. The graph show the percent increase (above control), as determined by 3[H]-Thymidine incorporation after 48 h. Data sets are the mean±SEM of three experiments performed in triplicate. Students T-test indicated p<0.001. * NT vs. S1P and ** S1P vs. S1P+mAb.

FIG. 10 demonstrates the ability of S1P to increase proliferation of selected human-derived tumor cell lines including A549, HT-29, MCF-7 and HeLa cells by $^3$H-thymidine incorporation studies. DNA synthesis was significantly ($p<0.05$) increased in cells treated with 100 nM S1P when compared to non-treated control cells in each of these cancer cell lines. Even though tumor-derived cells normally have high basal levels of proliferation, S1P appears to augment proliferation in most tumor cell lines. Importantly, the increase in DNA synthesis stimulated by S1P was mitigated by the addition of 1 µg/ml of the anti-S1P mAb. Similar data were obtained with the OVCAR3, MDA MB 273, and MDA MB 468, tumor cell lines using crystal violet staining.

Example 8

Anti-S1P mAb Decreases S1P-Stimulated Increases Tumor Cell Metastatic Potential

Figure 11:
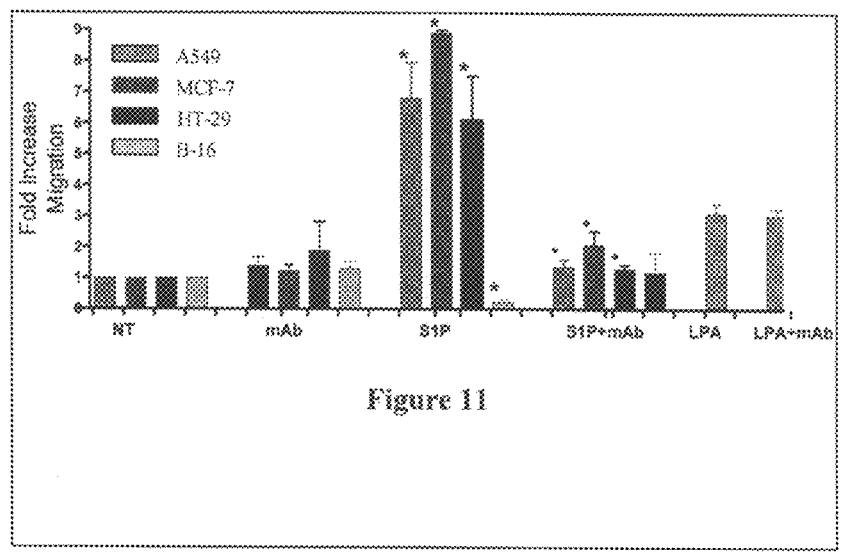
FIG. 11 shows data demonstrating that S1P stimulates tumor cell invasion of Matrigel, but this activity can be mitigated by an anti-S1P monoclonal antibody. Cells were treated with 1 μM S1P, with or without an anti-S1P mAb (1 μg/ml) for 20-22 hrs in a Matrigel chamber. The number of cells that migrated to the Matrigel membrane was counted in five fields. Data are the means±SEM of three independent experiments. Statistical significance using the T-test between groups is as follows: p<0.01 for * NT vs. S1P and ♦S1P vs. S1P+mAB.

An important characteristic of metastatic cancers is that the tumor cells acquire the ability to migrate and invade tissues. S1P has been shown to promote metastatic potential in breast cancer, glioblastoma, and melanoma cells using in vitro cell invasion assays. It was decided to evaluate whether the anti-S1P monoclonal antibody could block S1P-mediated cell migration. To evaluate the chemotactic effects of S1P on tumor cells, an in vitro Matrigel cell invasion assay commonly used in chemoinvasion studies was used. As shown in FIG. 11, treatment with levels of S1P found in human serum induced an increase in A549, HT-29 and MCF-7 cell invasion through the Matrigel matrix. A 6 to 9-fold increase in cell migration was obtained with 1 µM S1P when compared to non-treated control cells. Addition of the monoclonal anti-S1P antibody reduced tumor cell invasion to control levels. Four control experiments demonstrated the specificity of these effects. First, incubating A549 cells with LPA had no effect upon cell migration, demonstrating S1P's specific effect on this cell line. Second, addition of non-specific mouse IgG did not inhibit S1P-induced cell migration. Third, titrating down the concentration of anti-S1P mAb from 1 µg/mL to 0.001 µg/mL reduced the ability of the antibody to effectively neutralize all of the S1P. Fourth, B16-F10 cells (previously determined to be unresponsive to S1P; see Example 5) did not migrate upon incubation with S1P.

Example 9

In vitro Demonstration that Anti-S1P mAb Blocks Tumor Angiogenesis

The process of neo-vascularization is vital to the survival and growth of a tumor. Neo-vascularization is dependent upon the invasion, vessel formation, and survival of endothelial cells inside or adjacent to the growing tumor. This series of experiments describes the evaluation of the tumor-promoting ability of S1P to stimulate neo-vascularization in terms of tube formation, migration, and survival against chemotherapeutic agents.

Figure 12:
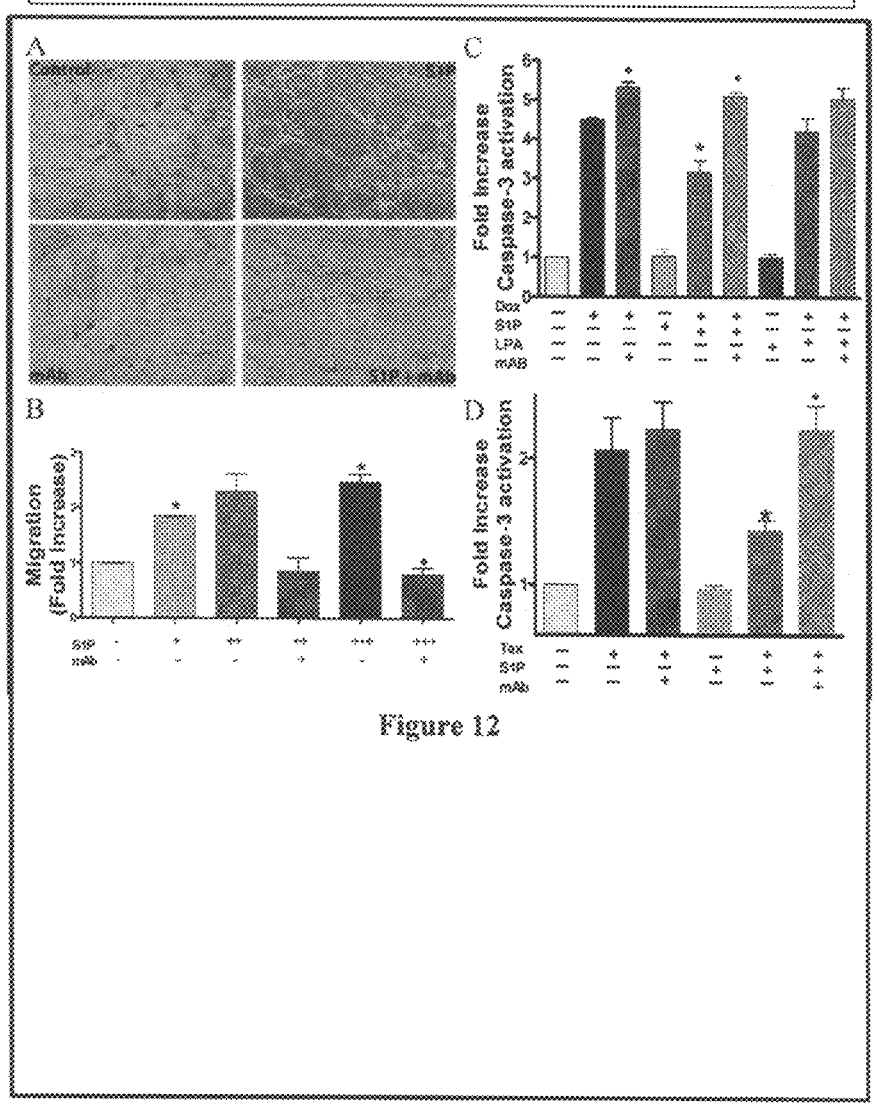
FIG. 12 shows data demonstrating that S1P promotes neovascularization through induction of HUVEC tube formation, migration, and protection from death, which activity can be reduced by an anti-S1P mAb. Panel A: Representative micrographs of HUVECs seeded on Matrigel and incubated for 6 hr. to evaluate tube formation. Panel B: HUVECs were treated with 1 μM S1P+/−the anti-S1P mAb (1 μg/ml) for 6 hr. in a Matrigel invasion chamber. The number of cells that migrated to the Matrigel membrane was counted in five fields. Panels C and D: HUVECs were treated for 24 hr. with 50 nM paclitaxel (Tax) or 1 μM doxorubicin (Dox) and +/−S1P (1 μM) and the anti-S1P mAb (1 μg/mL). Cell death was assayed by detection of activated caspase-3. All data sets are the means±SEM of three independent experiments performed in triplicate. For panels B-D, significance using the T-test was at least p<0.01, * NT vs. S1P or Dox/Tax vs. Dox/Tax+S1P, ♦S1P vs. S1P+mAbor Dox/Tax+S1P vs. Dox/Tax+S1P+ mAb.

S1P has been shown to promote the migration of Human Umbilical Vein Endothelial Cells (HUVECs) and the formation of de novo blood vessel formation in vitro using Matrigel and other similar assays. HUVECs isolated from human umbilical cords form tubular capillary-like structures when provided with critical growth factors. While antibodies directed against key protein growth factors like VEGF and FGF neutralize blood vessel formation and tumor growth, the anti-angiogenic effects of neutralizing antibodies directed against sphingolipid growth factors have not been examined previously. FIG. 12A demonstrates that HUVECs seeded onto growth factor-reduced Matrigel formed multiple capillary-like structures in the presence of physiologically relevant serum/plasma concentrations of S1P (400-700 pmol/mL). The HUVECs failed to form capillary-like structures in the absence of S1P. Moreover, a monoclonal antibody directed against S1P substantially reduced the formation of the typical capillary-like structures.

The ability of endothelial cell to migrate to the site of a tumor is also an important process during angiogenesis. The ability of physiological concentrations of S1P to stimulate HUVEC migration in the Matrigel chemoinvasion assay described above was determined. FIG. 12B demonstrates the potent ability of 0.1-1 µM S1P to stimulate HUVEC migration 2-2.5 fold over non-treated HUVECs. Importantly, this stimulation of migration was completely neutralized by the addition of the anti-S1P monoclonal antibody.

The ability of endothelial cells to undergo angiogenesis and feed a growing tumor is also dependent upon the cells' ability to circumvent cell death induced by chemotherapeutic agents. Panels C and D of FIG. 12 demonstrate the ability of S1P to potently protect HUVECs from cell death as assayed by caspase-3 activation. The ability of S1P to protect cells from death was reversed by incubation with the anti-S1P mAb. Furthermore, similar to the assays described above, the anti-S1P mAb enhanced caspase-3 activation induced by doxorubicin and paclitaxel. These experiments were performed in the presence of 20% serum, demonstrating the ability of endogenous S1P in serum to protect HUVECs from cell death induced by chemotherapeutic agents.

These studies confirm that S1P is a potent pro-angiogenic growth factor that can influence de novo blood vessel growth and protect vascular endothelial cells from cytotoxic agents. These results demonstrate that an anti-S1P agent can exert an anti-angiogenic effect by several mechanisms, including one that enhances chemotherapy-induced cell death of endothelial cells. Moreover, such agents, in combination with standard chemotherapeutic agents, can act to reduce angiogenesis and slow cancer progression in the clinic. In sum, these results demonstrate that S1P is a pleiotropic tumorigenic growth factor that has profound effects on tumor cell proliferation, invasion (i.e., metastatic potential), neo-vascularization, and protection from apoptosis. In addition, S1P protects most cells types against apoptotic chemotherapeutics. Even though cell proliferation was significantly stimulated by S1P, the effects of S1P on the other parameters were much more dramatic and uniformly applicable to most of the cell types studied. The pro-angiogenic effects of S1P were dramatic, and anti-S1P agents such as the anti-S1P monoclonal antibody described herein block all of these effects. Additionally, the results demonstrate that agents such as the anti-S1P monoclonal antibody can block the production of other pro-angiogenic growth factors, providing an additional therapeutic mechanism for our anti-S1P mAb in halting tumor progression.

The efficacy of an anti-S1P agent to block the micro-vascularization of tumors as well as inhibiting tumor cell growth (volume and weight) has been demonstrated. Compelling data from screens of several cell lines derived from a variety of solid and circulating tumor types shows that anti-S1P agents (e.g., antibodies) can be useful in the treatment of many cancer types, particularly those that have a dependence on angiogenesis. The favorable in vivo pharmacokinetic and toxicology profiles of the agents such as the anti-S1P monoclonal antibody described herein further demonstrate that anti-S1P agents are likely to be drugable in humans.

Example 10

Anti-S1P mAb Blocks Tumor Angiogenesis in an in vivo Allograft Model

Growing tumors depend upon blood vessel growth. Agents that can inhibit this process without significant toxicity could serve as potent new anti-tumor therapeutics. Although the anti-VEGF antibody therapeutic, Avastin, was recently approved for clinical use for colon cancer therapy, Avastin has not proven effective in lung and breast cancer clinical trials. Therefore, additional approaches to inhibit tumor angiogenesis are still needed. As shown in Example 9, one such approach is to block the pro-angiogenic effects of S1P. The anti-S1P mAb has been shown to potently inhibit S1P-induced endothelial cell migration, capillary growth, and cell survival in vitro. The anti-S1P mAb has also been shown to neutralize S1P's ability to enhance de novo blood vessel formation in the in vivo murine Matrigel plug model of angiogenesis. Accordingly, the efficacy of anti-S1P to reduce the micro-vascularization of tumors in two in vivo murine models was investigated. As S1P has been shown to promote or enhance angiogenesis, the anti-S1P mAb was expected to suppress de novo blood vessel formation, and hinder tumor growth.

Based upon the in vitro studies described in Examples 5 and 8, it was known that the murine melanoma tumor-derived cell line B16-F10 was unresponsive to the direct effects of S1P. S1P did not induce proliferation, invasion, or protection from cell death in these cells, as it does in most other tumor cells. Thus, it was hypothesized that any anti-tumor effect of the anti-S1P mAb on B16-F10 tumors would arise not from inhibition of S1P-induced tumor growth, but from an inhibition of S1P-enhanced tumor-associated angiogenesis. An inhibition of neo-vascularization in the growing tumor would, thus, significantly slow tumor progression. Therefore, a study was undertaken to investigate the ability of the anti-S1P mAb to retard melanoma tumor growth after an orthotopic xenograft placement of the B16-F10 cells in mice.

In this model, tumors were developed in 4 week old female C57B1/J6 mice (the strain from which the melanoma cells were originally isolated) by implantation of B16-F10 cells into the right flanks of the mice. Tumors were allowed to establish to a volume of 100 mm$^3$, as determined by caliper measurements. When the tumors began reaching the desired volumes, mice were computer-randomized into treatment groups (n=6-8). Mice with tumors between 75-150 mm$^3$ were selected for treatment. All animals containing tumors out of this volume range were not included in this study. The selected mice were then injected i.p. every three days with either the anti-S1P mAb (25 mg/kg), an isotype matched non-specific mAb (25 mg/kg; directed against a plant pathogen), or saline. All treatments were double-blinded. Tumor volumes were measured independently every day by two people and averaged. When tumor volumes began reaching the maximal size (about 1.8 cm$^3$ by IACUC standards), all animals were sacrificed. Final tumor volumes and weights were recorded. Only after all data were analyzed was the study un-blinded.

Figure 13:
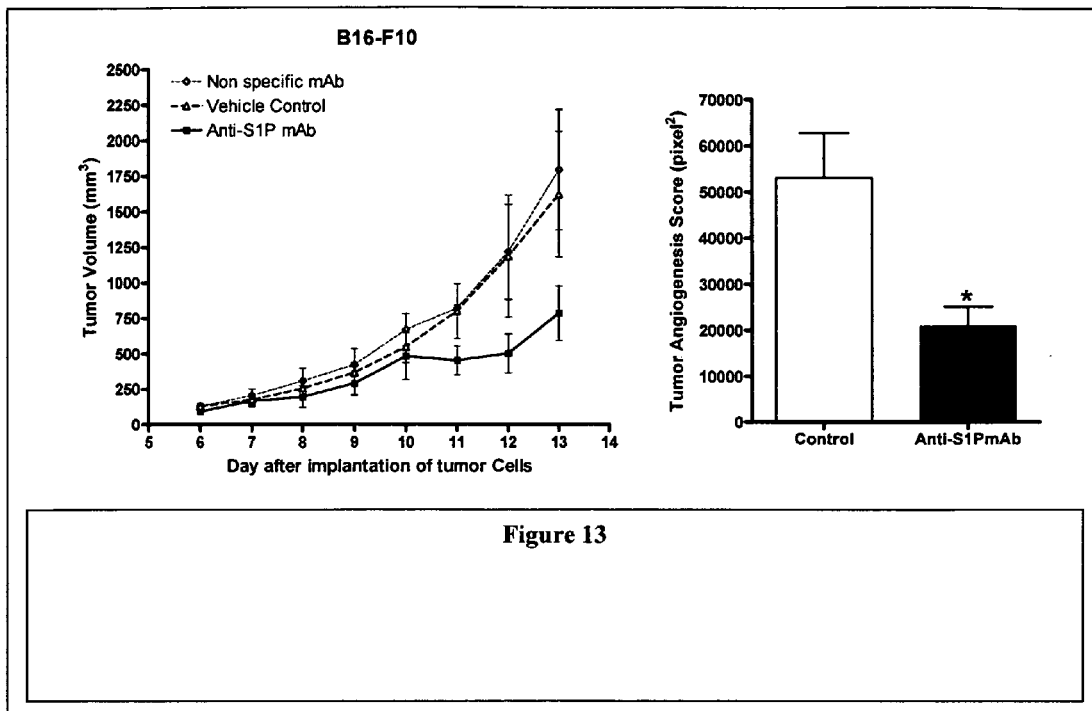
FIG. 13 shows that the anti-S1P mAb significantly reduces tumor angiogenesis. Murine melanoma (B16-F10) tumors were orthotopically established in C57BL/J6 mice. Represented are the average tumor volumes over time (A) and final tumor weights (B). Treatments consisted of the anti-S1P mAb (n=8), a non-specific mAb (n=7), or saline (n=6). Data are the mean+/−SEM. Statistical significance was determined by ANOVA. Panel B shows a quantification of the tumor angiogenesis based on isolectin-B5 staining of excised tumors.

FIG. 13A demonstrates a 60% reduction of tumor volume over time from mice treated with the anti-S1P mAb in comparison to those animals treated with saline or the non-specific mAb. FIG. 13B confirms the inhibition of tumor progression occurred by the reduction of neovascularization of the tumor. The reduction of tumor progression is believed to be directly related to the anti-angiogenic effects of the anti-S1P mAb. Further, these mice were not immune-compromised, indicating that blocking sphingolipid action can reduce tumor progression in normal animals. In addition, this study demonstrates that mouse-derived tumors can be treated with an anti-S1P antibody, indicating that the antibody will also be useful for veterinary applications aimed at cancer treatment, particularly in companion animals and livestock.

Example 11

Figure 14:
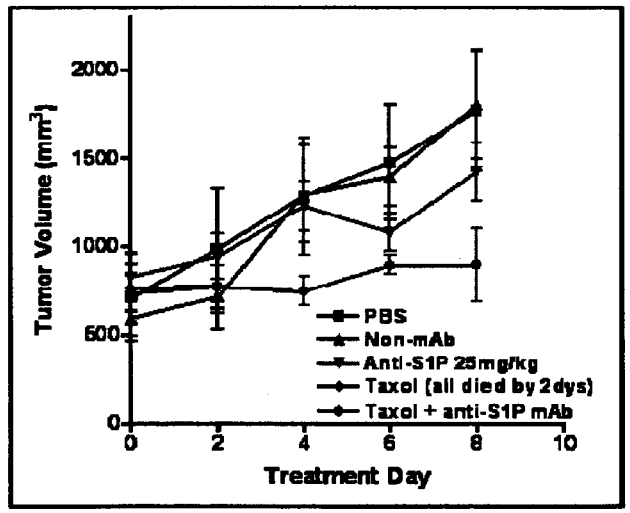
FIG. 14 charts data for MDA MB 231 cells treated with anti-S1P mAb alone (25 mg/kg i.p. every other day) or in combination with a bolus dose 20 mg/kg Taxol (plaxitaxel).

Anti-S1P mAb in Combination with Chemotherapeutic Agents Decreases Tumor Progression While Example 1 demonstrates that an anti-S1P mAb is efficacious in reducing tumor size when administered alone, the treatment for human cancers may be more successful, or be applied to treat more types of cancer, if an agent that binds to and reduces the effective in vivo concentration of S1P is given in combination with one or more chemotherapeutic agents or as an adjunct to procedures such as surgery and radiation therapy. Indeed, when mice having fairly large tumors (for example, 700-800 mm$^3$; established by implanting MDA MB 231 mammary carcinoma cells) were treated with the anti-S1P mAb (25 mg/kg every other day) either alone or in combination with one dose of Taxol (paclitaxel) at a bolus dose of 20 mg/kg, the combination demonstrated a synergistic effect in that the antibody-treated mice showed almost no further growth. See FIG. 14. Moreover, addition of the S1P binding agent to the chemotherapeutic treatment dramatically improved survivability of the mice. See FIG. 14.

Example 12

Anti-S1P mAb Administered Alone Eliminates Established Human Ovarian Tumors While Examples 1 and 12 demonstrate that an anti-S1P mAb is efficacious in reducing tumor size when administered alone or in combination with cytotoxic agents, this example demonstrates that, using the right human tumor type, one can demonstrate elimination of established tumors, i.e., a cure may be effected.

Figure 15:
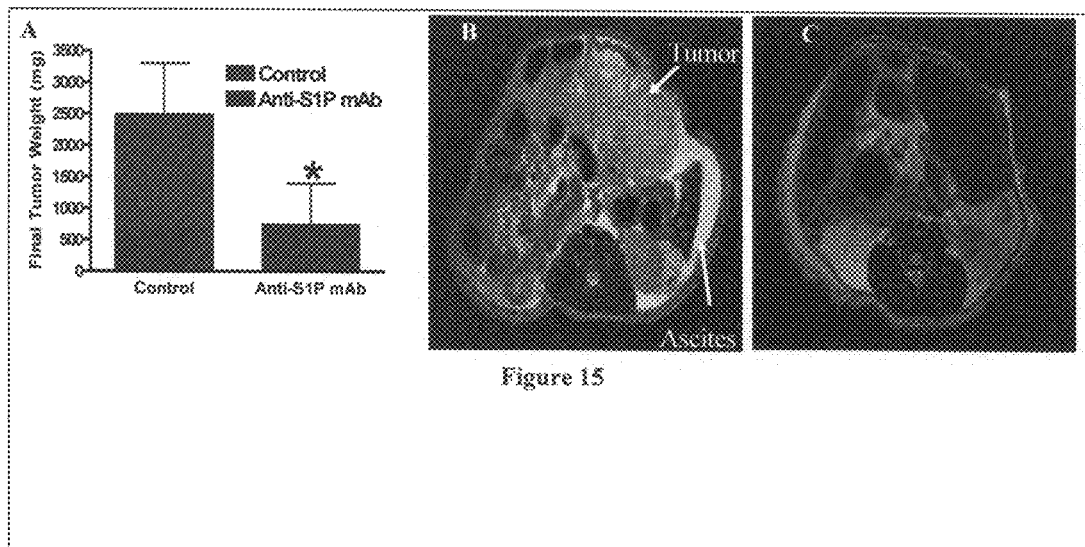
FIG. 15 provides data from experiments involving human ovarian SKOV3 tumors. The tumors were reduced with treatment with the anti-S1P mAb. Panel A: Final tumor weights from control and antibody-treated mice. Data are means±SEM of five non-treated control and five mAb-treated mice. *p<0.01. Panel B-C. MRI images of the peritoneal cavity from a representative control (B) and mAb-treated mice (C) are also provided. Imaging of the control mice revealed large tumors and the accumulation of ascites fluid. This mAb-treated mouse was absent of tumor and lacked ascites fluid, as was the case in three of the five mAb-treated mice.

FIG. 15 demonstrates that the anti-S1P mAb was efficacious in eliminating established orthotopic SKOV3 human ovarian tumors in nude mice. In this model, tumors were allowed to establish for two weeks prior to the initiation of treatment. MRI analysis revealed that all saline control mice contained large tumors throughout the peritoneal cavity and that these mice had accumulated observable amounts of ascites fluid. Conversely, in three out of the five animals treated with the anti-S1P mAb at 25 mg/kg i.p. every three days, no tumors or ascites were detected during MRI analysis or upon dissection of the peritoneal cavity after termination. Only two out of the five animals treated with the anti-S1P mAb had detectable tumors; significantly, these tumors were 68% smaller (750 mg versus 2300 mg) than tumors from the saline-treated animals (*p<0.05). In addition, the animals treated with the anti-S1P mAb and no tumors had a large amount of subcutaneous fat around their bellies, confirming the normal body weights and over-all health exhibited by antibody-treated animals.

Example 13

Angiogenesis and Age-Related Macular Degeneration

The purpose of the experiments described in this example was to determine if an anti-S1P mAb could reduce the angiogenesis in a model other than tumor angiogenesis. For these studies, an established animal model of Age-related Macular Degeneration (AMD) was employed, namely choroidal neovascularization (CNV) by rupture of Bruch's membrane with laser burns using a slit lamp.

The vision impairment of AMD is a consequence of both scaring (i.e., fibrosis, fibrogenesis) and neovascularization. Because S1P is pro-angiogenic, it was reasoned that the anti-S1P mAb used in the experiments described in the previous examples would inhibit angiogenesis by reducing the survival, migration, and proliferation of endothelial cells (ECs); inhibit scar formation by reducing the survival, migration, and proliferation of fibroblasts; and inhibit the cross-talk between S1P with pro-angiogenic compounds including VEGF, bFGF, interleukins, and growth factors that contribute to uncontrolled vascularization during AMD. Thus, the uncontrolled proliferation of cells such as the ECs in AMD could be considered a hyperproliferative cell disorder.

Here, treatments consisted of intravitreal (IVR) injections of either the anti-S1P mAb or a non-specific isotype-matched mouse mAb. IVR injections consisted of 0.5 ug of the anti-S1P mAb diluted into 2 uL or an equal volume of vehicle. IVR injections were administered every 7 days starting 1 day prior to laser burns and lasting for the duration of the study. Just prior to IVR injections, mice were anesthetized with ketamine/xylene delivered IP. Under anesthesia the animal's eyes were moisturized frequently with normal saline. IVR injections were performed slowly into each animal's right eye with a 32 gauge needle. For all IVR injections, the eyes were covered with moisturizing Vaseline-containing standard antibiotics. The pupils of the mice were dilated with phenylephrine/atropine for 10 minutes and then anesthetized with ketamine/xyelene (5:1) for 5 minutes prior to inducing the laser burns. A cover slip was placed on the surface of the eye (lower side) with a clear ophthalmologic media to act as a lens for the laser. A light was shone into the eye to visualize the optical nerve and the neural retina. A fine laser was then focused onto the back of the retina and was set perpendicular to the back of the eye. Three burns were placed 1 optical disc (size of the optical nerve) away from the optical nerve between blood vessels (avoiding blood vessels). The settings for the laser were as follows: duration of 100 mS, intensity of 250 mW, and a diameter of 50 microns. The laser burns traveled through the neural retina and focused on the pigmentation of the RPE layer, causing a rupture of Bruch's membrane. Immediately after the burn, a pocket of fluid formed around the burn and marked the spot of the burn. The pocket resulted from fluid expanding from the heat of the burn. The pocket eventually diminished but a small burn spot could still be observed. Animals were observed until they fully recovered from the anesthesia.

Two weeks after rupture of Bruch's membrane, the animals were sacrificed and their eyes harvested and placed in paraformaldehyde overnight. The eyes were then washed in PBS and the RPE-choroid-sclera complex was isolated from the neural retina. The complex (~200 microns in thickness) was then incubated in PBS containing Triton X-100 and an anti-glutanin-Rhodamine antibody overnight. The complex was then washed and flat mounted for evaluation. Using the Z-line imaging with confocal microscopy, 4 micron sections are imaged from the top to the bottom of the complex (~50 images). The central scar/vascularized area (~middle of the complex) was manually outlined and the images were independently analyzed for background levels of fluorescence. The background fluorescence was subtracted from the outlined area of each image and then each area was analyzed for relative fluorescence. The total fluorescence was then calculated. Each animal, with the 3 burns, was an n of 1.

Figure 16:
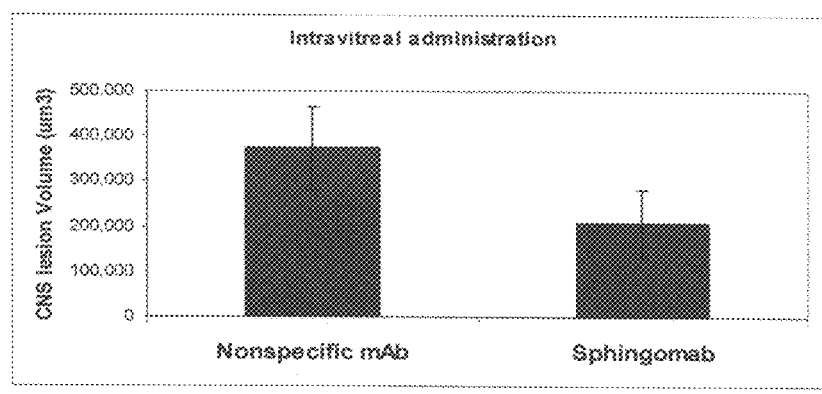
FIG. 16 plots the volume of the CNV lesions induced by laser burns after intravitreal injection of either the anti-S1P mAb (sphingomab) or an isotype-matched mouse $IgG_1$ kappa mouse antibody.

As FIG. 16 shows, the anti-S1P mAb significantly (p<0.05) reduced CNV lesion formation (~50% reduction) when administered via IVR injection, compared to IVR injection of a isotype matched non-specific monoclonal antibody.

Example 14

Fibrogenesis

Hyperproliferative disorders involving fibroblasts (i.e., fibrogenesis) include, but are not limited to, disorders of excessive scaring (i.e., fibrosis) such as age-related macular degeneration (AMD), cardiac remodeling and failure associated with myocardial infarction, excessive wound healing such as commonly occurs as a consequence of surgery or injury, keloids, and fibroid tumors. This Example 14 demonstrates that S1P is a potent activator of fibroblast proliferation, migration, and collagen gene expression in vitro and in vivo, and that an anti-S1P mAb is effective in reducing the S1P-mediated effects on fibroblast activity. In addition, the antibody was shown to mitigate scar formation in a cardiac model.

Figure 17:
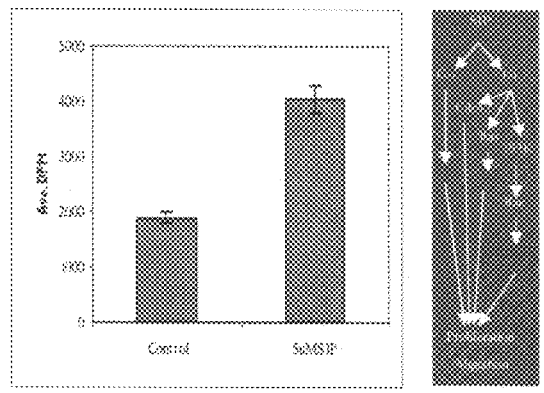
FIG. 17 shows S1P-mediated stimulation of fibroblast proliferation. Primary mouse cardiac fibroblasts were treated with 5 µM S1P for 24 hr. Cell viability was measured using 3H-thymidine incorporation to assess proliferation. The inset shows a putative role of Rho and other signaling components in the proliferation and migration responses of fibroblasts to S1P.
Figure 18:
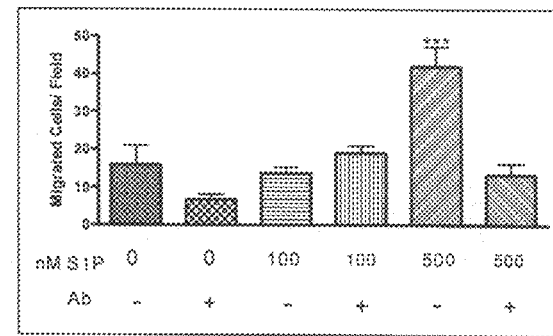
FIG. 18 shows that S1P increases migration in cardiac fibroblasts, which effect can be abrogated by an anti-S1P antibody. 500 nM elicited the best migration response, resulting in over two-fold increase in migration. *** $p<0.001$
Figure 19:
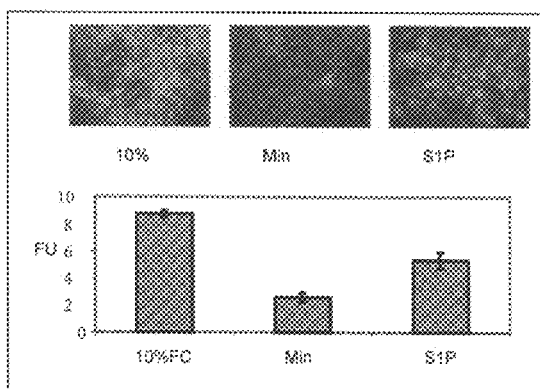
FIG. 19 shows that S1P induces collagen expression in isolated fibroblasts. The top panels are representative pictures of GFP expression driven from a collagen promoter. The graph plots quantified fluorescence (FU=mean fluorescence units/mg protein) from three separate experiments. Increased GFP expression coordinates with increased collagen expression.

In vitro work with cultured fibroblasts demonstrated the potent ability of S1P to activate fibroblast proliferation (FIG. 17), migration (FIG. 18), and collagen gene expression (FIG. 19). In these experiments, the anti-S1P mAb mitigated S1P-mediated effects and resulted in a diminution of fibroblast activity.

Figure 20:
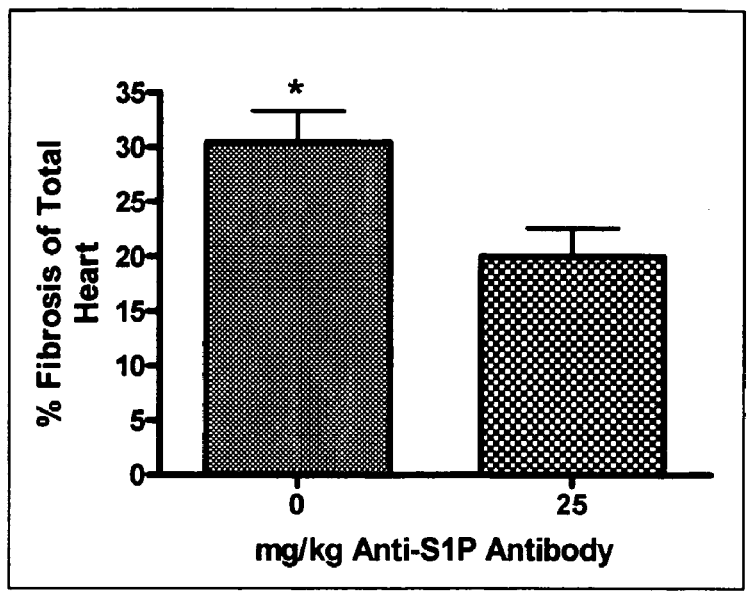
FIG. 20 graphically illustrates that an anti-S1P mAb can reduce fibrosis in hearts from mice given permanent infarctions and then sacrificed two weeks later.
Figure 21:
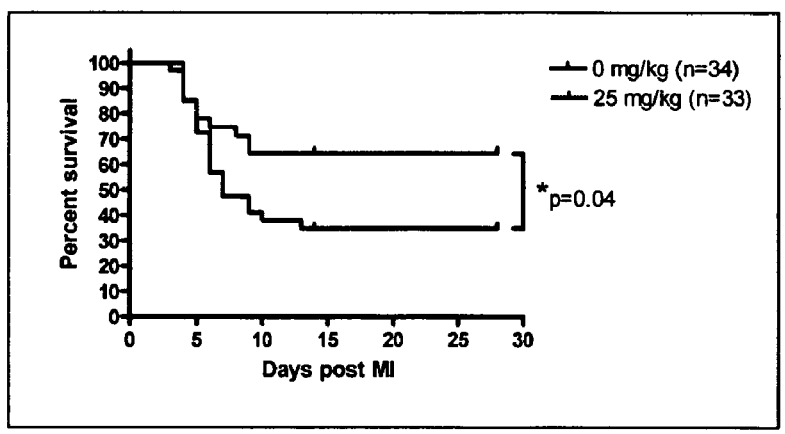
FIG. 21 shows Kaplan-Meier plots of mice receiving permanent myocardial infarctions and treated either with vehicle control (red line) or 25 mg/kg every 3 days i.p.

In order to demonstrate the beneficial effects of reducing fibroblast-mediated scar formation, an in vivo model of heart failure was developed by giving mice permanent coronary ligations during thoracotomy followed by a two-week take downs (FIG. 20). In these studies, the anti-S1P mAb (25 mg/kg) was administered via i.p. 48 hr. after the infarcts, followed by dosing every three days until termination of the study. 48 hr. post-infarct induction was chosen because it was reasoned that some scar formation was beneficial during this period and that the angiogenic effects of S1P would also be manifested immediately after the infarcts but would not necessarily be needed thereafter. Further, it was reasoned that excessive scar formation would be counterproductive after the 48 hr. period due to the profound maladaptive fibrosis that commonly results from the remodeling process. FIG. 21 shows the increase in survivability of infarcted mice that were treated with the anti-S1P mAb and demonstrates that mitigating maladaptive cardiac fibrosis can result in improved survival.

All of the compositions, articles, and methods disclosed and claimed herein can be made and executed without undue experimentation in light of the present disclosure. While the compositions, articles, and methods of this invention have been described in terms of preferred embodiments, it will be apparent to those of skill in the art that variations may be applied to the compositions, articles, and methods without departing from the spirit and scope of the invention. All such variations and equivalents apparent to those skilled in the art, whether now existing or later developed, are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications are herein incorporated by reference in their entirety for all purposes and to the same extent as if each individual publication was specifically and individually indicated to be incorporated by reference in its entirety for any and all purposes.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating an S1P-associated hyperproliferative disease associated with aberrant cardiac remodeling, comprising administering to a mammal known or suspected to suffer therefrom a therapeutically effective amount of an anti-S1P antibody to lower the effective concentration of S1P in the mammal, thereby treating the S1P-associated hyperproliferative disease associated with aberrant cardiac remodeling.

2. A method according to claim 1 wherein the S1P-associated hyperproliferative disease associated with aberrant cardiac remodeling is cardiac failure.

3. A method according to claim 1 wherein the S1P-associated hyperproliferative disease associated with aberrant cardiac remodeling is restenosis.

4. A method according to claim 1 wherein the mammal is selected from the group consisting of bovine, canine, equine, ovine and porcine animals.

5. A method according to claim 1 wherein the mammal is human.

6. A method according to claim 1 wherein the anti-S1P antibody is part of a composition that further comprises a carrier, optionally a pharmaceutically acceptable carrier.

7. A method according to claim 1 wherein the composition comprising the anti-S1P antibody is administered as a monotherapy.

8. A method according to claim 1 wherein the composition comprising the anti-S1P antibody is administered as part of a combination therapy.

9. A method according to claim 8 wherein the combination therapy, in addition to administration of the composition comprising the anti-S1P antibody, further comprises surgery.

* * * * *